US010302653B2

(12) United States Patent
Dong

(10) Patent No.: US 10,302,653 B2
(45) Date of Patent: May 28, 2019

(54) DISTINGUISHING ANTAGONISTIC AND AGONISTIC ANTI B7-H1 ANTIBODIES

(71) Applicant: Mayo Foundation for Medical Education and Research, Rochester, MN (US)

(72) Inventor: Haidong Dong, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 239 days.

(21) Appl. No.: 15/311,552

(22) PCT Filed: May 21, 2015

(86) PCT No.: PCT/US2015/031993
§ 371 (c)(1),
(2) Date: Nov. 16, 2016

(87) PCT Pub. No.: WO2015/179654
PCT Pub. Date: Nov. 26, 2015

(65) Prior Publication Data
US 2017/0089918 A1 Mar. 30, 2017

Related U.S. Application Data

(60) Provisional application No. 62/001,984, filed on May 22, 2014.

(51) Int. Cl.
| G01N 33/00 | (2006.01) |
| G01N 33/68 | (2006.01) |
| A61K 39/395 | (2006.01) |
| C07K 16/28 | (2006.01) |
| G01N 33/574 | (2006.01) |
| A61K 39/00 | (2006.01) |

(52) U.S. Cl.
CPC ..... *G01N 33/6854* (2013.01); *A61K 39/3955* (2013.01); *C07K 16/2827* (2013.01); *G01N 33/57484* (2013.01); *A61K 2039/505* (2013.01); *C07K 2317/73* (2013.01); *C07K 2317/74* (2013.01); *C07K 2317/75* (2013.01); *C07K 2317/76* (2013.01); *G01N 2333/70532* (2013.01); *G01N 2333/912* (2013.01); *G01N 2440/14* (2013.01)

(58) Field of Classification Search
None
See application file for complete search history.

(56) References Cited

U.S. PATENT DOCUMENTS

| 3,687,808 A | 8/1972 | Merigan, Jr. et al. |
| 4,034,074 A | 7/1977 | Miles |
| 4,036,945 A | 7/1977 | Haber |
| 4,098,876 A | 7/1978 | Piasio et al. |
| 4,233,402 A | 11/1980 | Maggio et al. |
| 4,257,774 A | 3/1981 | Richardson et al. |
| 4,272,398 A | 6/1981 | Jaffe |
| 4,331,647 A | 5/1982 | Goldenberg |
| 4,376,110 A | 3/1983 | David et al. |
| 4,469,863 A | 9/1984 | Ts'o et al. |
| 4,650,764 A | 3/1987 | Temin et al. |
| 4,769,330 A | 9/1988 | Paoletti et al. |
| 4,816,567 A | 3/1989 | Cabilly et al. |
| 4,861,627 A | 8/1989 | Mathiowitz et al. |
| 4,861,719 A | 8/1989 | Miller |
| 4,925,673 A | 5/1990 | Steiner et al. |
| 4,935,496 A | 6/1990 | Kudo et al. |
| 4,946,778 A | 8/1990 | Ladner et al. |
| 4,980,289 A | 12/1990 | Temin et al. |
| 4,987,071 A | 1/1991 | Cech et al. |
| 5,013,556 A | 5/1991 | Woodle et al. |
| 5,124,263 A | 6/1992 | Temin et al. |
| 5,155,020 A | 10/1992 | Paoletti |
| 5,155,027 A | 10/1992 | Sledziewski et al. |
| 5,175,099 A | 12/1992 | Wills |
| 5,204,243 A | 4/1993 | Paoletti |
| 5,214,136 A | 5/1993 | Lin et al. |
| 5,218,105 A | 6/1993 | Cook et al. |
| 5,225,336 A | 7/1993 | Paoletti |
| 5,225,538 A | 7/1993 | Capon et al. |
| 5,235,033 A | 8/1993 | Summerton et al. |
| 5,240,846 A | 8/1993 | Collins et al. |
| 5,254,678 A | 10/1993 | Haseloff et al. |
| 5,278,056 A | 1/1994 | Bank et al. |
| 5,284,656 A | 2/1994 | Platz et al. |
| 5,296,347 A | 3/1994 | LaMotte, III |
| 5,391,682 A | 2/1995 | Ogawa et al. |
| 5,451,569 A | 9/1995 | Wong et al. |

(Continued)

FOREIGN PATENT DOCUMENTS

| EP | 1074617 | 2/2001 |
| EP | 1537878 | 6/2005 |

(Continued)

OTHER PUBLICATIONS

Dong et al., 2003, J. Clin. Invest. vol. 111: 363-370.*
Haugland et al., "Unit 16.5 antibody conjugates for cell biology," *Current Protocols in Cell Biology*, 6:16.5:16.5-16.5.22, Epub May 1, 2001.
*Academic Press Dictionary of Science and Technology* (definition for the term "polyclonal"); Oxford: Elsevier Science & Technology (1996); retrieved Oct. 22, 2008, from http://www.credoreference.com/entry/3144515/.
Acsadi et al., "Direct gene transfer and expression into rat heart in vivo," *New Biol.*, 3(1):71-81, Jan. 1991.
Adachi et al., "Enhanced and accelerated lymphoproliferation in Fas-null mice.," *Proc Natl Acad Sci U S A.*, 93(5):2131-2136, Mar. 5, 1996.

(Continued)

*Primary Examiner* — Amy E Juedes
(74) *Attorney, Agent, or Firm* — Fish & Richardson P.C.

(57) ABSTRACT

Materials and methods for distinguishing agonistic anti-B7-H1 antibodies from antagonistic anti-B7-H1 antibodies, and for treating subjects diagnosed with clinical conditions such as cancer, pathogenic infection, or autoimmune disease.

6 Claims, 24 Drawing Sheets

Specification includes a Sequence Listing.

(56) References Cited

U.S. PATENT DOCUMENTS

| | | |
|---|---|---|
| 5,502,167 A | 3/1996 | Waldmann et al. |
| 5,521,288 A | 5/1996 | Linsley et al. |
| 5,530,101 A | 6/1996 | Queen et al. |
| 5,558,864 A | 9/1996 | Bendig et al. |
| 5,565,332 A | 10/1996 | Hoogenboom et al. |
| 5,567,584 A | 10/1996 | Sledziewski et al. |
| 5,585,089 A | 12/1996 | Queen et al. |
| 5,596,086 A | 1/1997 | Matteucci et al. |
| 5,639,641 A | 6/1997 | Pedersen et al. |
| 5,674,704 A | 10/1997 | Goodwin et al. |
| 5,675,848 A | 10/1997 | Kappel |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,705,154 A | 1/1998 | Dalie et al. |
| 5,714,147 A | 2/1998 | Capon et al. |
| 5,733,743 A | 3/1998 | Johnson et al. |
| 5,750,078 A | 5/1998 | Shitara et al. |
| 5,750,375 A | 5/1998 | Sledziewski et al. |
| 5,750,666 A | 5/1998 | Caruthers et al. |
| 5,770,403 A | 6/1998 | Dalie et al. |
| 5,843,725 A | 12/1998 | Sledziewski et al. |
| 5,861,310 A | 1/1999 | Freeman et al. |
| 5,874,240 A | 2/1999 | Ni et al. |
| 5,928,893 A | 7/1999 | Kang et al. |
| 5,942,607 A | 8/1999 | Freeman et al. |
| 6,018,026 A | 1/2000 | Sledziewski et al. |
| 6,210,669 B1 | 4/2001 | Aruffo et al. |
| 6,291,212 B1 | 9/2001 | Sledziewski et al. |
| 6,291,646 B1 | 9/2001 | Sledziewski et al. |
| 6,297,008 B1 | 10/2001 | Okamoto et al. |
| 6,300,099 B1 | 10/2001 | Sledziewski et al. |
| 6,303,121 B1 | 10/2001 | Kwon |
| 6,323,323 B1 | 11/2001 | Sledziewski et al. |
| 6,355,779 B1 | 3/2002 | Goodwin et al. |
| 6,423,885 B1 | 7/2002 | Waterhouse et al. |
| 6,458,934 B1 | 10/2002 | Hong et al. |
| 6,630,575 B2 | 10/2003 | Coyle et al. |
| 6,635,750 B1 | 10/2003 | Coyle et al. |
| 6,740,493 B1 | 5/2004 | Long et al. |
| 6,743,619 B1 | 6/2004 | Tang et al. |
| 6,803,192 B1 | 10/2004 | Chen |
| 6,891,030 B2 | 5/2005 | Chen |
| 6,919,193 B2 | 7/2005 | Tang et al. |
| 6,943,150 B1 | 9/2005 | Altieri |
| 6,965,018 B2 | 11/2005 | Mikesell et al. |
| 7,029,674 B2 | 4/2006 | Carreno et al. |
| 7,030,219 B2 | 4/2006 | Pardoll et al. |
| 7,122,351 B2 | 10/2006 | Moore et al. |
| 7,279,567 B2 | 10/2007 | Mikesell et al. |
| 7,358,354 B2 | 4/2008 | Mikesell et al. |
| 7,368,531 B2 | 5/2008 | Rosen et al. |
| 7,381,794 B2 | 6/2008 | Moore et al. |
| 7,414,122 B2 | 8/2008 | Fox et al. |
| 7,432,059 B2 | 10/2008 | Freeman et al. |
| 7,432,062 B2 | 10/2008 | Coyle et al. |
| 7,432,351 B1 | 10/2008 | Chen |
| 7,449,300 B2 | 11/2008 | Chen et al. |
| 7,560,540 B2 | 7/2009 | Pardoll et al. |
| 7,563,869 B2 | 7/2009 | Honjo et al. |
| 7,582,439 B2 | 9/2009 | Cory et al. |
| 7,595,048 B2 | 9/2009 | Honjo et al. |
| 7,651,686 B2 | 1/2010 | Chen et al. |
| 7,709,214 B2 | 5/2010 | Freeman et al. |
| 7,723,479 B2 | 5/2010 | Mikesell et al. |
| 7,794,710 B2 | 9/2010 | Chen et al. |
| 7,892,540 B2 | 2/2011 | Chen et al. |
| 8,039,589 B1 | 10/2011 | Chen |
| 8,053,414 B2 | 11/2011 | Pardoll et al. |
| 8,053,558 B2 | 11/2011 | Pardoll et al. |
| 8,163,550 B2 | 4/2012 | Chen et al. |
| 8,268,635 B2 | 9/2012 | Ferrante et al. |
| 8,273,864 B2 | 9/2012 | Chen |
| 8,460,927 B2 | 6/2013 | Chen |
| 8,772,026 B2 | 7/2014 | Chen et al. |
| 8,981,063 B2 | 3/2015 | Chen |
| 9,302,005 B2 | 4/2016 | Dong et al. |
| 2002/0076409 A1 | 6/2002 | March et al. |
| 2002/0091246 A1 | 7/2002 | Pardoll et al. |
| 2002/0095024 A1 | 7/2002 | Mikesell et al. |
| 2002/0106730 A1 | 8/2002 | Coyle et al. |
| 2002/0107363 A1 | 8/2002 | Fox et al. |
| 2002/0110836 A1 | 8/2002 | Freeman et al. |
| 2002/0119121 A1 | 8/2002 | Vitiello et al. |
| 2002/0160395 A1 | 10/2002 | Altieri et al. |
| 2002/0160973 A1 | 10/2002 | Pero et al. |
| 2002/0164600 A1 | 11/2002 | Freeman et al. |
| 2002/0168719 A1 | 11/2002 | Kwon |
| 2002/0177551 A1 | 11/2002 | Terman |
| 2003/0039653 A1 | 2/2003 | Chen et al. |
| 2003/0142359 A1 | 7/2003 | Bean et al. |
| 2003/0171551 A1 | 9/2003 | Rosenblatt et al. |
| 2003/0208058 A1 | 11/2003 | Fiscella et al. |
| 2003/0223989 A1 | 12/2003 | Pluenneke |
| 2003/0232323 A1 | 12/2003 | Freeman et al. |
| 2004/0010134 A1 | 1/2004 | Rosen et al. |
| 2004/0109847 A1 | 6/2004 | Chen et al. |
| 2004/0180047 A1 | 9/2004 | Chen |
| 2004/0247563 A1 | 12/2004 | Lynch et al. |
| 2005/0013811 A1 | 1/2005 | Chen et al. |
| 2005/0228170 A1 | 10/2005 | Fox et al. |
| 2005/0260716 A1 | 11/2005 | Moore et al. |
| 2006/0034826 A1 | 2/2006 | Carreno et al. |
| 2006/0068386 A1 | 3/2006 | Slesarev et al. |
| 2006/0084794 A1 | 4/2006 | Rosen et al. |
| 2006/0110383 A1 | 5/2006 | Honjo et al. |
| 2006/0159685 A1 | 7/2006 | Mikesell et al. |
| 2006/0223088 A1 | 10/2006 | Rosen et al. |
| 2006/0276422 A1 | 12/2006 | Usman et al. |
| 2007/0037206 A1 | 2/2007 | Rosen et al. |
| 2007/0041963 A1 | 2/2007 | Rosen et al. |
| 2007/0065427 A1 | 3/2007 | Freeman et al. |
| 2007/0092504 A1 | 4/2007 | Carreno et al. |
| 2007/0099833 A1 | 5/2007 | Rosen et al. |
| 2007/0122378 A1 | 5/2007 | Freeman et al. |
| 2007/0224663 A1 | 9/2007 | Rosen et al. |
| 2007/0231344 A1 | 10/2007 | Leadbetter et al. |
| 2008/0025979 A1 | 1/2008 | Honjo et al. |
| 2008/0118511 A1 | 5/2008 | Freeman et al. |
| 2008/0226662 A1 | 9/2008 | Pardoll et al. |
| 2008/0241175 A1 | 10/2008 | Pardoll et al. |
| 2009/0042292 A1 | 2/2009 | Chen |
| 2009/0068193 A1 | 3/2009 | Chen et al. |
| 2009/0075338 A1 | 3/2009 | Moore et al. |
| 2009/0176317 A1 | 7/2009 | Kwon et al. |
| 2009/0215084 A1 | 8/2009 | Kwon et al. |
| 2009/0269783 A1 | 10/2009 | Coyle et al. |
| 2009/0304711 A1 | 12/2009 | Pardoll et al. |
| 2010/0015642 A1 | 1/2010 | Kwon et al. |
| 2010/0285039 A1 | 11/2010 | Chen |
| 2011/0020325 A1 | 1/2011 | Kwon et al. |
| 2011/0010409 A1 | 5/2011 | Strome et al. |
| 2012/0065374 A1 | 3/2012 | Pardoll et al. |
| 2012/0065385 A1 | 3/2012 | Pardoll et al. |
| 2012/0225043 A1 | 9/2012 | Chen et al. |
| 2013/0058936 A1 | 3/2013 | Bruenker et al. |
| 2013/0123566 A1 | 5/2013 | Lupoid et al. |
| 2013/0251736 A1 | 9/2013 | Kwon et al. |
| 2013/0273656 A1 | 10/2013 | Hendrickson |
| 2014/0031260 A1 | 1/2014 | O'Donnell et al. |
| 2014/0242080 A1 | 8/2014 | Roche |
| 2014/0271674 A1 | 9/2014 | Dong |
| 2014/0329248 A1 | 11/2014 | Kwon et al. |
| 2014/0335541 A1 | 11/2014 | Kwon et al. |
| 2015/0111232 A1 | 4/2015 | Kwon |
| 2016/0153996 A1 | 6/2016 | Kwon et al. |
| 2016/0154000 A1 | 6/2016 | Kwon |
| 2016/0176967 A1 | 6/2016 | Dong et al. |
| 2016/0251437 A1 | 9/2016 | Dong et al. |

(56) References Cited

U.S. PATENT DOCUMENTS

2017/0173030 A1 6/2017 Dong
2017/0363634 A1 12/2017 Kwon et al.

FOREIGN PATENT DOCUMENTS

| WO | WO 1990/07861 | 7/1990 |
|---|---|---|
| WO | WO 1991/10741 | 7/1991 |
| WO | WO 1991/11465 | 8/1991 |
| WO | WO 1991/17271 | 11/1991 |
| WO | WO 1992/00092 | 1/1992 |
| WO | WO 1992/01047 | 1/1992 |
| WO | WO 1992/20791 | 11/1992 |
| WO | WO 1993/01222 | 1/1993 |
| WO | WO 1995/05464 | 2/1995 |
| WO | WO 1995/07707 | 3/1995 |
| WO | WO 1996/29348 | 9/1996 |
| WO | WO 1997/17613 | 5/1997 |
| WO | WO 1997/17614 | 5/1997 |
| WO | WO 1997/24447 | 7/1997 |
| WO | WO 1998/16249 | 4/1998 |
| WO | WO 1998/23635 | 6/1998 |
| WO | WO 1998/33914 | 8/1998 |
| WO | WO 1998/36096 | 8/1998 |
| WO | WO 1999/36093 | 7/1999 |
| WO | WO 1999/64597 | 12/1999 |
| WO | WO 2000/026342 | 5/2000 |
| WO | WO 2000/029445 | 5/2000 |
| WO | WO 2000/029582 | 5/2000 |
| WO | WO 2000/041508 | 7/2000 |
| WO | WO 2000/055375 | 9/2000 |
| WO | WO 2000/061612 | 10/2000 |
| WO | WO 2001/034629 | 5/2001 |
| WO | WO 2001/062905 | 8/2001 |
| WO | WO 2001/070979 | 9/2001 |
| WO | WO 2001/083750 | 11/2001 |
| WO | WO 2001/094413 | 12/2001 |
| WO | WO 2002/000692 | 1/2002 |
| WO | WO 2002/000730 | 1/2002 |
| WO | WO 2002/002587 | 1/2002 |
| WO | WO 2002/002891 | 1/2002 |
| WO | WO 2002/008279 | 1/2002 |
| WO | WO 2002/078731 | 1/2002 |
| WO | WO 2002/024891 | 3/2002 |
| WO | WO 2002/046449 | 6/2002 |
| WO | WO 2002/057453 | 7/2002 |
| WO | WO 2002/079474 | 10/2002 |
| WO | WO 2002/081731 | 10/2002 |
| WO | WO 2002/086083 | 10/2002 |
| WO | WO 2003/006632 | 1/2003 |
| WO | WO 2003/008583 | 1/2003 |
| WO | WO 2003/049755 | 6/2003 |
| WO | WO 2004/085418 | 10/2004 |
| WO | WO 2006/042237 | 4/2006 |
| WO | WO 2006/050172 | 5/2006 |
| WO | WO 2006/133396 | 12/2006 |
| WO | WO 2008/037080 | 4/2008 |
| WO | WO 2008/083174 | 7/2008 |
| WO | WO 2009/023566 | 2/2009 |
| WO | WO 2009/029342 | 3/2009 |
| WO | WO 2009/114110 | 9/2009 |
| WO | WO 2010/027423 | 3/2010 |
| WO | WO 2010/027827 | 3/2010 |
| WO | WO 2010/027828 | 3/2010 |
| WO | WO 2010/098788 | 9/2010 |
| WO | WO 2011/066342 | 6/2011 |
| WO | WO 2011/066389 | 6/2011 |
| WO | WO 2013/003112 | 2/2013 |
| WO | WO 2013/019906 | 2/2013 |
| WO | WO 2013/090552 | 6/2013 |
| WO | WO 2013/132044 | 9/2013 |
| WO | WO 2015/050663 | 4/2015 |
| WO | WO 2016/014148 | 1/2016 |

OTHER PUBLICATIONS

Adachi et al., "Aberrant transcription caused by the insertion of an early transposable element in an intron of the Fas antigen gene of lpr mice," Proc Natl Acad Sci U S A., 90(5):1756-1760, Mar. 1, 1993.
Agata et al., "Expression of the PD-1 antigen on the surface of stimulated mouse T and B lymphocytes," Int Immunol., 8(5):765-772, May 1996.
Ahmadzadeh et al., "Tumor antigen-specific CD8 T cells infiltrating the tumor express high levels of PD-1 and are functionally impaired," Blood, 114(8):1537-1544, Epub May 7, 2009.
Ahonen et al., "Combined TLR and CD40 triggering induces potent CD8+ T cell expansion with variable dependence on type I IFN," J Exp Med., 199(6):775-784, Epub Mar. 8, 2004.
Alderson et al., "Molecular and biological characterization of human 4-1BB and its ligand," Eur J. Immunol., 24(9):2219-2227, Sep. 1994.
Aldovini et al., "Humoral and cell-mediated immune responses to live recombinant BCG-HIV vaccines," Nature, 351(6326):479-482, Jun. 6, 1991.
Allie et al., "Programmed death 1 regulates development of central memory CD8 T cells after acute viral infection," J Immunol., 186(11):6280-6286, Epub Apr. 27, 2011.
Ambrosini et al., "A novel anti-apoptosis gene, survivin, expressed in cancer and lymphoma," Nat Med., 3(8):917-921, Aug. 1997.
Anderson, "Human gene therapy," Science, 256(5058):808-813, May 8, 1992.
Andorsky et al., "Programmed death ligand 1 is expressed by non-hodgkin lymphomas and inhibits the activity of tumor-associated T cells," Clin Cancer Res., 17(13):4232-4244, Epub May 3, 2011.
Anikeeva et al., "Distinct role of lymphocyte function-associated antigen-1 in mediating effective cytolytic activity by cytotoxic T lymphocytes," Proc Natl Acad Sci U S A., 102(18):6437-6442, Epub Apr. 25, 2005.
Ansari et al., "The programmed death-1 (PD-1) pathway regulates autoimmune diabetes in nonobese diabetic (NOD) mice," J Exp Med., 198(1):63-69, Jul. 7, 2003.
Anukam et al., "Augmentation of antimicrobial metronidazole therapy of bacterial vaginosis with oral probiotic Lactobacillus rhamnosus GR-1 and Lactobacillus reuteri RC-14: randomized, double-blind, placebo controlled trial," Microbes Infect., 8(6):1450-1454, Epub Mar. 29, 2006.
Attwood et al., "Genomics. The Babel of bioinformatics," Science, 290(5491):471-473, Oct. 20, 2000.
Azuma et al., "B7-H1 is a ubiquitous antiapoptotic receptor on cancer cells," Blood., 111(7):3635-3643, Epub Jan. 25, 2008.
Baitsch et al., "Exhaustion of tumor-specific CD8+T cells in metastases from melanoma patients," J Clin Invest., 121(6):2350-2360, Epub May 9, 2011.
Bajorath et al., "Molecular modeling of CD28 and three-dimensional analysis of residue conservation in the CD28/CD152 family," J Mol Graph Model., 15(2):135-9, 108-111, Apr. 1997.
Baldrick, "Pharmaceutical excipient development: the need for preclinical guidance," Regul Toxicol Pharmacol., 32(2):210-218, Oct. 2000.
Banáth et al., "Residual gammaH2AX foci as an indication of lethal DNA lesions," BMC Cancer., 10:4, Jan. 5, 2010.
Barber et al., "Restoring function in exhausted CD8 T cells during chronic viral infection," Nature, 439(7077):682-687, Epub Dec. 28, 2005.
BD PharmingenTM Technical Data Sheet, "Purified Rat Anti-Mouse Ly-6G (Gr-1) Monoclonal Antibody for Immunohistochemistry (IHC)" 1 page, 2003.
Benita et al., "Characterization of drug-loaded poly(d,l-lactide) microspheres," J Pharm Sci., 73(12):1721-1724, Dec. 1984.
Benlalam et al., "Comprehensive analysis of the frequency of recognition of melanoma-associated antigen (MAA) by CD8 melanoma infiltrating lymphocytes (TIL) implications for immunotherapy," Eur J Immunol., 31(7):2007-2015, Jul. 31, 2001.
Bennardo et al., "Alternative-NHEJ is a mechanistically distinct pathway of mammalian chromosome break repair," PLoS Genet., 4(6):e1000110, Jun. 27, 2008.

(56) References Cited

OTHER PUBLICATIONS

Berman et al., "The Protein Data Bank," *Nucleic Acids Res.*, 28(1):235-242, Jan. 1, 2000.
Berrien-Elliott et al., "Durable adoptive immunotherapy for leukemia produced by manipulation of multiple regulatory pathways of CD8+ T-cell tolerance," *Cancer Res.*, 73(2):605-616, Jan. 15, 2013.
Berthon et al., "In acute myeloid leukemia, B7-H1 (PD-L1) protection of blasts from cytotoxic T cells is induced by TLR ligands and interferon-gamma and can be reversed using MEK inhibitors," *Cancer Immunol Immunother.*, 59(12):1839-1849, Epub Sep. 4, 2010.
Betts et al., "Sensitive and viable identification of antigen-specific CD8+ T cells by a flow cytometric assay for degranulation," *J Immunol Methods.*, 281(1-2):65-78, Oct. 1, 2003.
Bird et al., "Single-chain antigen-binding proteins," *Science*, 242(4877):423-426, Oct. 21, 1988.
Blank et al., "Blockade of PD-L1 (B7-H1) augments human tumor-specific T cell responses in vitro," *Int J Cancer*, 119(2):317-327, Jul. 15, 2006.
Blank et al., "Interaction of PD-L1 on tumor cells with PD-1 on tumor-specific T cells as a mechanism of immune evasion: implications for tumor immunotherapy," *Cancer Immunol Immunother.*, 54(4):307-314, Epub Dec. 15, 2004.
Blank et al., "PD-L1/B7H-1 inhibits the effector phase of tumor rejection by T cell receptor (TCR) transgenic CD8+ T cells," *Cancer Res.*, 64(3):1140-1145, Feb. 1, 2004.
Blazar et al., "Infusion of anti-B7.1 (CD80) and anti-B7.2 (CD86) monoclonal antibodies inhibits murine graft-versus-host disease lethality in part via direct effects on CD4+ and CD8+ T cells," *J Immunol.*, 157(8):3250-3259, Oct. 15, 1996.
Block, "Medicated Applications," Remington's Pharmaceutical Sciences, 18th edition, Mack Publishing Company, Easton, PA, Chpt 87, pp. 1596-1614, 1990.
Bodine, "mTOR signaling and the molecular adaptation to resistance exercise," *Med Sci Sports Exerc.*, 38(11):1950-1957, Nov. 2006.
Boggio et al., "Interleukin 12-mediated prevention of spontaneous mammary adenocarcinomas in two lines of Her-2/neu transgenic mice," *J Egg Med.*, 188(3):589-596, Aug. 3, 1998.
Boise et al., "CD28 costimulation can promote T cell survival by enhancing the expression of Bcl-XL," *Immunity*, 3(1):87-98, Jul. 1995.
Boletta et al., "High efficient non-viral gene delivery to the rat kidney by novel polycationic vectors," *J Am Soc Nephrol.*, 7(9):1728, abstr A2409, Sep. 1, 1996.
Bona et al., "Immune response: Idiotype anti-idiotype network," *CRC Crit Rev Immunol.*, 33-81, Mar. 1981.
Bonfoco et al., "Inducible nonlymphoid expression of Fas ligand is responsible for superantigen-induced peripheral deletion of T cells," *Immunity*, 9(5):711-720, Nov. 1998.
Bonifaz et al., "Efficient targeting of protein antigen to the dendritic cell receptor DEC-205 in the steady state leads to antigen presentation on major histocompatibility complex class I products and peripheral CD8+ T cell tolerance," *J Exp Med.*, 196(12):1627-1638, Dec. 16, 2002.
Bonifaz et al., "In vivo targeting of antigens to maturing dendritic cells via the DEC-205 receptor improves T cell vaccination," *J Exp Med.*, 199(6):815-824, Mar. 15, 2004.
Bonni et al., "Cell survival promoted by the Ras-MAPK signaling pathway by transcription-dependent and -independent mechanisms," *Science*, 286(5443):1358-1362, Nov. 12, 1999.
Boon et al., "Human T cell responses against melanoma," *Annu Rev Immunol.*, 24:175-208, 2006.
Borson et al., "Brain-infiltrating cytolytic T lymphocytes specific for Theiler's virus recognize H2Db molecules complexed with a viral VP2 peptide lacking a consensus anchor residue," *J Virol.*, 71(7):5244-5250, Jul. 1997.
Bouillet and O'Reilly, "CD95, BIM and 2009 T cell homeostasis," *Nat Rev Immunol.*, 9(7):514-519, Jul. 2009.
Bowie et al, "Deciphering the message in protein sequences: tolerance to amino acid substitutions," *Science*, 247(4948):1306-1310, Mar. 16, 1990.
Brahmer et al., "Safety and activity of anti-PD-L1 antibody in patients with advanced cancer," *N Engl J Med.*, 366(26):2455-2465, Epub Jun. 2, 2012.
Braquet et al., "Effect of endothelin-1 on blood pressure and bronchopulmonary system of the guinea pig," *J Cardiovasc Pharmacol.*, 13 Suppl 5:S143-6; discussion S150, 1989.
Brinkmann et al., "FTY720: altered lymphocyte traffic results in allograft protection," *Transplantation.*, 72(5):764-769, Sep. 15, 2001.
Britton et al., "Leprosy," *Lancet*, 363(9416):1209-1219, Apr. 10, 2004.
Brooks, "Translational genomics: the challenge of developing cancer biomarkers," *Genome Res.*, 22(2):183-187, Feb. 2012.
Brown et al., "Blockade of programmed death-1 ligands on dendritic cells enhances T cell activation and cytokine production.," *J Immunol.*, 170(3):1257-1266, Feb. 1, 2003.
Brozovic et al., "Activation of mitogen-activated protein kinases by cisplatin and their role in cisplatin-resistance," *Cancer Lett.*, 251(1):1-16. Epub Nov. 27, 2006.
Bubenik, "Genetically engineered dendritic cell-based cancer vaccines (Review)," *Int J Oncol.*, 18(3):475-478, Mar. 2001.
Burmer et al, "Frequency and spectrum of c-Ki-ras mutations in human sporadic colon carcinoma, carcinomas arising in ulcerative colitis, and pancreatic adenocarcinoma," *Environ Health Perspect.*, 93:27-31, Jun. 1991.
Buskens et al, "Adenocarcinomas of the gastro-esophageal junction: A comparative study of the gastric cardia and the esophagus with respect to cyclooxygenase-2 expression," Digestive Disease Week Abstracts and Itinerary Planner, 2003, abstract No. 850.
Butte et al., "Interaction of human PD-L1 and B7-1," *Mol Immunol.*, 45(13):3567-3572, Epub Jun. 27, 2008.
Butte et al., "PD-L1 interacts specifically with B7-1 to inhibit T cell proliferation," *Immunity*, 27:111-122, 2007.
Cairns et al., "Immortalization of multipotent growth-factor dependent hemopoietic progenitors from mice transgenic for GATA-1 driven SV40 tsA58 gene," *EMBO J.*, 13(19):4577-4586, Oct. 3, 1994.
Cannons et al., "4-1BB ligand induces cell division, sustains survival, and enhances effector function of CD4 and CD8 T cells with similar efficacy," *J Immunol.*, 167(3):1313-1324, Aug. 1, 2001.
Cao et al., "B7-H1 overexpression regulates epithelial-mesenchymal transition and accelerates carcinogenesis in skin," *Cancer Res.*, 71(4):1235-1243, Epub Dec. 15, 2010.
Carreno et al., "The B7 family of ligands and its receptors: new pathways for costimulation and inhibition of immune responses," *Annu Rev Immunol.*, 20:29-53, Epub Oct. 4, 2001.
Carter et al., "PD-1:PD-L inhibitory pathway affects both CD4(+) and CD8(+) T cells and is overcome by IL-2," *Eur J Immunol.*, 32(3):634-643, Mar. 2002.
Carter et al., "Humanization of an anti-p185HER2 antibody for human cancer therapy," *Proc Natl Acad Sci U S A.*, 89(10):4285-4289, May 15, 1992.
Chakrabarti et al., "Vaccinia virus expression vector: coexpression of beta-galactosidase provides visual screening of recombinant virus plaques," *Mol Cell Biol.*, 5(12):3403-3409, Dec. 1985.
Chambers et al., "Co-stimulation in T cell responses," *Curr Opin Immunol.*, 9(3):396-404, Jun. 1997.
Chan et al., "Autophosphorylation of the DNA-dependent protein kinase catalytic subunit is required for rejoining of DNA double-strand breaks," *Genes Dev.*, 16(18):2333-2338, Sep. 15, 2002.
Chapoval et al., "B7-H3: A costimulatory molecule for T cell activation and IFN-y production," *Nat Immunol.*, 2(3):269-274, Mar. 2001.
Charman, "Lipids, lipophilic drugs, and oral drug delivery—some emerging concepts," *J. Pharm. Sci.*, 89(8):967-978, Aug. 2000.
Chaurand et al., "Peptide and Protein Identification by Matrix-Assisted Laser Desorption Ionization (MALDI) and MALDI-Post-Source Decay Time-of-Flight Mass Spectrometry," *J Am Soc Mass Spectrom.*, 10(2):91-103, Feb. 1999.

(56) References Cited

OTHER PUBLICATIONS

Chen et al., "CD44-deficient mice exhibit enhanced hepatitis after concanavalin A injection: evidence for involvement of CD44 in activation-induced cell death," *J Immunol.*, 166(10):5889-5897, May 1, 2001.
Chen et al., "Costimulation of antitumor immunity by the B7 counterreceptor of the T lymphocyte molecules CD28 and CTLA-4," *Cell*, 71(7):1093-1102, Dec. 24, 1992.
Chen et al., "Tumor immunogenicity determines the effect of co-stimulation by B7 on T-cell mediated tumor immunity," *J Exp Med.*, 179(2):523-532, Feb. 1, 1994.
Chen, "Co-inhibitory molecules of the B7-CD28 family in the control of T-cell immunity," *Nat Rev Immunol.*, 4(5):336-347, May 2004.
Cheville et al., "Comparisons of outcome and prognostic features among histologic subtypes of renal cell carcinoma," *Am J Surg Pathol.*, 27(5):612-624, May 2003.
Choi et al., "Genomic Organization and expression Analysis of B7-H4, an Immune Inhibitory Molecule of the B7 Family," *J Immunol.*, 171(9):4650-4654, Nov. 1, 2003.
Cogoni et al. "Transgene silencing of the al-1 gene in vegetative cells of Neurospora is mediated by a cytoplasmic effector and does not depend on DNA-DNA interactions or DNA methylation ," *EMBO J.*, 15(12):3153-3163, Jun. 17, 1996.
Cogoni et al., "Gene silencing in Neurospora crassa requires a protein homologous to RNA-dependent RNA polymerase," *Nature*, 399(6732):166-169, May 13, 1999.
Cohen et al., "Lpr and gld: Single Gene Models of Systemic Autoimmunity and Lymphoproliferative Disease," *Annu Rev Immunol.*, 9:243-269, 1991.
Cole et al., "The EBV-hybridoma technique and its application to human lung cancer," *Monoclonal Antibodies and Cancer Therapy*, 27:77-96, Jan.-Feb. 1985.
Collins et al., "The B7 family of immune-regulatory ligands," *Genome Biol.*, 6(6):223, 7 pages, Epub May 31, 2005.
Collis et al., "The life and death of DNA-PK," *Oncogene.*, 24(6):949-961, Feb. 3, 2005.
Conacci-Sorrell et al., "Autoregulation of E-cadherin expression by cadherin-cadherin interactions: the roles of beta-catenin signaling, Slug, and MAPK," *J Cell Biol.*, 163(4):847-857, Epub Nov. 17, 2003.
Cone et al., "High-efficiency gene transfer into mammalian cells: generation of helper-free recombinant retrovirus with broad mammalian host range," *Proc Natl Acad Sci U S A.*, 81(20):6349-6353, Oct. 1984.
Connolly, "Analytical molecular surface calculation," *J Appl Crystallogr.*, 16(5):548-558, Oct. 1, 1983.
Corpet, "Multiple sequence alignment with hierarchical clustering," *Nucleic Acids Res.*, 16(22):10881-10890, Nov. 25, 1988.
Cote et al., "Generation of human monoclonal antibodies reactive with cellular antigens," *Proc Natl Acad Sci U S A.*, 80(7):2026-2030, Apr. 1983.
Coyle et al., "The expanding B7 superfamily: increasing complexity in costimulatory signals regulating T cell function," *Nat Immunol.*, 2(3):203-209, Mar. 2001.
Crispe et al., "The liver as a site of T-cell apoptosis: graveyard, or killing field?" *Immunol Rev.*, 174:47-62, Apr. 2000.
Crispe, "Hepatic T cells and liver tolerance," *Nat Rev Immunol.*, 3(1):51-62, Jan. 2003.
Cristiano et al., "Molecular conjugates: a targeted gene delivery vector for molecular medicine," *J Mol Med (Berl).*, 73(10):479-486, Oct. 1995.
Crystal, "Gene therapy strategies for pulmonary disease" *Am J Med.*, 92(suppl 6A):44S-52S, Jun. 22, 1992.
Curiel et al., "Blockade of B7-H1 improves myeloid dendritic cell-mediated antitumor immunity,"*Nat Med.*, 9(5):562-567, Epub Apr. 21, 2003.
Dao et al., "Involvement of CD1 in peripheral deletion of T lymphocytes is independent of NK T cells,"*J Immunol.*, 166(5):3090-3097, Mar. 1, 2001.

Database EM-MUS [Online]EMBL; Accession No. AF142780.1 (version 1), Jun. 1, 1999, 2 pages.
Datta et al., "Akt phosphorylation of BAD couples survival signals to the cell-intrinsic death machinery," *Cell.*, 91(2):231-241, Oct. 17, 1997.
Davidson et al., "Phenotypic, functional, and molecular genetic comparisons of the abnormal lymphoid cells of C3H-1pr/1pr and C3H-gld/gld mice," *J Immunol.*, 136(11):4075-4084, Jun. 1, 1986.
Davidson et al., "Small Molecules, Inhibitors of DNA-PK, Targeting DNA Repair, and Beyond,"*Front Pharmacol.*, vol. 4, Article 5, pp. 1-7, Jan. 31, 2013.
De StGroth et al., "Production of monoclonal antibodies: strategy and tactics," *J Immunol Methods.*, 35(1-2):1-21, 1980.
Debs et al., "Lung-specific delivery of cytokines induces sustained pulmonary and systemic immunomodulation in rats," *J Immunol.*, 140(10):3482-3488, May 15, 1988.
Del Peso et al., "Interleukin-3-induced phosphorylation of BAD through the protein kinase Akt," *Science*, 278(5338):687-689, Oct. 24, 1997.
Dheda et al., "Lung remodeling in tuberculosis," *J Infect Dis.*, 192(7):1201-1209, Epub Aug. 29, 2005.
Diehl et al., "In vivo triggering through 4-1BB enables Th-independent priming of CTL in the presence of an intact CD28 costimulatory pathway," *J Immunol.*, 168(8):3755-3762, Apr. 15, 2002.
Ding et al., "Release of reactive nitrogen intermediates and reactive oxygen intermediates from mouse peritoneal macrophages. Comparison of activating cytokines and evidence for independent production," *J Immunol.*, 141(7):2407-2412, Oct. 1, 1988.
Dini, "Recognizing death: liver phagocytosis of apoptotic cells," *Eur J Histochem.*, 44(3):217-227, 2000.
Doering et al., "Network analysis reveals centrally connected genes and pathways involved in CD8+ T cell exhaustion versus memory," *Immunity*, 37(6):1130-1144, Epub Nov. 15, 2012.
Dong et al., "B7-H1 determines accumulation and deletion of intrahepatic CD8(+) T lymphocytes," *Immunity.*, 20(3):327-336, Mar. 2004.
Dong et al., "B7-H1 pathway and its role in the evasion of tumor immunity" *J Mol Med (Berl).*, 81(5):281-287, Epub Apr. 30, 2003.
Dong et al., "B7-H1, a third member of the B7 family, co-stimulates T-cell proliferation and interleukin-10 secretion," *Nat Med.*, 5(12):1365-1369, Dec. 1999.
Dong et al., "Immune regulation by novel costimulatory molecules," *Immunol Res.*, 28(1):39-48, 2003.
Dong et al., "Immunoregulatory role of B7-H1 in chronicity of inflammatory responses," *Cell Mol Immunol.*, 3(3):179-187, Jun. 2006.
Dong et al., "Tumor-associated B7-H1 promotes T-cell apoptosis: a potential mechanism of immune evasion," *Nat Med.*, 8(8):793-800, Epub Jun. 24, 2002.
Dragoi et al., "DNA-PKcs, but not TLR9, is required for activation of Akt by CpG-DNA," *EMBO J.*, 24(4):779-789, Epub Jan. 27, 2005.
Dronca et al., "Soluble PD-L1 (sPD-L1) is associated with decreased survival in metastatic melanoma ," Society for Melanoma Research 2015 Congress, San Francisco, CA, Nov. 18-21, 2015 [abstract].
Dudler et al., "Gene transfer of programmed death Ligand-1.1g prolongs cardiac allograft survival," *Transplantation*, 82(12):1733-1737, Dec. 27, 2006.
Dunussi-Joannopoulos et al., "Gene therapy with B7.1 and GM-CSF vaccines in a murine AML model," *J Pediatr Hematol Oncol.*, 19(6):536-540, Nov.-Dec. 1997.
Duraiswamy et al., "Replenish the source within Rescuing tumor-infiltrating lymphocytes by double checkpoint blockade," *Oncol.*, 2:10, e25912, Oct. 2013.
Ehl et al., "Different susceptibility of cytotoxic T cells to CD95 (Fas/Apo-1) ligand-mediated cell death after activation in vitro versus in vivo," *J Immunol.*, 156(7):2357-2360, Apr. 1, 1996.
Elliott et al., "Mitoxantrone in combination with an inhibitor of DNA-dependent protein kinase: a potential therapy for high risk B-cell chronic lymphocytic leukaemia," *Br J Haematol.*, 152(1):61-71, Epub Nov. 18, 2010.

(56) References Cited

OTHER PUBLICATIONS

EMBL-EBI Accession No. AF 142780.2 "Mus musculus butyrophilin-like protein (Btdc) mRNA, complete cds," created Jun. 1, 1999, 2 pages.
EMBL-EBI Accession No. Q9WUL5, "Programmed cell death 1 ligand 2," Nov. 1, 1999, 5 pages.
Engh et al., "Accurate bond and angle parameters for X-ray protein structure refinement," *Acta Cryst.*, A47(4):392-400, Jul. 1, 1991.
Falkner et al., "pUV I: a new vaccinia virus insertion and expression vector," *Nucleic Acids Res.*, 15(17):7192, Sep. 11, 1987.
Farley et al., "p38 mitogen-activated protein kinase mediates the Fas-induced mitochondrial death pathway in CD8+ T cells," *Mol Cell Biol.*, 26(6):2118-2129, Mar. 2006.
Fechteler et al., "Prediction of protein three-dimensional structures in insertion and deletion regions: a procedure for searching data bases of representative protein fragments using geometric scoring criteria," *J Mol Biol.*, 253(1):114-131, Oct. 13, 1995.
Feng et al., "Identification of a PKB/Akt hydrophobic motif Ser-473 kinase as DNA-dependent protein kinase," *J Biol Chem.*, 279(39):41189-41196, Epub Jul. 15, 2004.
Figlin et al., "Treatment of metastatic renal cell carcinoma with nephrectomy, interleukin-2 and cytokine-primed or CD8(+) selected tumor infiltrating lymphocytes from primary tumor," *J Urol.*, 158(3 Pt 1):740-745, Sep. 1997.
Finck et al., "Treatment of Murine Lupus with CTLA41g," *Science*, 265(5176):1225-1227, Aug. 26, 1994.
Fire et al., "Potent and specific genetic interference by double-stranded RNA in Caenorhabditis elegans," *Nature*, 391(6669):806-811, Feb. 19, 1998.
Fleming et al., Selective expression of Ly-6G on myeloid lineage cells in mouse bone marrow. RB6-8C5 mAb to granulocyte-differentiation antigen (Gr-1) detects members of the Ly-6 family, *J Immunol.*, 151(5):2399-2408, Sep. 1, 1993.
Foell et al., "CD137 costimulatory T cell receptor engagement reverses acute disease in lupus-prone NZB×NZW F1 mice," *J Clin Invest.*, 111(10):1505-1518, May 2003.
Foell et al., "CD137-Mediated T Cell Co-Stimulation Terminates Existing Autoimmune Disease in SLE-Prone NZB/NZW F1 Mice," *Ann N Y Acad Sci.*, 987:230-235, Apr. 2003.
Fortugno et al., "Survivin exists in immunochemically distinct subcellular pools and is involved in spindle microtubule function," J Cell Sci., 115(Pt 3):575-585, Feb. 1, 2002.
Frank et al., "An outcome prediction model for patients with clear cell renal cell carcinoma treated with radical nephrectomy based on tumor stage, size, grade and necrosis: the SSIGN score," *J Urol.*, 168(6):2395-2400, Dec. 2002.
Freeman et al., "B7, a new member of the Ig superfamily with unique expression on activated and neoplastic B cells," *J Immunol.*, 143(8):2714-2722, Oct. 15, 1989.
Freeman et al., "Cloning of B7-2: a CTLA-4 counter-receptor that co stimulates human T cell proliferation," *Science*, 262(5135):909-911, Nov. 5, 1993.
Freeman et al., "Engagement of the PD-1 Immunoinhibitory receptor by a novel B7 family member leads to negative regulation of lymphocyte activation," *J Exp Med.*, 192(7):1027-1034, Oct. 2, 2000.
Freeman et al., "Structure, expression, and T cell proliferation costimulatory activity of the murine homologue of the human B lymphocyte activation antigen B7," *J Exp Med.*, 174(3):625-631, Sep. 1, 1991.
Friedmann et al., "Interaction of the epidermal growth factor receptor and the DNA-dependent protein kinase pathway following gefitinib treatment," *Mol Cancer Ther.*, 5(2):209-218, Feb. 2006.
Frigola et al., "Identification of a soluble form of B7-H1 that retains immunosuppressive activity and is associated with aggressive renal cell carcinoma," *Clin Cancer Res.*, 17(7):1915-1923, Apr. 1, 2011.
Fuerst et al., "Transfer of the inducible lac repressor/operator system from *Escherichia coli* to a vaccinia expression vector," *Proc Natl Acad Sci U S A.*, 86(8):2549-2553, Apr. 1989.

Fyfe et al., "Results of treatment of 255 patients with metastatic renal cell carcinoma who received high-dose recombinant interleukin-2 therapy," *J Clin Oncol.*, 13(3):688-696, Mar. 1995.
GenBank Accession No. AAC51660 "apoptosis inhibitor survivin [*Homo sapiens*]," Sep. 2, 2004, 2 pages.
GenBank Accession No. AAP37283, "immune costimulatory protein B7-H4 [*Homo sapiens*]," Jun. 1, 2003, 1 page.
GenBank Accession No. AK001872.1, "*Homo sapiens* cDNA FLJ11010 fis, clone PLACE1003145," Feb. 22, 2000, 2 pages.
GenBank Accession No. AL162253, "Human DNA sequence from clone RP11-574F11 on chromosome 9 contains the gene for B7-H1 protein (PD-L1), the gene for programmed death ligand 2 (PDL2) (PDCD1L2) and a novel gene, complete sequence" Feb. 24, 2008, 35 pages.
GenBank Accession No. AY280972, "*Homo sapiens* immune costimulatory protein B7-H4 mRNA, complete cds," Jun. 1, 2003, 1 page.
GenBank Accession No. NM_005191.3 (GI No. 113722122), "*Homo sapiens* CD80 molecule (CD80), mRNA," Jun. 15, 2013, 5 pages.
GenBank Accession No. NP_005182.1 (GI No. 4885123), "T-lymphocyte activation antigen CD80 precursor [*Homo sapiens*]," Jun. 15, 2013, 3 pages.
GenBank Accession No. U75285 "*Homo sapiens* apoptosis inhibitor survivin gene, complete cds," Sep. 2, 2004, 5 pages.
GenBank® Accession No. AAF25807 (GI No. 6708119), "B7-H1 [*Homo sapiens*]," Jan. 18, 2000, 2 pages.
GenBank® Accession No. AAH74740.1, GI No. 49902307, "Programmed cell death 1 [*Homo sapiens*]," Jul. 15, 2006, 2 pages.
GenBank® Accession No. AAX29153.1, GI No. 60652917, "integrin alpha L, partial [synthetic construct]," Mar. 29, 2005, 2 pages.
GenBank® Accession No. AF177937 (GI No. 6708118), "*Homo sapiens* B7-H1 mRNA, complete cds," Jan. 18, 2000, 1 page.
GenBank® Accession No. BC008777.2, GI No. 33870544, "*Homo sapiens* integrin, alpha L (antigen CD11A (p180), lymphocyte function-associated antigen 1; alpha polypeptide), mRNA (cDNA clone MGC:1714 Image:3142951), complete cds," Jul. 28, 2005, 4 pages.
GenBank® Accession No. BC074740.2, GI No. 50960296, "*Homo sapiens* programmed cell death 1, mRNA (cDNA clone MGC:103817 Image:30915198), complete cds," Jul. 15, 2006, 3 pages.
Gerdes et al. "Cell cycle analysis of a cell proliferation-associated human nuclear antigen defined by the monoclonal antibody Ki-67," *J Immunol.*, 133(4):1710-1715, Oct. 1984.
Gerstmayer et al., "Costimulation of T cell proliferation by a chimeric B7-2 antibody fusion protein specifically targeted to cells expressing the erbB2 proto-oncogene," *J Immunol.*, 158(10):4584-4590, May 5, 1997.
Gerstmayer et al., "Costimulation of T-cell proliferation by a chimeric B7 antibody fusion protein,"*Cancer Immunol Immunother.*, 45(3-4):156-158, Nov.-Dec. 1997.
Gevaert et al., "Protein identification based on matrix assisted laser desorption/ionization-post source decay-mass spectrometry," *Electrophoresis*, 22(9):1645-1651, May 2001.
Ghebeh et al., "Doxorubicin downregulates cell surface B7-H1 expression and upregulates its nuclear expression in breast cancer cells: role of B7-H1 as an anti-apoptotic molecule," *Breast Cancer Res.*, 12(4):R48, Epub Jul. 13, 2010.
Ghebeh et al., "The B7-H1 (PD-L1) T lymphocyte-inhibitory molecule is expressed in breast cancer patients with infiltrating ductal carcinoma: correlation with important high risk prognostic factors," *Neoplasia*, 8(3):190-198, Mar. 2006.
Gibbons et al., "B7-H1 limits the entry of effector CD8(+) T cells to the memory pool by upregulating Bim," Oncoimmunology, 1(7):1061-1073, Oct. 1, 2012.
Gillings et al., "Apoptosis and autophagy: BIM as a mediator of tumour cell death in response to oncogene-targeted therapeutics," *FEBS J.*, 276(21):6050-6062, Epub Sep. 29, 2009.
Gimmi et al., "B-cell surface antigen B7 provides a costimulatory signal that induces T cells to proliferate and secrete interleukin 2," *Proc Natl Acad Sci U S A.*, 88(9):3671-3675, May 1, 1991.
Goodwin et al., "Molecular cloning and expression of the type 1 and type 2 murine receptors for tumor necrosis factor," *Mol Cell Biol.*, 11(6):3020-3026, Jun. 1991.

(56) References Cited

OTHER PUBLICATIONS

Goodwin et al., "Molecular cloning of a ligand for the inducible T cell gene 4-1BB: a member of an emerging family of cytokines with homology to tumor necrosis factor," *Eur J Immunol.*, 23(10):2631-2641, Oct. 1993.
Green et al., "Activation-induced cell death in T cells," *Immunol Rev.*, 193:70-81, Jun. 2003.
Green et al., "Antigen-specific human monoclonal antibodies from mice engineered with human Ig heavy and light chain YACs," *Nat Genet.*, 7(1):13-21, May 1994.
Greenwald et al., "The B7 family revisited," *Annu Rev Immunol.*, 23:515-548, 2005.
Grivennikov et al. "Immunity, inflammation, and cancer," *Cell.*, 140(6):883-899, Mar. 19, 2010.
Guatelli et al., "Isothermal, in vitro amplification of nucleic acids by a multi enzyme reaction modeled after retroviral replication," *Proc Natl Acad Sci U S A.*, 87(5):1874-1878, Mar. 1990.
Guinn et al., "4-1BBL cooperates with B7-1 and B7-2 in converting a B cell lymphoma cell line into a long-lasting antitumor vaccine," *J Immunol.*, 162(8):5003-5010, Apr. 15, 1999.
Gunn et al., "Correct end use during end joining of multiple chromosomal double strand breaks is influenced by repair protein RAD50, DNA-dependent protein kinase DNA-PKcs, and transcription context," *J Biol Chem.*, 286(49):42470-42482, Epub Oct. 24, 2011.
Guo et al., "A novel fusion protein of IPI O-scFv retains antibody specificity and chemokine function," *Biochem Biophys Res Commun.*, 320(2):506-513, Jul. 23, 2004.
Haendeler et al., "Nitric Oxide and Apoptosis," *Vitam Horm.*, 57:49-77, 1999.
Hansen et al., "Monoclonal antibodies identifying a novel T-cell antigen and Ia antigens of human lymphocytes," *Immunogenetics*, 10(1-4):247-260, Feb. 1, 1980.
Harlow and Lane., "Antibodies: A Laboratory Manual," Cold Spring Harbor Laboratory Press, Cold Spring Harbor, NY, pp. 553, 555-582, 584-589, 591-612, 1988.
Harrington et al., "Differentiating between memory and effector CD8 T cells by altered expression of cell surface O-glycans," *J Exp Med.*, 191(7):1241-1246, Apr. 3, 2000.
Hatzoglou et al., "Hepatic gene transfer in animals using retroviruses containing the promoter from the gene for phosphoenolpyruvate carboxykinase" *J Biol Chem.*, 265(28):17285-17293, Oct. 5, 1990.
Hawiger et al., "Dendritic cells induce peripheral T cell unresponsiveness under steady state conditions in vivo," *J Exp Med.*, 194(6):769-779, Sep. 17, 2001.
Hayakawa et al., "Inhibition of BAD phosphorylation either at serine 112 via extracellular signal-regulated protein kinase cascade or at serine 136 via Akt cascade sensitizes human ovarian cancer cells to cisplatin," *Cancer Res.*, 60(21):5988-5994, Nov. 1, 2000.
He et al., "Identification of a novel splice variant of human PD-L1 mRNA encoding an isoform-lacking-Igv-like domain," *Acta Pharmacol Sin.*, 26(4):462-468, Apr. 2005.
Hellstrom et al., "T cell immunity to tumor antigens," *Crit Rev Immunol.*, 18(1-2):1-6, 1998.
Henry et al., "Cloning, structural analysis, and mapping of the B30 and B7 multigenic families to the major histocompatibility complex (MHC) and other chromosomal regions," *Immunogenetics*, 46(5):383-395, 1997.
Henry et al., "Structure and evolution of the extended B7 family," *Immunol Today*, 20(6):285-288, Jun. 1999.
Hentikoff, "Amino acid substitution matrices from protein blocks," *Proc Natl Acad Sci U S A.*, 89(22):10915-10919, Nov. 15, 1992.
Hestdal et al., "Characterization and regulation of RB6-8C5 antigen expression on murine bone marrow cells," *J Immunol.*, 147(1):22-28, Jul. 1, 1991.
Hildeman et al., "Activated T cell death in vivo mediated by proapoptotic bcl-2 family member bim," *Immunity*, 16(6):759-767, Jun. 2002.
Hirano et al., "Blockade of B7-H1 and PD-1 by monoclonal antibodies potentiates cancer therapeutic immunity," *Cancer Res.*, 65(3):1089-1096, Feb. 1, 2005.
Hiroishi et al., "Interferon-alpha gene therapy in combination with CDS0 transduction reduces tumorigenicity and growth of established tumor in poorly immunogenic tumor models," *Gene Ther.*, 6(12):1988-1994, Dec. 1999.
Hochman et al., "An active antibody fragment (Fv) composed of the variable portions of heavy and light chains," *Biochemistry*, 12(6):1130-1135, Mar. 13, 1973.
Hock et al., "Retrovirus-mediated transfer and expression of drug resistance genes in human haematopoietic progenitor cells," *Nature*, 320:275-277, 1986.
Hoffman, "T Cells in the Pathogenesis of Systemic Lupus Erythematosus," *Front Biosci.*, 6:D1369-D1378, Oct. 1, 2001.
Hoiseth et al., "Aromatic-dependent *Salmonella typhimurium* are non-virulent and effective as live vaccines," *Nature*, 291(5812):238-239, May 21, 1981.
Hollinger et al., "Diabodies: small bivalent and bispecific antibody fragments," *Proc Natl Acad Sci U S A.*, 90(14):6444-6448, Jul. 15, 1993.
Holt et al., "Domain antibodies: proteins for therapy," *Trends Biotechnol.*, 21(11):484-490, Nov. 2003.
Hori et al., "B7-H1-induced apoptosis as a mechanism of immune privilege of corneal allografts," *J Immunol.*, 177(9):5928-5935, Nov. 1, 2006.
Huai et al., "Inducible gene expression with the Tet-on system in CD4+ T cells and thymocytes of mice," *Genesis*, 45(7):427-431, Jul. 2007.
Huang et al., "The liver eliminates T cells undergoing antigen-triggered apoptosis in vivo," *Immunity*, 1(9):741-749, Dec. 31, 1994.
Huang, "Structural chemistry and therapeutic intervention of protein-protein interactions in immune response, human immunodeficiency virus entry, and apoptosis," *Pharmacol Ther.*, 86(3):201-215, Jun. 2000.
Hubbard et al., "Anti-neutrophil-elastase defenses of the lower respiratory tract in alpha 1-antitrypsin deficiency directly augmented with an aerosol of alpha I-antitrypsin," *Ann Intern Med.*, 111(3):206-212, Aug. 1, 1989.
Hunter, "Diabetes in pregnancy," Effective Care in Pregnancy and Childbirth, Chalmers et al. (eds.), Oxford University Press, vol. 1, pp. 578-593, 1989.
Huse et al., "Generation of a large combinatorial library of the immunoglobulin repertoire in phage lambda," *Science*, 246(4935):1275-1281, Dec. 8, 1989.
Huston et al., "Protein engineering of antibody binding sites: recovery of specific activity in an anti-digoxin single-chain Fv analogue produced in *Escherichia coli*," *Proc Natl Acad Sci U S A.*, 85(16):5879-5883, Aug. 1988.
Hutloff et al., "ICOS is an inducible T-cell co-stimulator structurally and functionally related to CD28," *Nature*, 397(6716):263-266, Jan. 21, 1999.
Hyrup et al., "Peptide nucleic acids (PNA): synthesis, properties and potential applications," *Bioorg Med Chem.*, 4(1):5-23, Jan. 31, 1996.
Ichikawa and Chen, "Role of B7-H1 and B7-H4 molecules in down-regulating effector phase of T-cell immunity: novel cancer escaping mechanisms," *Front Biosci.*, 10:2856-2860, Sep. 1, 2005.
Ikemizu et al., "Structure and dimerization of a soluble form of B7-1," *Immunity*, 12(1):51-60, Jan. 2000.
Ikonomidis, "Delivery of a viral antigen to the class I processing and presentation pathway by Listeria monocytogenes," *J Exp Med.*, 180(6):2209-2218, Dec. 1, 1994.
Inman et al. "PD-L1 (B7-H1) expression by urothelial carcinoma of the bladder and BCG-induced granulomata: associations with localized stage progression," *Cancer*, 109(8):1499-1505, Apr. 15, 2007.
Inman et al., "Questionable relevance of gamma delta T lymphocytes in renal cell carcinoma," *J Immunol.*, 180(5):3578-3584, Mar. 1, 2008.
Ishida et al., "Differential expression of PD-L1 and PD-L2, ligands for an inhibitory receptor PD-1, in the cells of lymphohematopoietic tissues," *Immunol Lett.*, 84(1):57-62, Oct. 21, 2002.

(56) References Cited

OTHER PUBLICATIONS

Ishida et al., "Induced expression of PD-1, a novel member of the immunoglobulin gene superfamily, upon programmed cell death," *EMBO J.*, 11(11):3887-3895, Nov. 1992.

Iwai et al., "Involvement of PD-L1 on tumor cells in the escape from host immune system and tumor immunotherapy by PD-L1 blockade," Proc Natl Acad Sci U S A., 99(19):12293-12297, Epub Sep. 6, 2002.

Iwai et al., "PD-1 inhibits antiviral immunity at the effector phase in the liver," *J Exp Med.*, 198(1):39-50, Jul. 7, 2003.

Jacinto et al., "SIN1/MIP1 maintains rictor-mTOR complex integrity and regulates Akt phosphorylation and substrate specificity," *Cell*, 127(1):125-137, Epub. Sep. 7, 2006.

Jacobson et al., "Unique site of IgG2a and rheumatoid factor production in MRL/lpr mice," *Immunol Rev.*, 156:103-110, Apr. 1997.

Janeway et al., "The immunogenicity of a protein depends on its presentation to T cells," in *Immunobiology: The Immune System in Health and Disease*, Elsevier Science., 4:36, 1999.

Jayaraman, "Flow cytometric determination of mitochondrial membrane potential changes during apoptosis of T lymphocytic and pancreatic beta cell lines: comparison of tetramethylrhodamineethylester (TMRE), chloromethyl-X-rosamine (H2-CMX-Ros) and MitoTracker Red 580 (MTR580)," *J Immunol Methods.*, 306(1-2):68-79, Epub Sep. 29, 2005.

Jeannin et al., "Soluble CD86 is a costimulatory molecule for human T lymphocytes," *Immunity*, 13(3):303-312, Sep. 2000.

Jemal et al., "Cancer Statistics, 2005," *CA Cancer J Clin*, 55(1):10-30, Jan.-Feb. 2005.

Jerne, "Towards a network theory of the immune system," *Ann Immunol* (Paris)., 125C(1-2):373-389, Jan. 1974.

Jiang et al., "Genome-wide association study for biomarker identification of Rapamycin and Everolimus using a lymphoblastoid cell line system," *Front Genet.*, 4:166, Aug. 30, 2013.

Johnston et al., "Biolistic transformation of animal tissue," *In Vitro Cell Dev Biol Anim.*, 27P: 11-14 (1991).

Jones et al., "Replacing the complementarity-determining regions in a human antibody with those from a mouse," *Nature*, 321(6069):522-525, May 29-Jun. 4, 1986.

Kabat et al., Sequences of Proteins of Immunological Interest, Fifth Edition, U.S. Department of Health and Human Services, NIH Publication No. 91-3242, Table of Contents, 20 pages, 1991.

Kaleko et al., "Persistent gene expression after retroviral gene transfer into liver cells in vivo," *Hum Gene Ther.*, 2(1):27-32, Spring 1991.

Kaliyaperumal et al., "Antigen-specific therapy of murine lupus nephritis using nucleosomal peptides: tolerance spreading impairs pathogenic function of autoimmune T and B cells," *J Immunol.*, 162(10):5775-5783, May 15, 1999.

Kalled et al., "Anti-CD40 ligand antibody treatment of SNF1 mice with established nephritis: preservation of kidney function," *J Immunol.*, 160(5):2158-2165, Mar. 1, 1998.

Kanai et al., "Blockade of B7-H1 suppresses the development of chronic intestinal inflammation," *J Immunol.*, 171(8):4156-4163, Oct. 15, 2003.

Kaneko et al., "Augmentation of Va14 NKT cell-mediated cytotoxicity by interleukin 4 in an autocrine mechanism resulting in the development of concanavalin A-induced hepatitis," *J Exp Med.*, 191(1):105-114, Jan. 3, 2000.

Karakhanova et al., "ERK/p38 MAP-kinases and PI3K are involved in the differential regulation of B7-H1 expression in DC subsets," *Eur J Immunol.*, 40(1):254-266, Jan. 2010.

Kataoka et al., "Flow cytometric analysis of phosphoiylated histone H2AX following exposure to ionizing radiation in human microvascular endothelial cells," *J Radiat Res.*, 47(3-4):245-257, Epub Sep. 2006.

Katou et al., "Differing phenotypes between intraepithelial and stromal lymphocytes in early-stage tongue cancer," *Cancer Res.*, 67(23):11195-11201, Dec. 1, 2007.

Kaufman et al., "A phase I trial of intra lesional RV-B7.1 vaccine in the treatment of malignant melanoma," *Hum Gene Ther.*, 11(7):1065-1082, May 1, 2000.

Kawabe et al., "Programmed cell death and extrathymic reduction of Vβ8+ CD4+ T cells in mice tolerant to Staphylococcus aureus enterotoxin B," *Nature*, 349(6306):245-248, Jan. 17, 1991.

Keir et al., "PD-1 and its ligands in tolerance and immunity," *Annu Rev Immunol.*, 26:677-704, 2008.

Kelley et al., "Cytokines in the Pathogenesis of Systemic Lupus Erythematosus," *Semin Nephrol.*, 19(1):57-66, Jan. 1999.

Kennerdell et al., "Use of dsRNA-mediated genetic interference to demonstrate that frizzled and frizzled 2 act in the wingless pathway," *Cell*, 95(7):1017-1026, Dec. 23, 1998.

Kharbanda et al., "Translocation of SAPK/JNK to mitochondria and interaction with Bcl-x(L) in response to DNA damage," *J Biol Chem.*, 275(1):322-327, Jan. 7, 2000.

Kiessling et al., "High-throughput mutation profiling of CTCL samples reveals KRAS and NRAS mutations sensitizing tumors toward inhibition of the RAS/RAF/MEK signaling cascade," *Blood*, 117(8):2433-2440, Epub Jan. 5, 2011.

Kim et al., "Features of responding T cells in cancer and chronic infection," *Curr Opin Immunol.*, 22(2):223-230, Epub Mar. 6, 2010.

Kim et al., "Therapeutic potential of 4-1BB (CD137) as a regulator for effector CD8(+) T cells," *J Hematother Stem Cell Res.*, 10(4):441-449, Aug. 2001.

Köhler et al., "Continuous cultures of fused cells secreting antibody of predefined specificity," *Nature*, 256(5517):495-497, Aug. 7, 1975.

Kohn et al. "Gene therapy for genetic diseases," *Cancer Invest.*, 7(2):179-192, 1989.

Konieczny et al., "The combination of IgM subunits and proteolytic IgG fragment by controlled formation of interchain disulphides," *Haematologia (Budap).*, 14(1):95-99, 1981.

Korkola et al, "Gene expression-based classification of nonseminomatous male germ cell tumors," *Oncogene*, 24(32):5101-5107, Jul. 28, 2005.

Kosari et al, "Clear cell renal cell carcinoma: gene expression analyses identify a potential signature for tumor aggressiveness," *Clin Cancer Res.*, 11(14):5128-5139, Jul. 15, 2005.

Kozbor et al. "The production of monoclonal antibodies from human hymphocytes,"Immunology Today, 4(3):72-79, Mar. 1, 1983.

Krempski et al., "Tumor-infiltrating programmed death receptor-1+ dendritic cells mediate immune suppression in ovarian cancer," *J Immunol.*, 186(12):6905-6913, Epub May 6, 2011.

Kruege et al., "The role of CD95 in the regulation of peripheral T-cell apoptosis," *Immunol Rev.*, 193:58-69, Jun. 2003.

Krummel et al., "CTLA-4 engagement inhibits IL-2 accumulation and cell cycle progression upon activation of resting T cells," *J Exp Med.*, 183(6):2533-2540, Jun. 1, 1996.

Kuiper et al., "B7.1 and Cytokines: Synergy 390, 2000 in cancer gene therapy," *Adv Exp Med Biol.*, 465:381-390, 2000.

Kusmartsev et al., "Gr-1+ myeloid cells derived from tumor-bearing mice inhibit primary T cell activation induced through CD3/CD28 costimulation," *J Immunol.*, 165(2):779-785, Jul. 15, 2000.

Kwon et al., "4-1BB: Still in the Midst of Darkness," *Mol Cells.*, 10(2):119-126, Apr. 30, 2000.

LaBaer, "So, you want to look for biomarkers (introduction to the special biomarkers issue)," *J Proteome Res.*, 4(4):1053-1059, Jul.-Aug. 2005.

Larrubia et al., "Bim-mediated apoptosis and PD-1/PD-L1 pathway impair reactivity of PD1(+)/CD127(−) HCV-specific CD8(+) cells targeting the virus in chronic hepatitis C virus infection," *Cell Immunol.*, 269(2):104-114, Epub Mar. 17, 2011.

Latchman et al., "PD-L2 is a second ligand for PD-1 and inhibits T cell activation," *Nat Immunol.*, 2(3):261-268, Mar. 2001.

Lawson et al., "Treatment of murine lupus with cDNA encoding IFN-gammaR/Fc," *J Clin Invest.*, 106(2):207-215, Jul. 2000.

Lazarevic and Glimcher, "T-bet in disease," *Nat Immunol.*, 12(7):597-606, Jun. 20, 2011.

Lee et al., "Survivin expression and its clinical significance in pancreatic cancer," *BMC Cancer*, 5:127, Oct. 4, 2005.

Lee et al., "Increased vaccine-specific T cell frequency after peptide-based vaccination correlates with increased susceptibility to in vitro

(56) References Cited

OTHER PUBLICATIONS stimulation but does not lead to tumor regression," *J Immunol.*, 163(11):6292-6300, Dec. 1, 1999.

Leibovich et al., "Prediction of progression after radical nephrectomy for patients with clear cell renal cell carcinoma: a stratification tool for prospective clinical trials," *Cancer*, 97(7):1663-1671, Apr. 1, 2003.

Lenardo et al., "Mature T lymphocyte apoptosis—immune regulation in a dynamic and unpredictable antigenic environment," *Annu Rev Immunol.*, 17:221-253, 1999.

Lenschow et al., "CD28/B7 system of T cell costimulation," *Annu Rev Immunol.*, 14:233-258, 1996.

Levitt, "Accurate modeling of protein conformation by automatic segment matching," *J Mol Biol.*, 226(2):507-533, Jul. 20, 1992.

Lewinski, et al., Retroviral DNA integration: viral and cellular determinants of target-site selection, *PLoS Pathog.*, 2(6):e60, Epub Jun. 23, 2006.

Lewis et al., "Surrogate tumor antigen vaccination induces tumor-specific immunity and the rejection of spontaneous metastases," *Cancer Res.*, 65(7):2938-2946, Apr. 1, 2005.

Lewis, "PCR's Competitors Are Alive and Well and Moving Rapidly Towards Commercialization," *Genetic Engineering News*, vol. 12, 3 pages, 1992.

Li et al., "Anti-programmed death-1 synergizes with granulocyte macrophage colony-stimulating factor—secreting tumor cell immunotherapy providing therapeutic benefit to mice with established tumors," *Clin Cancer Res.*, 15(5):1623-1634, Epub Feb. 10, 2009.

Li et al., "Gemcitabine and arabinosylcytosin pharmacogenomics: genome-wide association and drug response biomarkers," *PLoS One.*, 4(11):e7765, Nov. 9, 2009.

Liang et al., "Autoantibody responses and pathology regulated by B7-1 and B7-2 costimulation in MRL/lpr lupus," *J Immunol.*, 165(6):3436-3443, Sep. 15, 2000.

Linsley et al., "Binding of the B cell activation antigen B7 to CD28 costimulates T cell proliferation and interleukin 2 mRNA accumulation" *J Exp Med.*, 173(3):721-730, Mar. 1, 1991.

Linsley et al., "Extending the B7 (CD80) gene family," *Protein Sci.*, 3(8):1341-1343, Aug. 1994.

Linsley et al., "T-cell antigen CD28 mediates adhesion with B cells by interacting with activation antigen 87188-1," *Proc Natl Acad Sci U S A.*, 87(13):5031-5035, Jul. 1990.

Liu et al., "B7DC/PDL2 promotes tumor immunity by a PD-1-independent mechanism," *J Exp Med.*, 197(12):1721-1730, Jun. 16, 2003.

Liu et al., "B7-H3 silencing increases paclitaxel sensitivity by abrogating Jak2/Stat3 phosphorylation," *Mol Cancer Ther.*, 10(6):960-971, Epub Apr. 25, 2011.

Liu et al., "Endogenous tumor-reactive CD8+ T cells are differentiated effector cells expressing high levels of CD11a and PD-1 but are unable to control tumor growth," *Oncoimmunology.*, 2(6):e23972, Epub Jun. 6, 2013.

Liu et al., "Fas-mediated apoptosis causes elimination of virus-specific cytotoxic T cells in the virus-infected liver," *J Immunol.*, 166(5):3035-3041, Mar. 1, 2001.

Liu et al., "Plasma cells from multiple myeloma patients express B7-H1 (PD-L1) and increase expression after stimulation with IFN-{gamma} and TLR ligands via a MyD88-, TRAF6-, and MEK-dependent pathway," *Blood*, 110(1):296-304, Epub Mar. 15, 2007.

Lonberg et al., "Antigen-specific human antibodies from mice comprising four distinct genetic modifications," *Nature*, 368(6474):856-859, Apr. 28, 1994.

Losman et al., "Baboon anti-idiotype antibodies mimic a carcinoembryonic antigen epitope," *Int J Cancer.*, 46(2):310-314, Aug. 15, 1990.

Lu et al., "EGF-IL-18 fusion protein as a potential anti-tumor reagent by induction of immune response and apoptosis in cancer cells," *Cancer Lett.*, 260(1-2):187-197, Epub Dec. 21, 2007.

Luciano et al., "Phosphorylation of Bim-EL by Erk1/2 on serine 69 promotes its degradation via the proteasome pathway and regulates its proapoptotic function," *Oncogene.*, 22(43):6785-6793, Oct. 2, 2003.

Luettig et al., "Naive and memory T lymphocytes migrate in comparable numbers through normal rat liver: activated T cells accumulate in the periportal field," *J Immunol.*, 163(8):4300-4307, Oct. 15, 1999.

Lunsford et al., "Targeting LFA-1 and cd154 suppresses the in vivo activation and development of cytolytic (cd4-Independent) CD8+ T cells," *J Immunol.*, 175(12):7855-7866, Dec. 15, 2005.

Ma et al., "The DNA-dependent protein kinase catalytic subunit phosphorylation sites in human Artemis," *J Biol Chem.*, 280(40):33839-33846, Epub Aug. 10, 2005.

Ma et al., "The Role of PD-1 Ligand in Immune Evasion by Breast Cancer," Dana-Farber Cancer Institute Annual Summary Report May 1, 2002-Apr. 30, 2005, pp. 5-6, 9, 11, report date: May 2005.

Mah et al., "gammaH2AX: a sensitive molecular marker of DNA damage and repair," *Leukemia*, 24(4):679-686, Epub Feb. 4, 2010.

Mahotka et al., "Distinct in vivo expression patterns of survivin splice variants in renal cell carcinomas," *Int J Cancer*, 100(1):30-36, Jul. 1, 2002.

Mann et al., "Construction of a retrovirus packaging mutant and its use to produce helper-free defective retrovirus" *Cell*, 33(1):153-159, May 1983.

Martin et al. "Combination gene therapy with CD86 and the MHC Class II transactivator in the control of lung tumor growth," *J Immunol.*, 162(11):6663-6670, Jun. 1, 1999.

Mathiowitz et al., "Morphology of poly anhydride microsphere delivery systems," *Scanning Microsc.*, 4(2):329-340, Jun. 1990.

Mathiowitz et al., "Polyanhydride microspheres as drug carriers. I. Hot-melt microencapsulation," *J. Controlled Release*, 5(1):13-22, Jun. 1, 1987.

Mathiowitz et al., "Polyanhydride microspheres. IV. Morphology and characterization of systems made by spray drying," *J. Annl. Polymer Sci.* 45(1): 125-134, May 5, 1992.

Mathiowitz, Novel microcapsules for delivery systems, *Reactive Polymers*, 6(2):275-283, Oct. 31, 1987.

Mathiowitz, "Polyanhydride microspheres as drug carriers, II. Microencapsulation by solvent removal," *J. Appl. Polymer Sci.*, 35(3): 755-774, Feb. 20, 1988.

Mayo Clinic, "Mayo Clinic Discovers Potential Marker for Aggressive Kidney Cancer," Science Daily, Retrieved from the Internet: <URL: https://www.sciencedaily.com/releases/2004/11/041130200858.htm>, 2 pages, Dec. 9, 2004.

McCubrey et al., "Roles of the Raf/MEK/ERK pathway in cell growth, malignant transformation and drug resistance," *Biochim Biophys Acta.*, 1773(8):1263-1284, Epub Oct. 7, 2006.

McDermott et al., "PD-1 as a potential target in cancer therapy," *Cancer Med.*, 2(5):662-673. Epub Jul. 21, 2013.

McLachlin et al., "Retroviral-mediated gene transfer," *Prog Nucleic Acid Res Mol Biol.*, 38:91-135, 1990.

Mehal et al., "Antigen presentation by liver cells controls intrahepatic T cell trapping, whereas bone marrow-derived cells preferentially promote intrahepatic T cell apoptosis," *J Immunol.*, 167(2):667-673, Jul. 15, 2001.

Mehal et al., "TCR ligation on CD8+ T cells creates double-negative cells in vivo," *J Immunol.*, 161(4):1686-1693, Aug. 15, 1998.

Melero et al., "Amplification of tumor immunity by gene transfer of the co-stimulatory 4-1BB ligand: synergy with the CD28 co-stimulatory pathway," *Eur J Immunol.*, 28(3):1116-1121, Mar. 1998.

Melero et al., "Monoclonal antibodies against the 4-1BB T-cell activation molecule eradicate established tumors," *Nat Med.*, 3(6):682-685, Jun. 1997.

Melero et al., "NK1.1 cells express 4-1BB (CDw137) costimulatory molecule and are required for tumor immunity elicited by anti-4-1BB monoclonal antibodies," *Cell Immunol.*, 190(2):167-172, Dec. 15, 1998.

Melief et al., "Strategies for immunotherapy of cancer," *Advances in immunology*, 75:235-282, Jan. 1, 2000.

(56) References Cited

OTHER PUBLICATIONS

Mendez-Fernandez et al., "Clearance of Theiler's virus infection depends on the ability to generate a CD8+ T cell response against a single immunodominant viral peptide," *Eur J Immunol.*, 33(9):2501-2510, Sep. 2003.
Merrill, "Emergence of targeted immune therapies for systemic lupus," *Expert Opin Emerg Drugs*, 10(1):53-65, Feb. 2005.
Merritt et al., "Activation of p38 mitogen-activated protein kinase in vivo selectively induces apoptosis of CD8(+) but not CD4(+) T cells," *Mol Cell Biol.*, 20(3):936-946, Feb. 2000.
Metzler et al., "Solution structure of human CTLA-4 and delineation of a CD80/CD86 binding site conserved in CD28," *Nat Struct Biol.*, 4(7):527-531, Jul. 1997.
Miller et al., "Gene transfer by retrovirus vectors occurs only in cells that are actively replicating at the time of infection," *Mol Cell Biol.*, 10(8):4239-4242, Aug. 1990.
Miller et al., "Generation of helper-free amphotropic retroviruses that transduce a dominant-acting, methotrexate-resistant dihydrofolate reductase gene," *Mol Cell Biol.*, 5(3):431-437, Mar. 1985.
Miller et al., "Redesign of retrovirus packaging cell lines to avoid recombination leading to helper virus production," *Mol Cell Biol.*, 6(8):2895-2902, Aug. 1986.
Miller, "Human gene therapy comes of age," *Nature*, 357(6378):455-460, Jun. 11, 1992.
Misquitta et al., "Targeted disruption of gene function in *Drosophila* by RNA interference (RNA-i): A role for nautilus in embryonic somatic muscle formation," *Proc Natl Acad Sci U S A.*, 96(4):1451-1456, Feb. 16, 1999.
Mizuhara et al., "T cell activation-associated hepatic injury: mediation by tumor necrosis factors and protection by interleukin 6," *J Exp Med.*, 179(5):1529-1537, May 1, 1994.
Mohan et al., "Interaction between CD40 and its ligand gp39 in the development of murine lupus nephritis," *J Immunol.*, 154(3):1470-1480, Feb. 1, 1995.
Montesano et al, "Genetic alterations in esophageal cancer and their relevance to etiology and pathogenesis: a review," *Int J Cancer.*, 69(3):225-235, Jun. 21, 1996.
Morrison et al., "Chimeric human antibody molecules: mouse antigen-binding domains with human constant region domains," *Proc Natl Acad Sci U S A.*, 81(21):6851-6855, Nov. 1984.
Morse et al., "Abnormalities induced by the mutant gene Ipr: expansion of a unique lymphocyte subset," *J Immunol.*, 129(6):2612-2615, Dec. 1982.
Moss, "Poxvirus expression vectors," *Curr Top Microbiol Immunol.*, 158:25-38, 1992.
Moss, "Poxvirus vectors: cytoplasmic expression of transferred genes," *Curr Opin Genet Dev.*, 3(1):86-90, Feb. 1993.
Moss, "Use of vaccinia virus as an infectious molecular cloning and expression vector," *Gene Amglif Anal.*, 3:201-213, 1983.
Moss, "Vaccinia virus vectors," Biotechnology, 20:345-362, 1992.
Moss, "Vaccinia Virus: a tool for research and vaccine development," *Science*, 252(5013):1662-1667, Jun. 21, 1991.
Motzer et al., "Renal Cell Carcinoma," *N Engl J Med.*, 335(12):865-75, Sep. 19, 1996.
Mukheijee et al., "DNA-PK phosphorylates histone H2AX during apoptotic DNA fragmentation in mammalian cells," *DNA Repair (Amst).*, 5(5):575-590, Epub Mar. 29, 2006.
Mumprecht et al., "Programmed death 1 signaling on chronic myeloid leukemia-specific T cells results in T-cell exhaustion and disease progression," *Blood.*, 114(8):1528-1536. Epub May 6, 2009.
Muyldermans, "Single domain camel antibodies: current status," *J Biotechnol.*, 74(4):277-302, Jun. 2001.
Nabel et al., "Recombinant gene expression in vivo within endothelial cells of the arterial wall," *Science*, 244(4910):1342-1344, Jun. 16, 1989.
National Cancer Institute, "Fact Sheet: Tumor Markers," cancer.gov [online] Dec. 7, 2011 [retrieved on Apr. 3, 2014]. Retrieved from the Internet: <URL: http://www.cancer.gov/cancertopics/factsheet/detection/tumor-markers/print>, 8 pages.

Nava-Parada et al., "Peptide vaccine given with a Toll-like receptor agonist is effective for the treatment and prevention of spontaneous breast tumors," *Cancer Res*, 67(3): 1326-1334, Feb. 1, 2007.
Nechiporuk et al., "The mouse SCA2 gene: cDNA sequence, alternative splicing and protein expression," *Hum Mol Genet.*, 7(8):1301-1309, Aug. 1998.
Needleman et al., "A general method applicable to the Search for similarities in the amino acid sequence of two proteins," *J Mol Biol.*, 48(3):443-453, Mar. 1970.
Nelson et al., "Tumor progression despite efficient tumor antigen cross-presentation and effective "arming" of tumor antigen-specific CTL," *J Immunol.*, 166(9):5557-5566, May 1, 2001.
Neves et al., "Surgical treatment of renal cancer with vena cava extension," *Br J Urol.*, 59(5):390-395, May 1987.
Newmark et al., "Preparation and properties of adducts of streptokinase and streptokinase-plasmin complex with poly ethylene glycol and pluronic polyol F38," *J Appl Biochem.*, 4:185-189, 1982.
Nicolau et al., "In vivo expression of rat insulin after intravenous administration of the liposome-entrapped gene for rat insulin I," *Proc Natl Acad Sci U S A.*, 80(4):1068-1072, Feb. 1983.
Nielsen et al., "Melanoma vaccines: the paradox of T cell activation without clinical response," *Cancer Chemother Pharmacol.*, 46 Suppl:S62-S66, 2000.
Nielsen et al., "Peptide nucleic acid (PNA). A DNA mimic with a peptide backbone," *Bioconjug Chem.*, 5(1):3-7, Jan.-Feb. 1994.
Nielsen et al., "Sequence-selective recognition of DNA by strand displacement with a thymine-substituted polyamide," *Science*, 254(5037):1497-1500, Dec. 6, 1991.
Nishimura et al., "Autoimmune dilated cardiomyopathy in PD-1 receptor-deficient mice," *Science*, 291(5502):319-322, Jan. 12, 2001.
Nishimura et al., "Development of lupus-like autoimmune diseases by disruption of the PD-1 gene encoding an ITIM motif-carrying immunoreceptor," *Immunity*, 11(2):141-151, Aug. 1999.
Nishimura et al., "Immunological studies on PD-1-deficient mice: implication of PD-1 as a negative regulator for B cell responses," *Int Immunol.*, 10(10):1563-1572, Oct. 1998.
Nisonhoff et al., "Separation of univalent fragments from the bivalent rabbit antibody molecule by reduction of disulfide bonds," *Arch Biochem Biophys.*, 89:230-244, Aug. 1960.
Ohigashi et al., "Clinical significance of programmed death-1 ligand-1 and programmed death-1 ligand-2 expression in human esophageal cancer," *Clin Cancer Res.*, 11(8):2947-2953, Apr. 15, 2005.
Okazaki et al., "PD-1 and PD-1 ligands from discovery to clinical application," *Int Immunol.*, 19(7):813-824, Epub Jul. 2, 2007.
Opferman al., "Linear differentiation of cytotoxic effectors into memory T lymphocytes," *Science*, 283(5408):1745-1748, Mar. 12, 1999.
O'Reilly et al., "MEK/ERK-mediated phosphorylation of Bim is required to ensure survival of T and B lymphocytes during mitogenic stimulation," *J Immunol.*, 183(1):261-269, Jul. 1, 2009.
Orlandi et al., "Cloning immunoglobulin variable domains for expression by the polymerase chain reaction," *Proc Natl Acad Sci U S A.*, 86(10):3833-3837, May 1989.
Ostrov et al., "Structure of murine CTLA-4 and its role in modulating T cell responsiveness," *Science*, 290(5492):816-819, Oct. 27, 2000.
Ozkaynak et al., "Programmed death-1 targeting can promote allograft survival," *J Immunol.*, 169(11):6546-6553, Dec. 1, 2002.
Panta et al., "ATM and the catalytic subunit of DNA-dependent protein kinase activate NF-kappaB through a common MEK/extracellular signal-regulated kinase/p90(rsk) signaling pathway in response to distinct forms of DNA damage," *Mol Cell Biol.*, 24(5):1823-1835, Mar. 2004.
Pantuck et al., "The changing natural history of renal cell carcinoma," *J Urol.*, 166(5):1611-1623, Nov. 2001.
Pardoll, "Spinning molecular immunology into successful immunotherapy," *Nat Rev Immunol.*, 2(4):227-238, Apr. 2002.
Park et al., "B7-H1/CD80 interaction is required for the induction and maintenance of peripheral T-cell tolerance," *Blood.*, 116(8):1291-1298, Epub May 14, 2010.
Parker et al., "Potential utility of uroplakin III, thrombomodulin, high molecular weight cytokeratin, and cytokeratin 20 in noninva-

(56) References Cited

OTHER PUBLICATIONS sive, invasive, and metastatic urothelial (transitional cell) carcinomas," *Am J Surg Pathol.*, 27(1):1-10, Jan. 2003.
Parsa et al., "Loss of tumor suppressor PTEN function increases B7-H1 expression and immunoresistance in glioma," *Nat Med.*, 13(1):84-88, Epub Dec. 10, 2006.
Paterson et al., "The PD-L1:B7-1 pathway restrains diabetogenic effector T cells in vivo," *J Immunol.*, 187(3):1097-1105, Aug. 1, 2011.
Patsoukis et al., "Selective effects of PD-1 on Akt and Ras pathways regulate molecular components of the cell cycle and inhibit T cell proliferation," *Sci Signal.*, 5(230):ra46, Jun. 26, 2012.
Pavelko et al., "The epitope integration site for vaccine antigens determines virus control while maintaining efficacy in an engineered cancer vaccine," *Mol Ther.*, 21(5):1087-1095, Epub Apr. 9, 2013.
Peach et al., "Both extracellular immunoglobulin-like domains of CD80 contain residues critical for binding T cell surface receptors CTLA-4 and CD28," *J Biol Chem.*, 270(36):21181-21187, Sep. 8, 1995.
Pece and Gutkind, "Signaling from E-cadherins to the MAPK pathway by the recruitment and activation of epidermal growth factor receptors upon cell-cell contact formation," *J Biol Chem.*, 275(52):41227-41233, Dec. 29, 2000.
Pedraza-Alva et al., "Activation of p38 MAP kinase by DNA double-strand breaks in V(D)J recombination induces a G2/M cell cycle checkpoint," *EMBO J.*, 25(4):763-773, Epub Feb. 2, 2006.
Peghini et al, [Immunophaenotyping in the diagnosis of lymphoma]. *Praxis (Bern 1994).*, 93(41):1687-1692, Oct. 6, 2004, Article in German, English abstract included.
Pei et al., "FKBP51 affects cancer cell response to chemotherapy by negatively regulating Akt," *Cancer Cell.*, 16(3):259-266, Sep. 8, 2009.
Penix et al., "Two essential regulatory elements in the human interferon gamma promoter confer activation specific expression in T cells," *J Exp Med.*, 178(5):1483-1496, Nov. 1, 1993.
Perriman et al., "Effective ribozyme delivery in plant cells," *Proc Natl Acad Sci U S A.*, 92(13):6175-6179, Jun. 20, 1995.
Petroff et al., "B7 family molecules: novel immunomodulators at the maternal-fetal interface," Placenta, 23 Suppl A:S95-101, Apr. 2002.
Piccini, "Vaccinia: virus, vector, vaccine," *Adv Virus Res.*, 34:43-64, 1988.
Plückthun et al., "Expression of functional antibody Fv and Fab fragments in *Escherichia coli*," *Methods Enzymol.*, 178:497-515, 1989.
Plückthun, "Antibodies from *Escherichia coli*." The Pharmacology of Monoclonal Antibodies. Handbook of Experimental Pharmacology, Springer Berlin Heidelberg, pp. 269-315, 1994.
Poirier, "Protective immunity evoked by oral administration of attenuated aroA *Salmonella typhimurium* expressing cloned streptococcal M protein," *J Exp Med.*, 168(1):25-32, Jul. 1, 1988.
Pollok et al., "4-1BB T-cell antigen binds to mature B cells and macrophages, and costimulates anti-mu-primed splenic B cells," *Eur J Immunol.*, 24(2):367-374, Feb. 1994.
Pollok et al., "Inducible T Cell Antigen 4-1BB," *J Immunol.*, 150(3):771-781, Feb. 1, 1993.
Ponder et al., "Tertiary templates for proteins. Use of packing criteria in the enumeration of allowed sequences for different structural classes," *J Mol Biol.*, 193(4):775-791, Feb. 20, 1987.
Porter, "The hydrolysis of rabbity-globulin and antibodies with crystalline papain," *Biochem J.*, 73:119-126, Sep. 1959.
Powell et al., "Compendium of excipients for parenteral formulations," *PDA J Pharm Sci Technol.*, 52(5):238-311, Sep.-Oct. 1998.
Prasad et al., "B7S1, a novel B7 family member that negatively regulates T cell activation," *Immunity*, 18(6):863-873, Jun. 2003.
Presta, "Antibody engineering," *Curr Opin Biotechnol.*, 2(4):593-596, 1992.
Presta, "Antibody engineering," *Curr Opin Biotechnol.*, 3(4):394-398, Aug. 1992.

Prévost-Blondel et al., "Tumor-infiltrating lymphocytes exhibiting high ex vivo cytolytic activity fail to prevent murine melanoma tumor growth in vivo," *J Immunol.*, 161(5):2187-2194, Sep. 1, 1998.
Pulko et al., "B7-h1 expressed by activated CD8 T cells is essential for their survival," *J Immunol.*, 187(11):5606-5614, Epub Oct. 24, 2011.
Pulko et al., "TLR3-stimulated dendritic cells up-regulate B7-H1 expression and influence the magnitude of CD8 T cell responses to tumor vaccination," *J Immunol.*, 183(6):3634-3641, Epub Aug. 26, 2009.
Qi et al., "Evidence that Ser87 of BimEL is phosphorylated by Akt and regulates BimEL apoptotic function," *J Biol Chem.*, 281(2):813-823, Epub Nov. 10, 2005.
Radhakrishnan et al., "Dendritic cells activated by cross-linking B7-DC (PD-L2) block inflammatory airway disease," *J Allergy Clin Immunol.*, 116(3):668-674, Sep. 2005.
Rai et al., "Tracking the total CD8 T cell response to infection reveals substantial discordance in magnitude and kinetics between inbred and outbred hosts," *J Immunol.*, 183(12):7672-7681, Dec. 15, 2009.
Rajewsky et al., "Genetics, expression, and function of idiotypes," *Annu Rev Immunol.*, 1:569-607, 1983.
Rathmell et al., "The central effectors of cell death in the immune system," Annu. Rev. Immunol., 17:781-828, 1999.
Razi-Wolf, "Expression and function of the murine B7 antigen, the major costimulatory molecule expressed by peritoneal exudate cells," *Proc Natl Acad Sci U S A.*, 89(9):4210-4214, May 1, 1992.
Renauld et al., "Expression cloning of the murine and human interleukin 9 receptor cDNAs," *Proc Natl Acad Sci U S A.*, 89(12):5690-5694, Jun. 15, 1992.
Riechmann et al., "Reshaping human antibodies for therapy," *Nature*, 332(6162):323-327, Mar. 24, 1988.
Rincon et al., "JNK and p38 MAP kinases in CD4+ and CD8+ T cells," *Immunol Rev.*, 192:131-142, Apr. 2003.
Ritz et al., "Bioassay analysis using R," *J Stat Softw.*, 12(5):1-22, Sep. 24, 2007.
Rivoltini et al., "Immunity to cancer: attack and escape in T lymphocyte-tumor cell interaction," *Immunol Rev.*, 188:97-113, Oct. 2002.
Robison-Cox, "Multiple estimation of concentrations in immunoassay using logistic models," *J Immunol Methods*, 186(1):79-88, Oct. 12, 1995.
Romano et al., "Quelling: transient inactivation of gene expression in Neurospora crassa by transformation with homologous sequences," *Mol Microbiol.*, 6(22):3343-3353, Nov. 1992.
Romero et al., "Ex vivo staining of metastatic lymph nodes by class I major histocompatibility complex tetramers reveals high numbers of antigen-experienced tumor-specific cytolytic T lymphocytes," *J Exp Med.*, 188(9):1641-1650, Nov. 2, 1998.
Rosenberg, "Progress in human tumor immunology and immunotherapy," *Nature*, 411(6835):380-384, May 17, 2001.
Rosenfeld et al., "Adenovirus-mediated transfer of a recombinant alpha 1-antitrypsin gene to the lung epithelium in vivo," *Science*, 252(5004):431-434, Apr. 19, 1991.
Rousseaux et al, "Optimal conditions for the preparation of proteolytic fragments from monoclonal IgG of different rat IgG subclasses," *Methods Enzymol.*, 121:663-669, 1986.
Rowe et al., "PDL-1 blockade impedes T cell expansion and protective immunity primed by attenuated Listeria monocytogenes," *J Immunol.*, 180(11):7553-7557, Jun. 1, 2008.
Sadoff, "Oral *Salmonella typhimurium* vaccine expressing circumsporozoite protein protects against malaria," *Science*, 240(4850):336-338, Apr. 15, 1988.
Salama et al., "Critical role of the programmed death-1 (PD-1) pathway in regulation of experimental autoimmune encephalomyelitis," *J Exp Med.*, 198(1):71-78, Jul. 7, 2003.
Salib et al., "Utilization of sodium alginate in drug microencapsulation," *Pharm Ind.*, 40(11a):1230-1234, 1978.
Salih et al., "4-1 BB ligand—just another costimulating molecule?," *Int J Clin Pharmacol Ther.*, 40(8):348-353, Aug. 2002.

(56) References Cited

OTHER PUBLICATIONS

Salih et al., "The role of leukemia-derived B7-H1 (PD-L1) in tumor-T-call interactions in humans," *Exp Hematol.*, 34(7):888-894, Jul. 2006.
Salomon et al., "Complexities of CD28/B7: CTLA-4 costimulatory pathways in autoimmunity and transplantation," *Annu Rev Immunol.*, 19:225-252, 2001.
Samulski, "Targeted integration of adenoassociated virus (AAV) into human chromosome 19," *EMBO J.*, 10(12):3941-3950, Dec. 1991.
Sandhu, "Protein engineering of antibodies," *Crit Rev Biotechnol.*, 12(5-6):437-462, 1992.
Sanni et al., "Evolution of aminoacyl-tRNA synthetase quaternary structure and activity: *Saccharomyces cerevisiae* mitochondrial phenylalanyl-tRNA synthetase," *Proc Natl Acad Sci U S.A.*, 88(19):8387-8391, Oct. 1, 1991.
Sarbassov et al., "Phosphorylation and regulation of Akt/PKB by the rictor-mTOR complex," *Science*, 307(5712):1098-1101, Feb. 18, 2005.
Sawhney et al., "Bioerodible hydrogels based on photopolymerized poly(ethylene glycol)-co-poly(.alpha.-hydroxy acid) diacrylate macromere," *Macromolecules*, 26(4):581-587, Jul. 1993.
Schafer, "Induction of a cellular immune response to a foreign antigen by a recombinant Listeria monocytogenes vaccine," *J Immunol.*, 149(1):53-59, Jul. 1, 1992.
Schmid et al, "Expression of AMPA receptor subunit flip/flop splice variants in the rat auditory brainstem and inferior colliculus," *J Comp Neurol.*, 430(2):160-171, Feb. 5, 2001.
Schmidt et al., "Extreme CD8 T cell requirements for anti-malarial liver-stage immunity following immunization with radiation attenuated sporozoites," *PLoS Pathog.*, 6(7):e1000998, Jul. 15, 2010.
Schmits et al., "LFA-1-deficient mice show normal CTL responses to virus but fail to reject immunogenic tumor," *J Exp Med.*, 183(4):1415-1426, Apr. 1, 1996.
Schurich et al., "The third signal cytokine IL-12 rescues the anti-viral function of exhausted HBV-specific CD8 T cells," *PLoS Pathog.*, 9(3):e1003208, Epub Mar. 14, 2013.
Schwartz et al, "Costimulation of T lymphocytes: the role of CD28, CTLA-4, and B7/BBl in interluekin-2 production and immunotherapy," *Cell*, 71(7):1065-1068, Dec. 24, 1992.
Schwartz et al., "Structural basis for co-stimulation by the human CTLA-4/B7-2 complex," *Nature*, 410(6828):604-608, Mar. 29, 2001.
Schwartz et al., "Structural mechanisms of costimulation," *Nat Immunol.*, 3(5):427-434, May 2002.
Sedletska et al., "Cisplatin is a DNA-damaging antitumour compound triggering multifactorial biochemical responses in cancer cells: importance of apoptotic pathways," *Curr Med Chem Anticancer Agents.*, 5(3):251-265, May 2005.
Seki et al., "Tumor-specific CTL kill murine renal cancer cells using both perforin and Fas ligand-mediated lysis in vitro, but cause tumor regression in vivo in the absence of perforin," *J Immunol.*, 168(7):3484-3492, Apr. 1, 2002.
Selenko-Gebauer et al., "B7-H1 (programmed death-1 ligand) on dendritic cells is involved in the induction and maintenance of T cell anergy," *J Immunol.*, 170(7):3637-3644, Apr. 1, 2003.
Seo et al., "Blockade of endogenous B7-H1 suppresses antibacterial protection after primary Listeria monocytogenes infection," *Immunology*, 123(1):90-99, Epub Oct. 25, 2007.
Shaknovich et al., "The promyelocytic leukemia zinc finger protein affects myeloid cell growth, differentiation, and apoptosis," *Mol Cell Biol.*, 18(9):5533-5545, Sep. 1998.
Shao et al., "Deficiency of the DNA repair enzyme ATM in rheumatoid arthritis," *J Exp Med.*, 206(6):1435-1449, Epub May 18, 2009.
Shao et al., "DNA-dependent protein kinase catalytic subunit mediates T-cell loss in rheumatoid arthritis," *EMBO Mol Med.*, 2(10):415-427, Oct. 2010.
Sharon et al., "Preparation of Fv fragment from the mouse myeloma. XRPC-25 immunoglobulin possessing anti-dinitrophenyl activity," *Biochemistry*, 15(7):1591-1594, Apr. 6, 1976.

Sheather, "Density Estimation," *Statistical Sci.*, 19(4):588-597, 2004.
Shin et al., "Cooperative B7-1/2 (CD80/CD86) and B7-DC costimulation of CD4+ T cells independent of the PD-1 receptor," *J Exp Med.*, 198(1):31-38, Jul. 7, 2003.
Sica et al., "B7-H4, a molecule of the B7 family, negatively regulates T cell immunity," *Immunity*, 18(6):849-861, Jun. 2003.
Sica et al., "Biochemical and immunological characteristics of 4-IBB (CD137) receptor and ligand and potential applications in cancer therapy," *Arch Immunol Ther Exp (Warsz).*, 47(5):275-279, 1999.
Siddiqui et al., "Tumor-infiltrating Foxp3-CD4+CD25+ T cells predict poor survival in renal cell carcinoma," *Clin Cancer Res.*, 13(7):2075-2081, Apr. 1, 2007.
Simon et al., "B7-h4 is a novel membrane-bound protein and a candidate serum and tissue biomarker for ovarian cancer," *Cancer Res.*, 66(3):1570-1575, Feb. 1, 2006.
Singer et al., "Optimal humanization of 1B4, an Anti-CD18 murine monoclonal antibody, is achieved by correct choice of human v-region framework sequences," *J Immunol.*, 150(7):2844-2857, Apr. 1, 1993.
Skerra et al., "Assembly of a functional immunoglobulin Fv fragment in *Escherichia coli*," *Science*, 240(4855):1038-1041, May 20, 1988.
Skolnick et al., "From genes to protein structure and function: novel applications of computational approaches in the genomic era," *Trends Biotechnol.*, 18(1):34-39, Jan. 2000.
Smith et al., Differential outcome of IL-2/anti-IL-2 complex therapy on effector and memory CD8+ T cells following vaccination with an adenoviral vector encoding EBV epitopes, *J Immunol.*, 186(10):5784-5790, Epub Apr. 11, 2011.
Smith et al., "Pulmonary deposition and clearance of aerosolized alpha-1-proteinase inhibitor administered to dogs and to sheep," *J Clin Invest.*, 84(4):1145-1154, Oct. 1989.
Sneller et al., "A novel lymphoproliferative/autoimmune syndrome resembling murine lpr/g1d disease," *J Clin Invest.*, 90(2):334-341, Aug. 1992.
Solier et al., "Death receptor-induced activation of the Chk2- and histone H2AX-associated DNA damage response pathways," *Mol Cell Biol.*, 29(1):68-82, Epub Oct. 27, 2008.
Sorge et al., "Amphotropic retrovirus vector system for human cell gene transfer," *Mol Cell Biol.*, 4(9):1730-1737, Sep. 1984.
Soriano, "Targeted and nontargeted liposomes for in vivo transfer to rat liver cells of a plasmid containing the preproinsulin I gene," *Proc Natl Acad Sci U S A.*, 80(23):7128-7131, Dec. 1983.
Soubeyrand et al., "Artemis phosphorylated by DNA-dependent protein kinase associates preferentially with discrete regions of chromatin," *J Mol Biol.*, 358(5):1200-1211, Epub Mar. 20, 2006.
Stammers et al., "BTL-II: A polymorphic locus with homology to the butyrolphilin gene family, located at the border of the major histocompatibility complex class II and class III regions in human and mouse," *Immunogenetics*, 51(4-5):373-382, Apr. 2000.
Stamper et al., "Crystal structure of the B7-1/CTLA-4 complex that inhibits human immune responses," *Nature*, 410(6828):608-611, Mar. 29, 2001.
Strome et al., "B7-H1 blockade augments adoptive T-cell immunotherapy for squamous cell carcinoma," *Cancer Res.*, 63(19):6501-6505, Oct. 1, 2003.
Strome et al., "Enhanced therapeutic potential of adoptive immunotherapy by in vitro CD28/4-1BB costimulation of tumor-reactive T cells against a poorly immunogenic, major histocompatibility complex class I-negative A9P melanoma," *J Immunother.*, 23(4):430-437, Jul.-Aug. 2000.
Subudhi et al., "Local expression of B7-H1 promotes organ-specific autoimmunity and transplant rejection," *J Clin Invest.*, 113(5):694-700, Mar. 2004.
Suda et al., "Why do defects in the Fas-Fas ligand system cause autoimmunity?" *J Allergy Clin Immunol.*, 100(6 Pt 2):S97-S101, Dec. 1997.
Summerton et al., "Morpholino antisense oligomers: design, preparation, and properties," *Antisense Nucleic Acid Drug Dev.*, 7(3):187-195, Jun. 1997.

(56) References Cited

OTHER PUBLICATIONS

Sun et al., "Administration of agonistic anti-4-1BB monoclonal antibody leads to the amelioration of experimental autoimmune encephalomyelitis," *J Immunol.*, 168(3):1457-1465, Feb. 1, 2002.
Sun et al., "Costimulatory molecule-targeted antibody therapy of a spontaneous autoimmune disease," *Nat Med.*, 8(12):1405-1413, Epub Nov. 11, 2002.
Sun et al., "Signaling of 4-1BB Leads to Amelioration of Experimental Autoimmune Encephalomyelitis," *FASEB J.*, vol. 5, p. A1210 Abstract 950.9, 2001.
Sutter et al., "Nonreplicating vaccinia vector efficiently expresses recombinant genes," *Proc Natl Acad Sci U S A.*, 89(22):10847-10851, Nov. 15, 1992.
Suzuki et al., "T cell-specific loss of Pten leads to defects in central and peripheral tolerance," *Immunity*, 14(5):523-534, May 2001.
Suzuki et al., "The dual functions of fas ligand in the regulation of peripheral CD8+ and CD4+ T cells," *Proc Natl Acad Sci U S A.*, 97(4):1707-1712, Feb. 15, 2000.
Swallow et al., "B7h, a novel costimulatory homolog of B7.1 and B7.2, is induced by TNFalpha," *Immunity*, 11(4):423-432, Oct. 1999.
Takahashi et al., "Cutting edge: 4-1BB is a bona fide CD8 T cell survival signal," *J Immunol.*, 162(9):5037-5040, May 1, 1999.
Takeda et al., "Critical contribution of liver natural killer T cells to a murine model of hepatitis," *Proc Natl Acad Sci U S A.*, 97(10):5498-5503, May 9, 2000.
Tamura et al., "B7-H1 costimulation preferentially enhances CD28-indepenent T-helper cell function," *Blood*, 97(6):1809-1816, Mar. 15, 2001.
Tamura et al., "Marrow stromal cells induce B7-H1 expression on myeloma cells, generating aggressive characteristics in multiple myeloma," *Leukemia*, 27(2):464-472, 2013.
Taylor et al., "Human immunoglobulin transgenes undergo rearrangement, somatic mutation and class switching in mice that lack endogenous IgM," *Int Immunol.*, 6(4):579-591, Apr. 1994.
Tazi-Ahnini et al., "Cloning, localization, and structure of new members of the butyrophilin gene family in the juxta-telomeric region of the major histocompatibility complex," *Immunogenetics*, 47(1):55-63, 1997.
Temin, "Safety considerations in somatic gene therapy of human disease with retrovirus vectors," *Hum Gene Ther.*, 1(2):111-123, Summer 1990.
Templeton et al., "Improved DNA: liposome complexes for increased systemic delivery and gene expression," *Nat Biotechnol.*, 15(7):647-652, Jul. 1997.
Theofilopoulos et al., "Tumour necrosis factor and other cytokines in murine lupus," *Ann Rheum Dis.*, 58(suppl 1):I49-55, Nov. 1, 1999.
Theofilopoulos et al., "Etiopathogenesis of Murine SLE," *Immunol Rev.*, 55:179-216, 1981.
Thompson et al., "cis-acting sequences required for inducible interleukin-2 enhancer function bind a novel Ets-related protein, Elf-1," *Mol Cell Biol.*, 12(3):1043-1053, Mar. 1992.
Thompson et al., "Costimulatory B7-H1 in renal cell carcinoma patients: Indicator of tumor aggressiveness and potential therapeutic target," *Proc Natl Acad Sci U S A.*, 101(49):17174-9. Epub Nov. 29, 2004.
Thompson et al., "Costimulatory molecule B7-H1 in primary and metastatic clear cell renal cell carcinoma," *Cancer*, 104(10):2084-2091, Nov. 15, 2005.
Thompson et al., "PD-1 is expressed by tumor-infiltrating immune cells and is associated with poor outcome for patients with renal cell carcinoma," *Clin Cancer Res.*, 13(6):1757-1761, Mar. 15, 2007.
Thompson et al., "Tumor B7-H1 is associated with poor prognosis in renal cell carcinoma patients with long-term follow-up," *Cancer Res.*, 66(7):3381-3385, Apr. 1, 2006.
Thompson et al., "Tumor masses support naive T cell infiltration, activation, and differentiation into effectors," *J Exp Med.*, 207(8):1791-1804, Epub Jul. 26, 2010.

Tian et al., "The relationship between the down-regulation of DNA-PKcs or Ku70 and the chemosensitization in human cervical carcinoma cell line HeLa," *Oncol Rep.*, 18(4):927-932, Oct. 2007.
Tiegs et al., "A T cell-dependent experimental liver injury in mice inducible by concanavalin A," *J Clin Invest.*, 90(1):196-203, Jul. 1992.
Titomirov, "In vivo electroporation and stable transformation of skin cells of newborn mice by plasmid DNA," *Biochim Biophys Acta.*, 1088(1):131-134, Jan. 17, 1991.
Todd et al., "Transcription of the interleukin 4 gene is regulated by multiple promoter elements," *J Exp Med.*, 177(6):1663-1674, Jun. 1, 1993.
Topalian et al., "Safety, activity, and immune correlates of anti-PD-1 antibody in cancer," *The New England Journal of Medicine.*, 368(26):2443-2454, Jun. 28, 2012.
Townsend et al., "Tumor rejection after direct costimulation of CD8+ T cells by B7-transfected melanoma cells," *Science*, 259(5093):368-370, Jan. 15, 1993.
Trabattoni et al. "B7-H1 is up-regulated in HIV infection and is a novel surrogate marker of disease progression" *Blood*, 101(7):2514-2520, Epub Dec. 5, 2002.
Tringler et al., "B7-h4 is highly expressed in ductal and lobular breast cancer," *Clin Cancer Res.*, 11(5):1842-1848, Mar. 1, 2005.
Truneh et al., "Early steps of lymphocyte activation bypassed by synergy between calcium ionophores and phorbol ester," *Nature.*, 313(6000):318-320, Jan. 24-30, 1985.
Tseng et al., "B7-DC, a new dendritic cell molecule with potent costimulatory properties for T cells," *J Exp Med.*, 193(7):839-846, Apr. 2, 2001.
Ueda et al., "Sequence-specific DNA damage induced by reduced mitomycin C and 7-N-(p-hydroxyphenyl)mitomycin C.," *Nucleic Acids Res.*, 12(17):6673-6683, Sep. 11, 1984.
Verhoeyen et al., "Reshaping human antibodies: grafting an antilysozyme activity," *Science*, 239(4847):1534-1536, Mar. 25, 1988.
Vesely et al., "Natural innate and adaptive 2011 immunity to cancer," *Annu Rev Immunol.*, 29:235-271, 2011.
Veuger et al., "Radiosensitization and DNA repair inhibition by the combined use of novel inhibitors of DNA-dependent protein kinase and poly(ADP-ribose) polymerase-1," *Cancer Res.*, 63(18):6008-6015, Sep. 15, 2003.
Vinay et al., "Role of 4-1BB in immune responses," *Semin Immunol.*, 10(6):481-489, Dec. 1998.
Wahl et al., "Improved radioimaging and tumor localization with monoclonal F(ab')2" *J Nucl Med.*, 24(4):316-25, Apr. 1983.
Walunas et al., "CTLA-4 ligation blocks CD28-dependent T cell activation," *J Exp Med.*, 183(6):2541-2550, Jun. 1, 1996.
Wang et al., "Costimulation of T cells by B7-H2, a B7-like molecule that binds ICOS," *Blood,*.96(8):2808-2813, Oct. 15, 2000.
Wang et al, "Doxorubicin induces apoptosis in normal and tumor cells via distinctly different mechanisms. intennediacy of H(2)O(2)- and p53-dependent pathways," *J Biol Chem*, 279(24):25535-25543, Epub Mar. 30, 2004.
Wang et al., "Ligand binding sites of inducible costimulator and high avidity mutants with improved function," *J Exp Med.*, 195(8):1033-1041, Apr. 15, 2002.
Wang et al., "Molecular modeling and functional mapping of B7-H1 and B7-DC uncouple costimulatory function from PD-1 interaction," *J Exp Med.*, 197(9):1083-1091, Epub Apr. 28, 2003.
Wang, "Lyophilization and development of solid protein pharmaceuticals," *Int J Pharm.*, 203(1-2):1-60, Aug. 10, 2000.
Wang, "pH-sensitive immunoliposomes mediate target-cell-specific delivery and controlled expression of a foreign gene in mouse," *Proc Natl Acad Sci U S A.*, 84(22):7851-7855, Nov. 1987.
Ward et al., "Binding activities of a repertoire of single immunoglobulin variable domains secreted from *Escherichia coli,"* *Nature*, 341(6242):544-546, Oct. 12, 1989.
Webster et al., "Targeting molecular and cellular inhibitory mechanisms for improvement of antitumor memory responses reactivated of by tumor cell vaccine," *J Immunol.*, 179(5):2860-2869, Sep. 1, 2007.
Weiss, "Hot Prospect for New Gene Amplifier: Ligase chain reaction, a combination DNA amplifier and genetic screen could do for

(56) References Cited

OTHER PUBLICATIONS

DNA diagnostics what PCR has done for basic molecular biology," *Science*, 254(5036):1292-1293, Nov. 29, 1991.
Wherry et al, "Lineage relationship and protective immunity of memory CD8 T cell subsets," *Nat Immunol.*, 4(3):225-234, Epub Feb. 3, 2003.
Wick et al., "The hepatic immune system," *Crit Rev Immunol.*, 22(1):47-103, 2002.
Wilcox et al., "Provision of antigen and CD137 signaling breaks immunological ignorance, promoting regression of poorly immunogenic tumors," *J Clin Invest.*, 109(5):651-659, Mar. 2002.
Williams et al., "Introduction of foreign genes into tissues of living mice by DNA-coated microprojectiles," *Proc Natl Acad Sci U S A.*, 88(7):2726-2730, Apr. 1, 1991.
Williams et al., "The immunoglobulin superfamily—domains for cell surface recognition," *Annu Rev Immunol.*, 6:381-405, 1988.
Williams et al., "Nitric oxide synthase plays a signaling role in TCR-triggered apoptotic death," *J Immunol.*, 161(12):6526-6531, Dec. 15, 1998.
Willmore et al., "A novel DNA-dependent protein kinase inhibitor, NU7026, potentiates the cytotoxicity of topoisomerase II poisons used in the treatment of leukemia," *Blood*, 103(12):4659-4665, Epub Mar. 9, 2004.
Winter et al., "Man-made antibodies," *Nature*, 349(6307):293-299, Jan. 24, 1991.
Winter et al., "Making antibodies by phage display technology," *Annu Rev Immunol.*, 12:433-455.
Wintterle et al., "Expression of the B7-related molecule B7-H1 by glioma cells: a potential mechanism of immune paralysis," *Cancer Res.*, 63(21):7462-7467, Nov. 1, 2003.
Wofsy et al., "The proliferating cells in autoimmune MRL/lpr mice lack L3T4, an antigen on "helper" T cells that is involved in the response to class II major histocompatibility antigens," *J Immunol.*, 132(6):2686-2689, Jun. 1984.
Wofsy, "Treatment of murine lupus with anti-CD4 monoclonal antibodies," *Immunol Ser.*, 59:221-236, 1993.
Wolff, "Direct gene transfer into mouse muscle in vivo," *Science*, 247(4949 Pt 1):1465-1468, Mar. 23, 1990.
Wong et al., "Human GM-CSF: molecular cloning of the complementary DNA and purification of the natural and recombinant proteins," *Science*, 228(4701):810-815, May 17, 1985.
Wu et al., The double-edged sword of activation-induced cytidine deaminase, *J Immunol.*, 174(2):934-941, Jan. 15, 2005.
Wu, "Receptor-mediated gene delivery and expression in vivo," *J Biol Chem.*, 263(29):14621-14624, Oct. 15, 1988.
Wu, "Targeting genes: delivery and persistent expression of a foreign gene driven by mammalian regulatory elements in vivo," *J Biol Chem.*, 264(29):16985-16987, Oct. 15, 1989.
Xu et al., "A potential new pathway for PD-L1 costimulation of the CD8-T cell response to Listeria monocytogenes infection," *PLoS One*, 8(2):e56539, Epub Feb. 11, 2013.
Xu et al., "The inducible expression of the tumor suppressor gene PTEN promotes apoptosis and decreases cell size by inhibiting the PI3K/Akt pathway in Jurkat T cells," *Cell Growth Differ.*, 13(7):285-296, Jul. 2002.
Yamamoto et al., "B7-H1 expression is regulated by MEK/ERK signaling pathway in anaplastic large cell lymphoma and Hodgkin lymphoma," *Cancer Sci.*, 100(11):2093-2100, Epub Aug. 1, 2009.
Yamazaki et al., "Expression of programmed death 1 ligands by murine T cells and APC," *J Immunol.*, 169(10):5538-5545, Nov. 15, 2002.
Yang et al., "In vitro priming of tumor-reactive cytolytic T lymphocytes by combining IL-10 with B7-CD28 costimulation," *J Immunol.*, 155(8):3897-3903, Oct. 15, 1995.
Yang et al., "In vivo and in vitro gene transfer to mammalian somatic cells by particle bombardment," *Proc Natl Acad Sci U S A*, 87(24):9568-9572, Dec. 1990.
Yang, "Gene transfer into mammalian somatic cells in vivo," *Crit Rev Biotechnol.*, 12(4):335-356, 1992.

Yoshinaga et al., "T-cell co-stimulation through B7RP-1 and ICOS," *Nature*, 402(6763):827-832, Dec. 16, 1999.
Yotsumoto et al., "Endosomal translocation of CpG-oligodeoxynucleotides inhibits DNA-PKcs-dependent IL-10 production in macrophages," *J Immunol.*, 180(2):809-816, Jan. 15, 2008.
Youngnak et al., "Differential binding properties of B7-H1 and B7-DC to programmed death-1," *Biochem Biophys Res Commun.*, 307(3):672-677, Aug. 1, 2003.
Yuan et al., "Focus on histone valiant H2AX: to be or not to b," *FEBS Lett.*, 584(17):3717-3724, Epub May 21, 2010.
Zang et al., "B7x: a widely expressed b7 family member that inhibits T cell activation," *Proc Natl Acad Sci U S A.*, 100(18):10388-10392, Epub Aug. 14, 2003.
Zang et al., "The B7 family and cancer therapy: costimulation and coinhibition," *Clin Cancer Res.*, 13(18 Pt 1):5271-5279, Sep. 15, 2007.
Zelenin et al., "Genetic transformation of mouse cultured cells with the help of high-velocity mechanical DNA injection," *FEBS Lett.*, 244(1):65-67, Feb. 13, 1989.
Zelemn et al., "High-velocity mechanical DNA transfer of the chloramphenicolacetyl transferase gene into rodent liver, kidney and mammary gland cells in organ explants and in vivo," *FEBS Lett.*, 280(1):94-96, Mar. 11, 1991.
Zhang et al., "PD-1/PD-L1 interactions inhibit antitumor immune responses in a murine acute myeloid leukemia model," *Blood*, 114(8):1545-1552, Epub May 5, 2009.
Zhang et al., "Theiler's virus-infected L-selectin-deficient mice have decreased infiltration of CD8(+) T lymphocytes in central nervous system but clear the virus," *J Neuroimmunol.*, 116(2):178-187, Jun. 1, 2001.
Zhou et al., "Inducible-costimulator-mediated suppression of human immunodeficiency virus type 1 replication in CD4+ T lymphocytes," *Virology*, 325(2):252-263, Aug. 1, 2004.
Zou et al., "Inhibitory B7-family molecules in the tumour microenvironment," *Nat Rev Immunol.*, 8(6):467-477, Jun. 2008.
Zula et al, "The role of cell type-specific responses in IFN-β therapy of multiple sclerosis," *Proc Natl Acad Sci U S A.*, 108(49):19689-19694, Epub Nov. 21, 2011.
Zumla et al. "Granulomatous infections: etiology and classification," *Clin Infect Dis.*, 23(1):146-158, Jul. 1996.
Zwiebel et al., "Drug delivery by genetically engineered cell implants," *Ann N Y Acad Sci.*, 618:394-404, 1991.
European Examination Report for Bristol-Myers Squibb Co., App. No. 07 023 993.4-1521, dated May 19, 2010, 6 pages.
European Office Action in Application No. EP 14850189.3, dated Mar. 24, 2017, 5 pages.
European Search Report for Application No. EP 02802551, 3 pages, completed Oct. 14, 2004.
European Search Report for Application No. EP 14850189.3, dated Feb. 27, 2017, 5 pages.
International Preliminary Report on Patentability for PCT/US2014/053870, dated Apr. 5, 2016, 7 pages.
International Preliminary Report on Patentability in International Application No. PCT/US03/22029, dated Mar. 25, 2005, 5 pages.
International Preliminary Report on Patentability in International Application No. PCT/US07/060133, dated Oct. 30, 2008, 8 pages.
International Preliminary Report on Patentability in International Application No. PCT/US07/60150, dated Sep. 18, 2008, 5 pages.
International Preliminary Report on Patentability in International Application No. PCT/US2007/066970, dated Oct. 30, 2008, 8 pages.
International Preliminary Report on Patentability in International Application No. PCT/US2015/031993, dated Nov. 22, 2016, 11 pages.
International Preliminary Report on Patentability in International Application No. PCT/US2015/032016, dated Jan. 24, 2017, 11 pages.
International Preliminary Report on Patentability re PCT/US2009/035495, dated Sep. 10, 2010, 5 pages.
International Search Report and Written Opinion for PCT/US16/58852, dated Apr. 28, 2017, 15 pages.

(56) References Cited

OTHER PUBLICATIONS

International Search Report and Written Opinion for PCT/US2014/053870, dated Feb. 4, 2015, 12 pages.
International Search Report and Written Opinion for PCT/US2015/031993, dated Sep. 29, 2015, 18 pages.
International Search Report and Written Opinion for PCT/US2015/032016, dated Aug. 26, 2015, 17 pages.
International Search Report and Written Opinion in International Application No. PCT/US07/60133, dated Sep. 25, 2008, 13 pages.
International Search Report and Written Opinion in International Application No. PCT/US07/60150, dated Jul. 7, 2008, 8 pages.
International Search Report and Written Opinion in International Application No. PCT/US2007/066970, dated Oct. 5, 2007, 13 pages.
International Search Report and Written Opinion of the International Search Authority re PCT/US2009/035495, dated Oct. 6, 2009, 7 pages.
International Search Report for PCT/US2002/32364, dated Mar. 25, 2003, 2 pages.
International Search Report in International Application No. PCT/US03/22029, dated Dec. 2, 2004, 5 pages.
Invitation to Pay for PCT/US2014/053870, dated Nov. 19, 2014, 3 pages.
Supplementary European Search Report in International Application No. 03764649.4-2107, dated Oct. 6, 2006, 5 pages.
Pardoll., "The Blockade of Immune Checkpoints in Cancer Immunotherapy," Nat Review., 12:252-264, Apr. 2012.
Extended European Search Report in International Application No. 15825450.8, dated Feb. 21, 2018, 9 pages.
Dronca et al., "T cell Bim levels reflect responses to anti-PD-1 cancer therapy," *JCI Insight.*, 1(6):e86014, May 5, 2016, 14 pages.
Dronca et al., "BCL-2-interacting mediator of cell death (Bim) is a novel biomarker for response to anti-PD-1 therapy in patients with advanced melanoma," *Immunotherapy*, 8(12)1351-1353, Dec. 1, 2016.
European Office Action in Application No. EP 14850189.3, dated Oct. 26, 2017, 11 pages.
U.S. Appl. No. 15/019,457, filed Feb. 9, 2016, 20160153996, Jun. 2, 2016, Kwon et al.
U.S. Appl. No. 15/019,548, filed Feb. 9, 2016, 20160154000, Jun. 2, 2016, Kwon et al.
U.S. Appl. No. 15/026,461, filed Sep. 1, 2016, 20160251437, Sep. 1, 2016, Dong et al.
U.S. Appl. No. 15/054,385, filed Feb. 26, 2016, 20160176967, Jun. 23, 2016, Dong et al.
U.S. Appl. No. 15/325,612, filed Jan. 11, 2017, 20170173030, Jun. 22, 2017, Dong.
U.S. Appl. No. 15/692,656, filed Aug. 31, 2017, Pending, Pending, Kwon et al.

\* cited by examiner

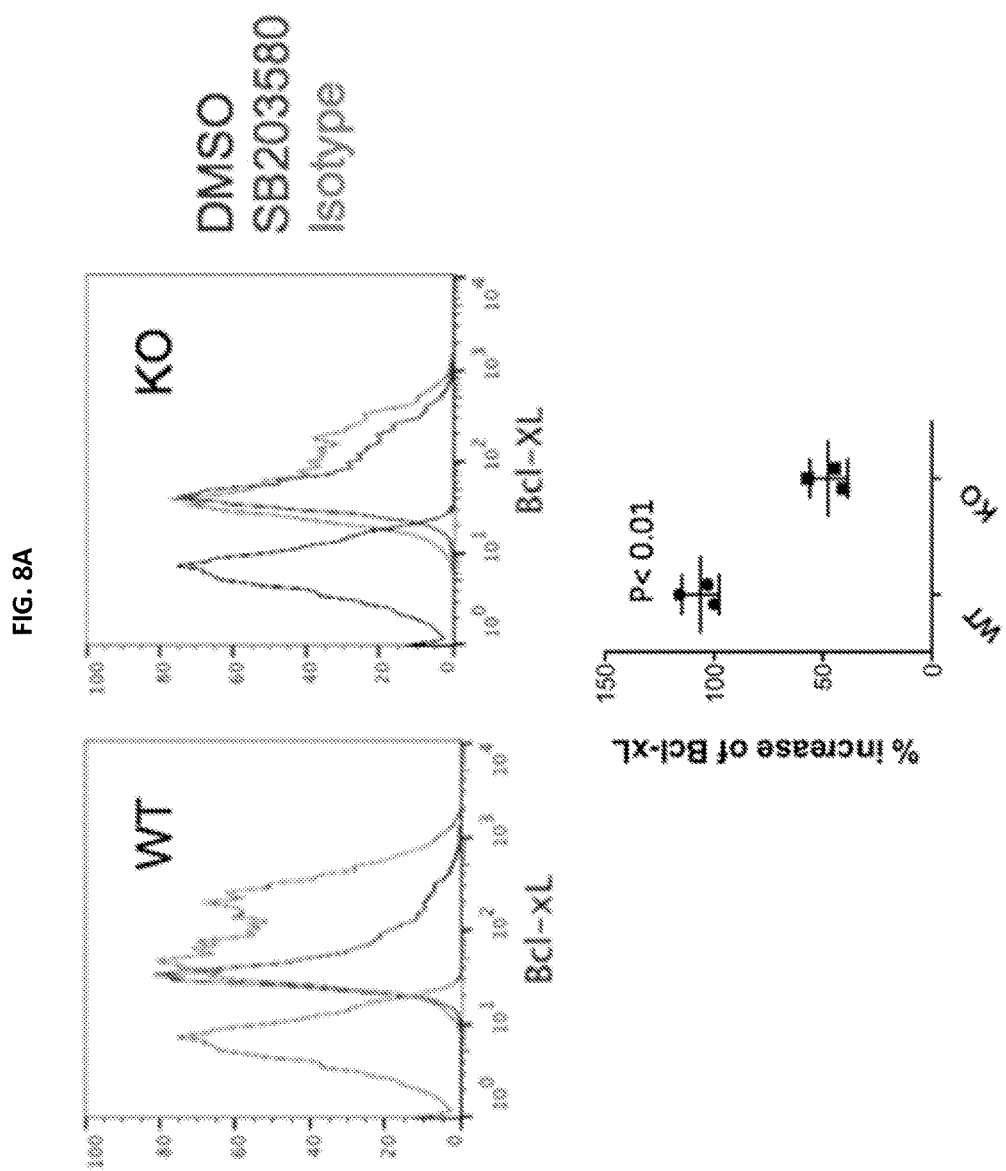

FIG. 11

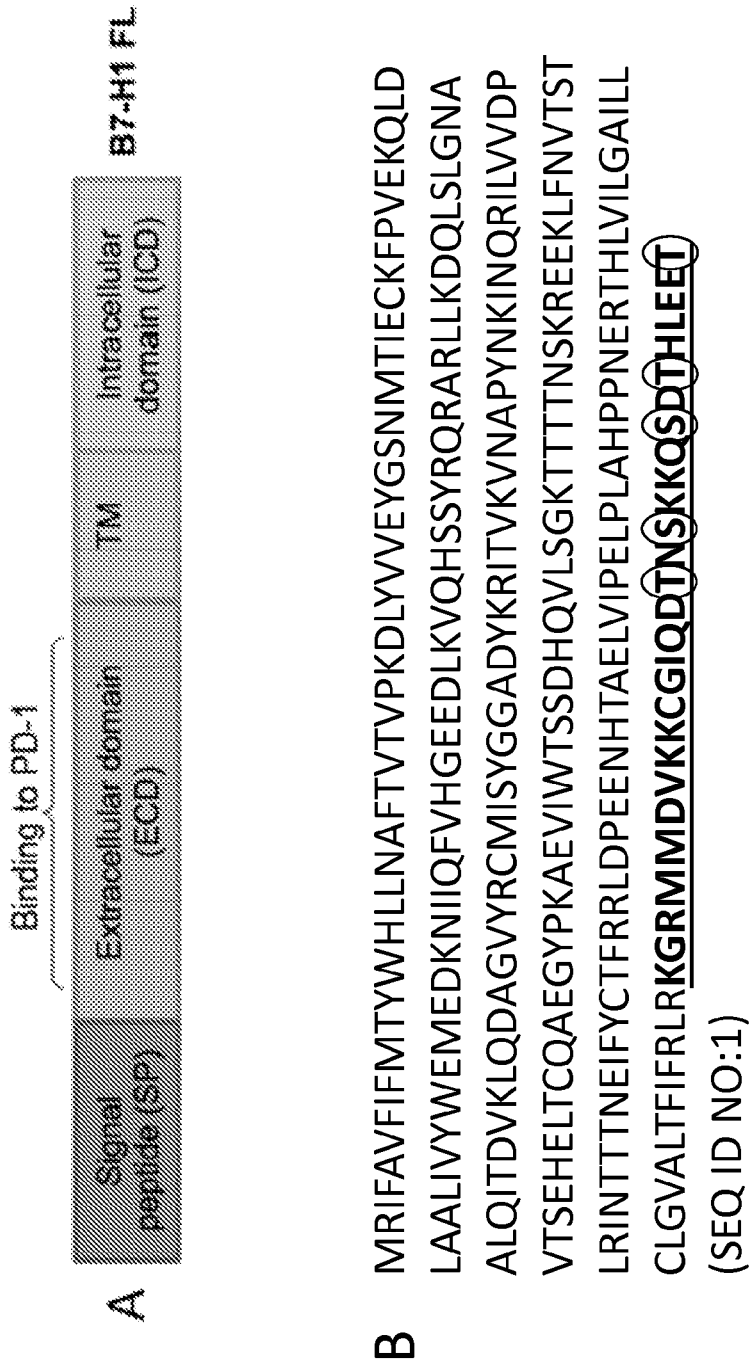

A [Signal peptide (SP) | Extracellular domain (ECD) | TM | Intracellular domain (ICD)] B7-H1 FL Binding to PD-1

B  MRIFAVFIFMTYWHLLNAFTVTVPKDLYVVEYGSNMTIECKFPVEKQLD
LAALIVYWEMEDKNIIQFVHGEEDLKVQHSSYRQRARLLKDQLSLGNA
ALQITDVKLQDAGVYRCMISYGGADYKRITVKVNAPYNKINQRILVVDP
VTSEHELTCQAEGYPKAEVIWTSSDHQVLSGKTTTTNSKREEKLFNVTST
LRINTTTNEIFYCTFRRLDPEENHTAELVIPELPLAHPPNERTHLVILGAILL
CLGVALTFIFRLRLRKGRMMMDVKKCGIQDTNSKKQSDTHLEET

(SEQ ID NO:1)

FIG. 18

| Simultaneously detect the relative phosphorylation of these kinases in a single sample | |
|---|---|
| Akt1 | HSP27 | p38 beta |
| Akt2 | JNK1 | p38 delta |
| Akt3 | JNK2 | p38 gamma |
| Akt pan | JNK3 | p53 |
| CREB | JNK pan | p70 S6K |
| ERK1 | MKK3 | RSK1 |
| ERK2 | MKK6 | RSK2 |
| GSK-3 alpha/beta | MSK2 | TOR |
| GSK-3 beta | P38 alpha | |

DISTINGUISHING ANTAGONISTIC AND AGONISTIC ANTI B7-H1 ANTIBODIES

CROSS-REFERENCE TO RELATED APPLICATIONS

This application is a National Stage application under 35 U.S.C. § 371 of International Application No. PCT/US2015/031993, having an International Filing Date of May 21, 2015, which claims the benefit of U.S. Provisional Ser. No. 62/001,984, filed on May 22, 2014. This disclosure of the prior application is considered part of (and is incorporated by reference in) the disclosure of this application.

TECHNICAL FIELD

This document relates to materials and methods for distinguishing agonistic anti-B7-H1 antibodies from antagonistic anti-B7-H1 antibodies, and for treating subjects diagnosed as having a clinical condition such as cancer or a pathogenic infection with B7-H1 antibodies identified as having or not having particular activities.

BACKGROUND

Elevated tumor expression of B7-H1 (also known as PD-L1) is predictive of an aggressive disease course, including increased risk of progression and cancer-related death (Thompson et al., *Cancer Res* 66:3381-3385, 2006; and Zang and Allison, Clin *Cancer Res* 13:5271-5279, 2007). Retrospective studies suggested that tumors exploit B7-H1 expression to inhibit host T cell function, thereby fostering malignant progression. The concept of tumor B7-H1-mediated immune evasion was an impetus for implementing B7-H1 blockade as a tumor immunotherapy (Zang and Allison, supra; Zou and Chen, *Nat Rev Immunol* 8:467-477, 2008, Dong and Chen, *J Mol Med* 81:281-287, 2003; Li et al., *Clin Cancer Res* 15:1623-1634, 2009; and Webster et al., *J Immunol* 179:2860-2869, 2007). B7-H1 blockade can dramatically improve tumor immunotherapy by increasing the function of effector CD8 T cells (Strome et al., *Cancer Res* 63:6501-6505, 2003; Hirano et al., *Cancer Res* 65:1089-1096, 2005; Blank et al., *Int J Cancer* 119:317-327, 2006; and Iwai et al., *Proc Natl Acad Sci USA* 99:12293-12297, 2002). Preclinical studies also provided evidence that B7-H1 blockade may be useful as a treatment for advanced human solid cancers (Dong and Chen, supra; Brahmer et al., *New Engl J Med* 366:2455-2465, 2012; and Dong and Chen, *Cell Mol Immunol* 3:179-187, 2006). In these studies, however, only a small portion of treated patients exhibited lasting objective responses (Brahmer et al., supra).

SUMMARY

This document is based, at least in part, on the discovery that unintentional disruption of a previously unknown function of B7-H1 in T cell survival may seriously counter beneficial effects of B7-H1 blockade, and on the development of assays for distinguishing agonistic B7-H1 antibodies from antagonistic B7-H1 antibodies. As described herein, an anti-B7-H1 antibody given at the early stage of immunization can increase the numbers of effector CD8 T cells, while reducing the numbers of effector CD8 T cells when given at a later stage. The hypotheses that B7-H1 expressed by activated CD8 T cells has an intrinsic pro-survival function required for establishment of T cell immunity, and that ligation of B7-H1 by agonistic antibody may disrupt its pro-survival function in T cells, are new concepts in addressing T cell survival and differentiation. The findings discussed herein challenge the conventional assumption that B7-H1 is singularly an immune inhibitory molecule. By understanding the intrinsic signaling pathways of B7-H1 in T cells, it may be possible to develop new subcellular targets for regulating T cell survival, to screen B7-H1 blockade antibodies to improve T cell immunity against cancer and pathogenic infections, and to provide improved treatment methods for patients.

In one aspect, this document features a method for identifying an anti B7-H1 antibody as having agonistic activity. The method can include contacting a population of activated T cells with the antibody, performing a quantitative assay to measure the level of p38 mitogen-activated protein kinase (MAPK) activation in the T cells, and identifying the antibody as having agonistic activity when the level of p38 MAPK activation is increased in the activated T cells as compared to a control level of p38 MAPK activation. The level of p38 MAPK activation can be measured using flow cytometry, or measured as an increase in phosphorylation. The method can include contacting the T cell population with the anti B7-H1 antibody for 12-36 hours (e.g., for 24 hours). The control level of p38 MAPK activation can be the level of p38 MAPK activation in a population of activated T cells contacted with control IgG.

In another aspect, this document features a method for modulating T cell survival or function in a subject. The method can include administering to the subject an antibody that specifically binds to B7-H1, where the antibody is identified as having antagonistic activity but not agonistic activity, agonistic activity but not antagonistic activity, predominantly antagonistic activity, or predominantly agonistic activity, and where the antibody is administered in an amount effective to increase or decrease T cell function or survival in the subject. For example, the subject can be a subject diagnosed as having cancer or a pathogenic infection, and the antibody can be identified as having antagonistic activity but not agonistic activity, or as having predominantly antagonistic activity, where the antibody is administered in an amount effective to increase T cell function or survival in the subject. The antibody can be identified as having antagonistic activity based at least in part on its ability to block forward signaling of B7-H1 through PD-1. In another example, the subject can be a subject diagnosed as having an autoimmune disease, and the antibody can be identified as having agonistic activity but not antagonistic activity, or as having predominantly agonistic activity, where the antibody is administered in an amount effective to decrease T cell function or survival in the subject. The antibody can be identified as having agonistic activity based at least in part on its ability to trigger signaling through p38 mitogen-activated protein kinase (MAPK).

This document also features a composition comprising a pharmaceutically acceptable carrier and an antibody that specifically binds to B7-H1, where the antibody is identified as having antagonistic activity but not agonistic activity, agonistic activity but not antagonistic activity, predominantly antagonistic activity, or predominantly agonistic activity. The antibody can be identified as having antagonistic activity but not agonistic activity, or as having predominantly antagonistic activity, and can be identified as having antagonistic activity based at least in part on its ability to block forward signaling of B7-H1 through PD-1. The antibody can be identified as having agonistic activity but not antagonistic activity, or as having predominantly agonistic activity, and can be identified as having agonistic activity based at least in part on its ability to trigger signaling through p38 MAPK.

In still another aspect, this document features an antibody that specifically binds to B7-H1, or a composition containing a pharmaceutically acceptable carrier and an antibody that specifically binds to B7-H1, for use in modulating T cell survival or function in a subject. The antibody can be identified as having antagonistic activity but not agonistic activity, agonistic activity but not antagonistic activity, predominantly antagonistic activity, or predominantly agonistic activity. In use, the antibody can be administered in an amount effective to increase or decrease T cell function or survival in the subject. For example, the subject can be a subject diagnosed as having cancer or a pathogenic infection, and the antibody can be identified as having antagonistic activity but not agonistic activity, or as having predominantly antagonistic activity, where the antibody is to be administered in an amount effective to increase T cell function or survival in the subject. The antibody can be identified as having antagonistic activity based at least in part on its ability to block forward signaling of B7-H1 through PD-1. In another example, the subject can be a subject diagnosed as having an autoimmune disease, and the antibody can be identified as having agonistic activity but not antagonistic activity, or as having predominantly agonistic activity, where the antibody is to be administered in an amount effective to decrease T cell function or survival in the subject. The antibody can be identified as having agonistic activity based at least in part on its ability to trigger signaling through p38 MAPK.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A is a graph plotting B16-OVA tumor growth in mice transferred with activated CD8 T cells. Tumor sizes are shown as mean±SD of five mice per group. *$p<0.05$. FIG. 3B shows the accumulation of transferred OT-1 CD8 T cells (KbOVA-tetramer, tet$^+$) at the tumor site and spleen. Numbers show the percentage of tee CD8 T cells. FIG. 3C is a graph plotting cytolytic activity in the spleens of recipient mice. EL-4 cells that were pulsed with OVA peptide (solid lines) or control peptide (dotted lines) were used as target cells in a 4 hour calcein release assay. Data are representative of three independent experiments with three mice per group.

FIGS. 4A and 4B show apoptosis of activated CD8 T cells. Numbers are average percentages of apoptotic (Annexin V$^+$ TMRE$^{low}$ or active caspase-3$^+$) CD8 T cells. *$p<0.05$, **$p<0.01$. FIG. 4C is a graph plotting the numbers of viable T cells (n=3). *$p<0.05$. FIG. 4D is a series of graphs plotting proliferation (based on the dilution of CFSE). Numbers are the percentages of proliferating T cells that have undergone three or more times of division, *$p<0.05$.

FIG. 5A is a pair of graphs showing the effects of separate transfer of WT or B7-H1 KO T cells (Thy1.2$^+$) into Thy1.1$^+$ host model. Similar expansion was observed (N.S., no significant difference) at day 4 (top panel), while a bit more contraction of B7-H1 KO T cells was observed on day 6 following immunization (*$p<0.05$ compared to WT T cells) (bottom panel). FIG. 5B is a pair of graphs showing the effects of co-transfer of pre-activated WT (Thy1.2$^+$CD45.1$^+$) and B7-H1 KO (Thy1.2$^+$ CD45.1-) into a Thy1.1$^+$ host model. Injection of anti-PD-1 antibody (bottom panel) did not interfere with T cell contraction on day 2 post transfer.

FIG. 6A shows intracellular staining for Bcl-xL, Bcl-2, and Bim in resting (top panel) and activated (bottom panel) WT and B7-H1 KO CD8 T cells. MFI: mean fluorescence intensity. *$p<0.01$ compared with WT cells. FIG. 6B is a bar graph plotting the average MFI of Bcl-xL expressed by activated WT and B7-H1 KO T cells (mean±SD, n=3).

FIGS. 8A and 8B show regulation of Bcl-xL by B7-H1 via p38 MAPK. Pre-activated WT and B7-H1 KO CD8 T cells were incubated with SB203580 (10 uM) or solvent DMSO for 48 hours. FIG. 8A is a pair of histograms plotting intracellular staining for Bcl-xL in WT T cells (left panel) and in KO T cells (center panel). The percent increase in Bcl-xL was higher in WT T cells than in KO T cells (right panel). FIG. 8B is a diagram of a potential mechanism of regulation of Bcl-xL by B7-H1 via p38 MAPK.

FIG. 11A is a diagram depicting the domains of the B7-H1 protein. FIG. 11B shows a representative amino acid sequence for B7-H1 (SEQ ID NO:1). The intracellular domain (ICD) of B7-H1 is underlined and in bold. Serine and threonine residues are circled.

FIG. 16A is a graph plotting the average levels of phosphor-p38 MAPK. MFI: mean fluorescence intensity. FIG. 16B is a histogram of phosphor-p38 MAPK expression.

FIG. 17A is a graph plotting the percent of apoptotic T cells (TMRE$^{low}$ Annexin V$^+$). FIG. 17B shows a representative staining of TMRE and Annexin V in CD8 T cells.

FIG. 18 is a list of candidate proteins in the MAPK/ERK pathway that will be screened and compared in B7-H1 and mock transfected tumor cells.

FIG. 19A is a picture showing cells stained for B7-H1 (brown, arrows) and CD8 (red). FIG. 19B is a graph plotting the percentages of B7-H1$^+$ CD8 T cells in tumor infiltrating lymphocytes (TIL) and peripheral blood of RCC patients. *p=0.017, **p=0.043 vs. normal donors (n=17).

FIG. 20A is a graph plotting the kinetics of CD11a$^{high}$ CD8 T cells (dashed line) and tumor growth (solid line). FIG. 20B is a graph plotting B7-H1 levels (MFI) on CD11a$^{high}$ CD8 T cells from spleen and tumor infiltrating lymphocytes (TIL) of tumor mice, or on naïve CD8 T cells (baseline).

DETAILED DESCRIPTION

Figure 1:
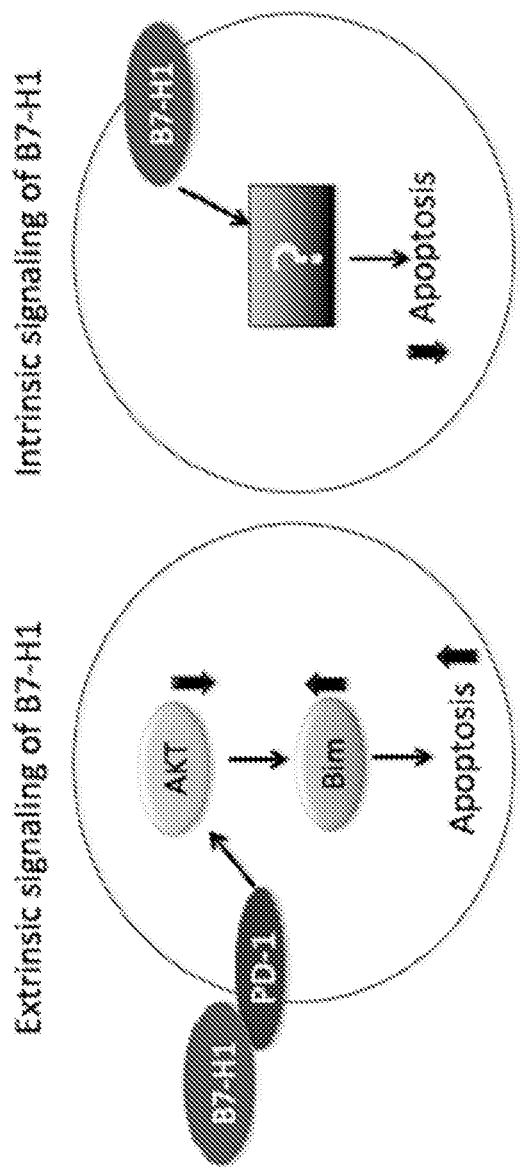
FIG. 1 is a diagram depicting a bi-directional signaling model for B7-H1 in T cells.

Some B7-H1 antibodies may disrupt a previously unknown function of B7-H1 in T cells, as indicated by the apparent ability of anti-B7-H1 antibodies to reduce CD8 T cell responses (Xu et al., supra; and Pulko et al., *J Immunol* 187:5606-5614, 2011). A bi-directional signaling model of B7-H1 is proposed in FIG. 1. In this model, the extrinsic signaling of B7-H1 is mediated by PD-1, which impairs T cell function and survival via reduction of AKT activation (Patsoukis et al., *Science Signaling* 5:ra46, 2012) and up-regulation of Bim (Gibbons et al., *Oncoimmunology* 1:1061-1073, 2012). As a result, T cell function and survival are compromised. Current B7-H1 therapies using blocking antibodies are aimed at blocking this extrinsic effect of B7-H1, thereby enhancing antitumor T cell immunity. The intrinsic signaling of B7-H1 is mediated by an unknown mechanism that leads to stabilizing pro-survival molecules in T cells. The data presented herein reveal that B7-H1 per se is required for the survival of activated T cells (Pulko et al., supra), and that ligation of B7-H1 by antibody triggers proapoptosis signals in T cells (Dong et al., supra). Therefore, if the intrinsic prosurvival function of B7-H1 is disrupted (for example, by an agonistic antibody), CD8 T cells that express B7-H1 would undergo apoptosis, resulting in compromised immunity.

To achieve maximal therapeutic effects of B7-H1 blockade therapy in cancer treatment, it is imperative that the new function of B7-H1 expressed by T cells be fully characterized. However, no methodology has been reported for evaluating whether the use of anti-B7-H1 antibodies in treatment of cancer has a potential to impart unfavorable effects on T cell survival, and whether such unfavorable effects could be avoided by screening anti-B7-H1 antibodies before administration to patients. This document provides materials and methods focused on defining the nature of intrinsic signals of B7-H1 in T cell apoptosis/differentiation, and on evaluating the impact of agonistic anti-B7-H1 antibodies on antitumor T cell immunity. The studies discussed herein provide new approaches (i.e., screening antibodies) for advancing checkpoint blockade immunologically and therapeutically.

A representative example of a human B7-H1 polypeptide has the sequence set forth in GENBANK® Accession No. AAF25807 (GI No. 6708119) (SEQ ID NO:1; FIG. 11B); the corresponding human B7-H1 nucleic acid has the sequence set forth in GENBANK® Accession No. AF177937 (GI No. 6708118) (SEQ ID NO:2).

The term "antibody" includes monoclonal antibodies, polyclonal antibodies, recombinant antibodies, humanized antibodies (Jones et al. (1986) *Nature* 321:522-525; Riechmann et al. (1988) *Nature* 332:323-329; and Presta (1992) *Curr Op Struct Biol* 2:593-596), chimeric antibodies (Morrison et al. (1984) *Proc Natl Acad Sci USA* 81:6851-6855), multispecific antibodies (e.g., bispecific antibodies) formed from at least two antibodies, and antibody fragments. The term "antibody fragment" comprises any portion of the afore-mentioned antibodies, such as their antigen binding or variable regions. Examples of antibody fragments include Fab fragments, Fab' fragments, F(ab')2 fragments, Fv fragments, diabodies (Hollinger et al. (1993) *Proc Natl Acad Sci USA* 90:6444-6448), single chain antibody molecules (Plückthun in: *The Pharmacology of Monoclonal Antibodies* 113, Rosenburg and Moore, eds., Springer Verlag, N.Y. (1994), 269-315) and other fragments as long as they exhibit the desired capability of binding to B7-H1.

Examples of anti-human B7-H1 antibodies include, without limitation, anti-human B7-H1 antibodies commercially available from Biolegend (e.g., Catalog No. 329701 or 329702; San Diego, Calif.) or eBioscience (e.g., Catalog No. 14-5983-80 or 14-5983-82).

The term "antibody," as used herein, also includes antibody-like molecules that contain engineered sub-domains of antibodies or naturally occurring antibody variants. These antibody-like molecules may be single-domain antibodies such as $V_H$-only or $V_L$-only domains derived either from natural sources such as camelids (Muyldermans et al. (2001) *Rev Mol Biotechnol* 74:277-302) or through in vitro display of libraries from humans, camelids or other species (Holt et al. (2003) *Trends Biotechnol* 21:484-90). In certain embodiments, the polypeptide structure of the antigen binding proteins can be based on antibodies, including, but not limited to, minibodies, synthetic antibodies (sometimes referred to as "antibody mimetics"), human antibodies, antibody fusions (sometimes referred to as "antibody conjugates"), and fragments thereof, respectively.

An "Fv fragment" is the minimum antibody fragment that contains a complete antigen-recognition and -binding site. This region consists of a dimer of one heavy chain variable domain and one light chain variable domain in tight, non-covalent association. It is in this configuration that the three CDR's of each variable domain interact to define an antigen-binding site on the surface of the VH-VL dimer. Collectively, the six CDR's confer antigen-binding specificity to the antibody. However, even a single variable domain (or half of an Fv comprising only three CDR's specific for an antigen) has the ability to recognize and bind the antigen, although usually at a lower affinity than the entire binding site. The "Fab fragment" also contains the constant domain of the light chain and the first constant domain ($C_H1$) of the heavy chain. The "Fab fragment" differs from the "Fab' fragment" by the addition of a few residues at the carboxy terminus of the heavy chain $C_H1$ domain, including one or more cysteines from the antibody hinge region. The "F(ab')2 fragment" originally is produced as a pair of "Fab' fragments" which have hinge cysteines between them. Methods of preparing such antibody fragments, such as papain or pepsin digestion, are known to those skilled in the art.

An antibody can be of the IgA-, IgD-, IgE-, IgG- or IgM-type, including IgG- or IgM-types such as, without limitation, IgG1-, IgG2-, IgG3-, IgG4-, IgM1- and IgM2-types. For example, in some cases, the antibody is of the IgG1-, IgG2- or IgG4-type.

In some embodiments, antibodies as used in the methods described herein can be fully human or humanized antibodies. Human antibodies can avoid certain problems associated with xenogeneic antibodies, such as antibodies that possess murine or rat variable and/or constant regions. First, because the effector portion is human, it can interact better with other parts of the human immune system, e.g., to destroy target cells more efficiently by complement-dependent cytotoxicity or antibody-dependent cellular cytotoxicity. Second, the human immune system should not recognize the antibody as foreign. Third, half-life in human circulation will be similar to naturally occurring human antibodies, allowing smaller and less frequent doses to be given. Methods for preparing human antibodies are known in the art.

In addition to human antibodies, "humanized" antibodies can have many advantages. Humanized antibodies generally are chimeric or mutant monoclonal antibodies from mouse, rat, hamster, rabbit or other species, bearing human constant and/or variable region domains or specific changes. Techniques for generating humanized antibodies are well known to those of skill in the art. For example, controlled rearrangement of antibody domains joined through protein disulfide bonds to form new, artificial protein molecules or "chimeric" antibodies can be utilized (Konieczny et al. (1981) *Haematologia* (*Budap.*) 14:95). Recombinant DNA technology can be used to construct gene fusions between DNA sequences encoding mouse antibody variable light and heavy chain domains and human antibody light and heavy chain constant domains (Morrison et al. (1984) *Proc Natl Acad Sci USA* 81:6851).

DNA sequences encoding antigen binding portions or complementarity determining regions (CDR's) of murine monoclonal antibodies can be grafted by molecular means into DNA sequences encoding frameworks of human antibody heavy and light chains (Jones et al. (1986) *Nature* 321:522; Riechmann et al. (1988) *Nature* 332:323). Expressed recombinant products are called "reshaped" or humanized antibodies, and comprise the framework of a human antibody light or heavy chain and antigen recognition portions, CDR's, of a murine monoclonal antibody.

Other methods for designing heavy and light chains and for producing humanized antibodies are described in, for example, U.S. Pat. Nos. 5,530,101; 5,565,332; 5,585,089; 5,639,641; 5,693,761; 5,693,762; and 5,733,743. Yet additional methods for humanizing antibodies are described in U.S. Pat. Nos. 4,816,567; 4,935,496; 5,502,167; 5,558,864; 5,693,493; 5,698,417; 5,705,154; 5,750,078; and 5,770,403, for example.

The methods provided herein can include determining whether an antibody against B7-H1 has antagonistic function, such that it has the ability to block forward signaling of B7-H1 through PD-1, and/or determining whether an antibody against B7-H1 has agonistic function, such that it has the ability to trigger signaling through p38 MAPK. The antagonistic ability of an antibody to block forward signaling of B7-H1 through PD-1 can result in increased T cell function, while the agonistic ability of an antibody to trigger signaling through p38 MAPK can result in decreased T cell function and survival. Thus, an anti B7-H1 antibody that has the ability to block forward signaling through PD-1 but has low ability or lacks the ability to trigger signaling through p38 MAPK, may be particularly useful for treating cancer and other disorders (e.g., pathogenic infections) in which it can be advantageous to increase T cell function. In contrast, a dual function anti B7-H1 antibody that also has the ability to trigger signaling through p38 MAPK may have the opposite effect on T cell function and survival, and thus may not have a significant clinical benefit in treatment of cancer patients. Such antibodies may, however, be useful for treating conditions (e.g., autoimmune disorders) in which decreased T cell function is desired.

Methods for determining whether an anti B7-H1 antibody has antagonistic and/or agonistic function include those described herein (see, e.g., the Examples below). For example, the effect of an antibody on T cell survival can be tested in vivo using an animal model, by administering the antibody to an immunized animal and then examining the number and/or percentage of antigen specific and functional CD8 T cells in the animal's spleen.

In some cases, the potential agonistic function of a particular anti B7-H1 antibody can be evaluated by assaying the effect of the antibody on p38 MAPK activation. For example, the activity of an anti B7-H1 antibody can be assessed by contacting activated T cells with the antibody (e.g., for 2-48 hours, such as 6-36 hours, 12-36 hours, or about 24 hours), and measuring the level of p38 MAPK activation in the T cells. An antibody can be identified as having agonistic activity when the level of p38 MAPK activation is increased in the activated T cells as compared to a control level of p38 MAPK activation (e.g., the level of p38 MAPK activation in activated T cells contacted with a control IgG rather than with the anti B7-H1 antibody). The activation of p38 MAPK can be indicated by an increase in the level of p38 MAPK phosphorylation, for example, and any suitable method can be used to assess the level of p38 MAPK activation. In some embodiments, flow cytometry can be used.

In some cases, the potential antagonist function of an anti B7-H1 antibody can be tested by determining whether the antibody can block the binding of PD-1 protein to B7-H1 expressed by tumor cells in vitro, or whether it can block B7-H1-mediated T cell apoptosis or apoptotic signaling in vitro. See, e.g., Dong et al., (2002) *Nature Med* 8 (8):793-800; and Gibbons et al. (2012) *Oncoimmunol* 1 (7):1061-1073.

Figure 16:
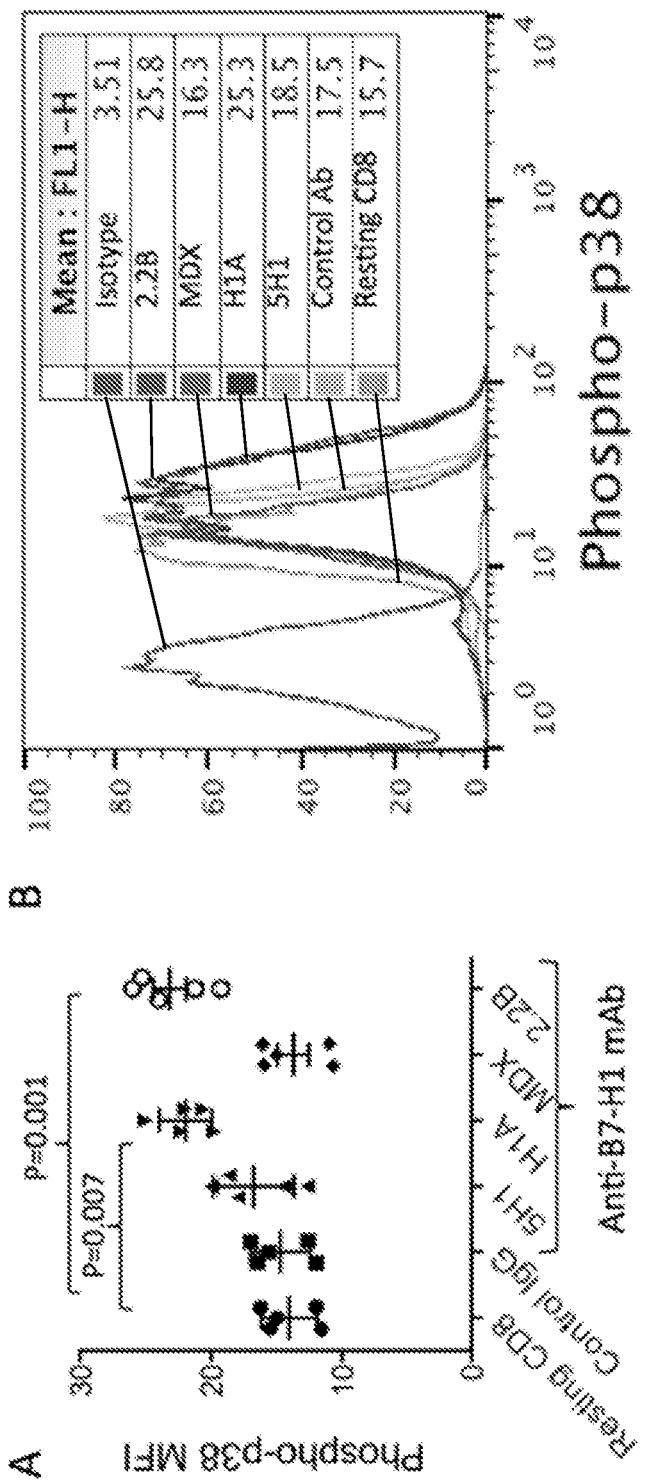
FIGS. 16A and 16B show that ligation of B7-H1 in human T cells incubated with various anti-B7-H1 mAbs or control Ab in the presence of anti-CD3/CD28 beads led to increased activation of p38 MAPK.

As discussed below, for example, three anti-mouse B7-H1 antibodies (10B5, 9G2 and MIH5) were identified as having antagonistic function, and two of those (9G2 and MIH5) also were identified as having agonistic function. See, Example 9 and FIG. 21. In contrast, 10B5 was found to have only antagonistic function, and no agonistic activity. Three anti-human B7-H1 antibodies (5H1, H1A, and 2.2B) also were evaluated. Of these, 5H1 had only antagonistic function, while H1A and 2.2B had only agonistic activity. See, Example 9 and FIG. 16.

Antibodies against B7-H1 can be incorporated into pharmaceutical compositions for treatment of cancer or other diseases (e.g., autoimmune disorders or pathogenic infections). Thus, this document also provides for the use of such molecules in the manufacture of medicaments for treating clinical conditions such as cancer, pathogenic infections, or autoimmune disorders. The compositions can further include one or more pharmaceutically acceptable carriers, diluents and/or adjuvants. The potency of the pharmaceutical compositions provided herein typically is based on the binding of the antibody to B7-H1.

A "pharmaceutically acceptable carrier" (also referred to as an "excipient" or a "carrier") is a pharmaceutically acceptable solvent, suspending agent, stabilizing agent, or any other pharmacologically inert vehicle for delivering one or more therapeutic compounds to a subject, which is nontoxic to the cell or mammal being exposed thereto at the dosages and concentrations employed. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers that do not deleteriously react with amino acids include, by way of example and not limitation: water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Pharmaceutically acceptable carriers also include aqueous pH buffered solutions or liposomes (small vesicles composed of various types of lipids, phospholipids and/or surfactants which are useful for delivery of a drug to a mammal). Further examples of pharmaceutically acceptable carriers include buffers such as phosphate, citrate, and other organic acids, antioxidants such as ascorbic acid, low molecular weight (less than about 10 residues) polypeptides, proteins such as serum albumin, gelatin, or immunoglobulins, hydrophilic polymers such as polyvinylpyrrolidone, amino acids such as glycine, glutamine, asparagine, arginine or lysine, monosaccharides, disaccharides, and other carbohydrates including glucose, mannose or dextrins, chelating agents such as EDTA, sugar alcohols such as mannitol or sorbitol, salt-forming counterions such as sodium, and/or nonionic surfactants such as TWEEN™, polyethylene glycol (PEG), and PLURONICS™.

Pharmaceutical compositions can be formulated by mixing one or more active agents with one or more physiologically acceptable carriers, diluents, and/or adjuvants, and optionally other agents that are usually incorporated into formulations to provide improved transfer, delivery, tolerance, and the like. A pharmaceutical composition can be formulated, e.g., in lyophilized formulations, aqueous solutions, dispersions, or solid preparations, such as tablets, dragees or capsules. A multitude of appropriate formulations can be found in the formulary known to all pharmaceutical chemists: *Remington's Pharmaceutical Sciences* (18th ed, Mack Publishing Company, Easton, Pa. (1990)), particularly Chapter 87 by Block, Lawrence, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies as described herein, provided that the active agent in the formulation is not inactivated by the formulation and the formulation is physiologically compatible and tolerable with the route of administration. See, also, Baldrick (2000) *Regul Toxicol Pharmacol* 32:210-218; Wang (2000) *Int J Pharm* 203:1-60; Charman (2000) *J Pharm Sci* 89:967-978; and Powell et al. (1998) *PDA J Pharm Sci Technol* 52:238-311), and the citations therein for additional information related to formulations, excipients and carriers well known to pharmaceutical chemists.

Pharmaceutical compositions include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Compositions and formulations can include sterile aqueous solutions, which also can contain buffers, diluents and other suitable additives (e.g., penetration enhancers, carrier compounds and other pharmaceutically acceptable carriers). Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions provided herein. The formulations can be sterilized if desired.

In some embodiments, a composition containing an antibody against B7-H7 can be in the form of a solution or powder with or without a diluent to make an injectable suspension. The composition may contain additional ingredients including, without limitation, pharmaceutically acceptable vehicles, such as saline, water, lactic acid, mannitol, or combinations thereof, for example.

Methods for using an anti B7-H1 antibody or a composition containing an anti B7-H1 antibody to treat a clinical condition in a subject also are provided herein. The methods can include, for example, administering an anti B7-H1 antibody to a subject identified as being in need thereof, where the subject has a clinical condition (e.g., cancer, a pathogenic infection, or an autoimmune disorder) in which modulation of T cell survival or activity may be beneficial, and where the antibody is identified as having antagonistic and/or agonistic activity with regard to B7-H1. For example, an anti B7-H1 antibody with antagonistic but not agonistic activity (or predominantly antagonistic activity) can be useful for treating a clinical condition (e.g., cancer or a pathogenic infection) in which it is desired to reduce or inhibit B7-H1-mediated inhibition of T cell function and survival. Alternatively, an anti B7-H1 antibody with agonistic but not antagonistic activity (or predominantly agonistic activity) can be useful for treating a clinical condition (e.g., an autoimmune disorder) in which it is desired to increase B7-H1/PD-1-mediated inhibition of T cell function and survival. It is to be noted that antibodies with both agonistic and antagonistic effects also can be useful in the methods of treatment provided herein, particularly where an antibody has predominantly antagonistic or predominantly agonistic effects. An antibody can be considered to have "predominantly" antagonistic effects when it acts more strongly as an antagonist than an agonist, so that the overriding effect is an inhibition of B7-H1-mediated inhibition of T cell function and survival. Conversely, an antibody can be considered to have "predominantly" agonistic effects when it acts more strongly as an agonist than an antagonist, so that the overriding effect is a decrease of B7-H1-mediated T cell survival.

Any appropriate method can be used to administer an anti-B7-H1 antibody or a composition as described herein to a mammal. Administration can be, for example, parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, administration can be topical (e.g., transdermal, sublingual, ophthalmic, or intranasal), pulmonary (e.g., by inhalation or insufflation of powders or aerosols), or oral. In addition, a composition containing an antibody or fusion protein as described herein can be administered prior to, after, or in lieu of surgical resection of a tumor.

A composition containing an antibody against B7-H1 can be administered to a mammal in any appropriate amount, at any appropriate frequency, and for any appropriate duration effective to achieve a desired outcome (e.g., to increase progression-free survival or to increase the number of naturally-occurring tumor-reactive CD8+ T cells in a cancer patient). In some embodiments, for example, a composition containing an anti-B7-H1 antibody can be administered to a mammal having cancer to reduce the progression rate of the cancer by 5, 10, 25, 50, 75, 100, or more percent. For example, the progression rate can be reduced such that no additional cancer progression is detected. In some embodiments, a composition containing an anti B7-H1 antibody can be administered to a mammal having cancer under conditions where progression-free survival is increased (e.g., by 5, 10, 25, 50, 75, 100, or more percent) as compared to the median progression-free survival of corresponding mammals having untreated cancer or the median progression-free survival of corresponding mammals having cancer and treated with other therapies (e.g., chemotherapeutic agents). Progression-free survival can be measured over any length of time (e.g., one month, two months, three months, four months, five months, six months, or longer). Any appropriate method can be used to determine whether or not the progression rate of cancer is reduced. For skin cancer (e.g., melanoma), for example, the progression rate can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer after treatment can be determined and compared to the stage before treatment to determine whether or not the progression rate has been reduced.

An effective amount of a composition containing an antibody as provided herein can be any amount that reduces a symptom of the condition being treated, without significant toxicity. With cancer, for example, an effective amount can reduce the progression rate of the cancer, increase the progression-free survival rate, or increase the median time to progression. Optimum dosages can vary depending on the relative potency of individual polypeptides (e.g., antibodies and fusion proteins), and can generally be estimated based on $EC_{50}$ found to be effective in in vitro and in vivo animal models. Typically, dosage is from 0.01 µg to 100 g per kg of body weight. For example, an effective amount of an antibody or fusion protein can be from about 1 mg/kg to about 100 mg/kg (e.g., about 5 mg/kg, about 10 mg/kg, about 20 mg/kg, about 50 mg/kg, or about 75 mg/kg). If a particular subject fails to respond to a particular amount, then the amount of the antibody can be increased by, for example, two fold. After receiving this higher concentration, the subject can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the clinical condition may require an increase or decrease in the actual effective amount administered.

The frequency of administration can be, for example, once or more daily, biweekly, weekly, monthly, or even less. The frequency of administration can remain constant or can be variable during the duration of treatment. A course of treatment can include rest periods. For example, a composition containing an antibody as provided herein can be administered over a first period of time, followed by a rest period, and such a regimen can be repeated one or more times. As with the effective amount, various factors can influence the actual frequency of administration used for a particular application. For example, the effective amount, duration of treatment, use of multiple treatment agents, route of administration, and severity of the clinical condition may require an increase or decrease in administration frequency.

After administering an anti B7-H1 antibody to a subject, the subject can be monitored to determine whether or not the clinical condition has improved. For example, a cancer patient can be assessed after treatment to determine whether or not the progression of the cancer has been reduced (e.g., stopped). Any method, including those that are standard in the art, can be used to assess progression and survival rates.

The invention will be further described in the following examples, which do not limit the scope of the invention described in the claims.

EXAMPLES

Figure 2:
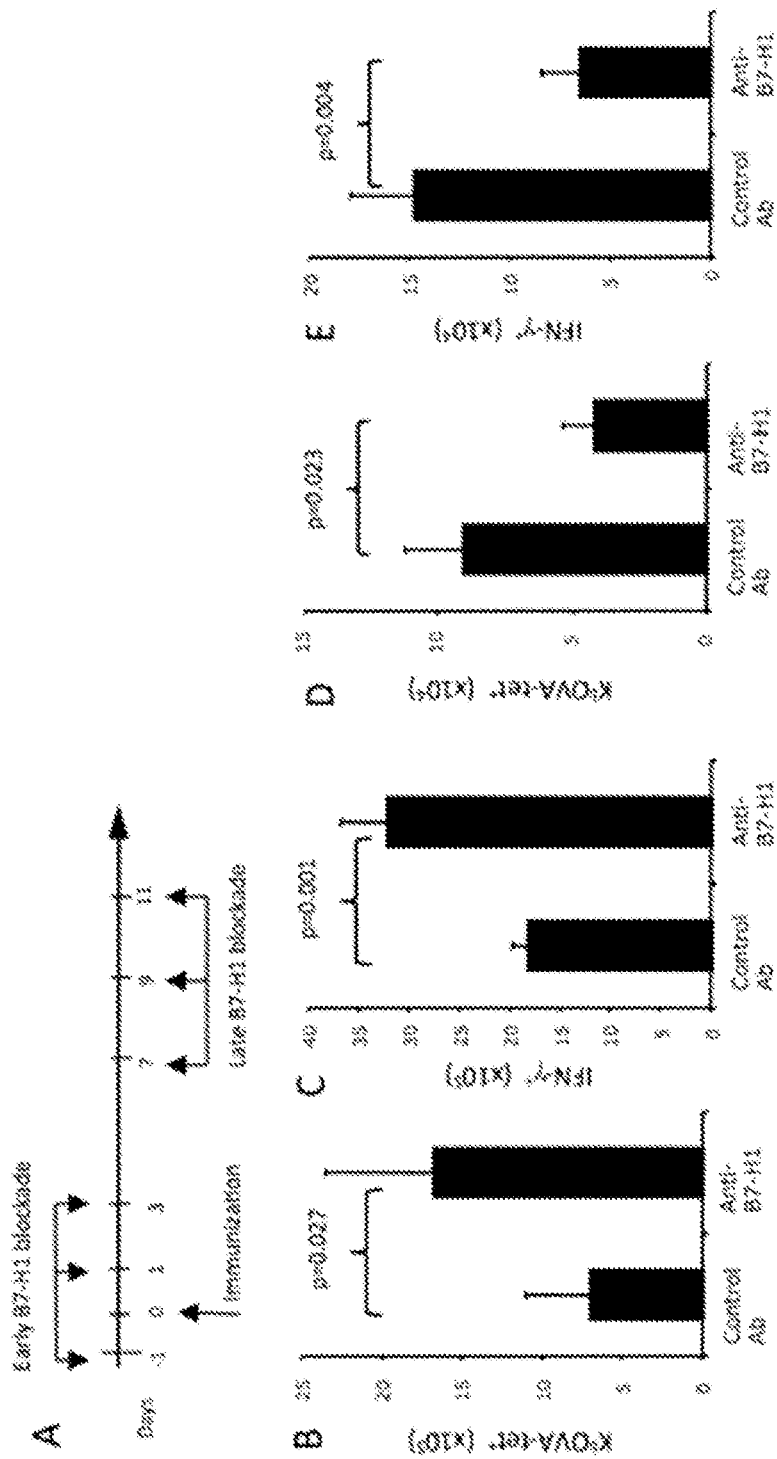
FIG. 2A is a schematic depicting early vs. late B7-H1 blockade methods.
FIGS. 2B-2E are a series of graphs plotting the effects of late B7-H1 blockade on the numbers of effector CD8 T cells. C57BL/6 mice were immunized with OVA protein/poly I:C. Spleen cells were isolated 7 days after the last injection of antibodies and analyzed for KbOVA tetramer (tet) binding and intracellular IFN-γ production. Graphs show the average numbers of tetramer$^+$ (FIG. 2B) and IFN-γ$^+$ (FIG. 2C) CD8 T cells after early blockade, and the average numbers of tetramer$^+$ (FIG. 2D) and IFN-γ$^+$ (FIG. 2E) CD8 T cells after late blockade.

Example 1—Late Blockade of B7-H1 Reduces the Numbers of Effector CD8 T Cells Following Immunization In an attempt to identify the optimal timing of B7-H1 blockade to improve T cell responses, anti-B7-H1 blocking antibody was administered either during an early (days 0-3) or a late (days 7-10) stage following immunization (FIG. 2A). These time periods were set according to the kinetics of T cell response following ovalbumin (OVA) and poly (I:C) immunization (Ahonen et al., *J Exp Med* 199:775-784, 2004). Early B7-H1 blockade greatly increased the expansion of OVA antigen specific ($K^b$OVA tetramer$^+$) and functional IFN-$\gamma^+$ CD8 T cells in spleens of immunized mice (FIGS. 2B and 2C). Unexpectedly, late B7-H1 blockade decreased the percentages and numbers of antigen specific (tetramer$^+$) and effector (IFN-$\gamma^+$) CD8 T cells in the spleens of mice (FIGS. 2D and 2E). Taken together, the results of early blockade of B7-H1 are consistent with an inhibitory role of B7-H1 expressed by antigen presenting cells (dendritic cells) during the early stage of T cell priming (Pulko et al., *J Immunol* 183:3634-3641, 2009; and Farley et al., *Mol Cell Biol* 26:2118-2129, 2006). However, the opposite effects of late B7-H1 blockade indicate an unknown function of B7-H1 expressed by activated/effector T cells during the late stage of T cell responses (Pulko 2011, supra).

Figure 3:
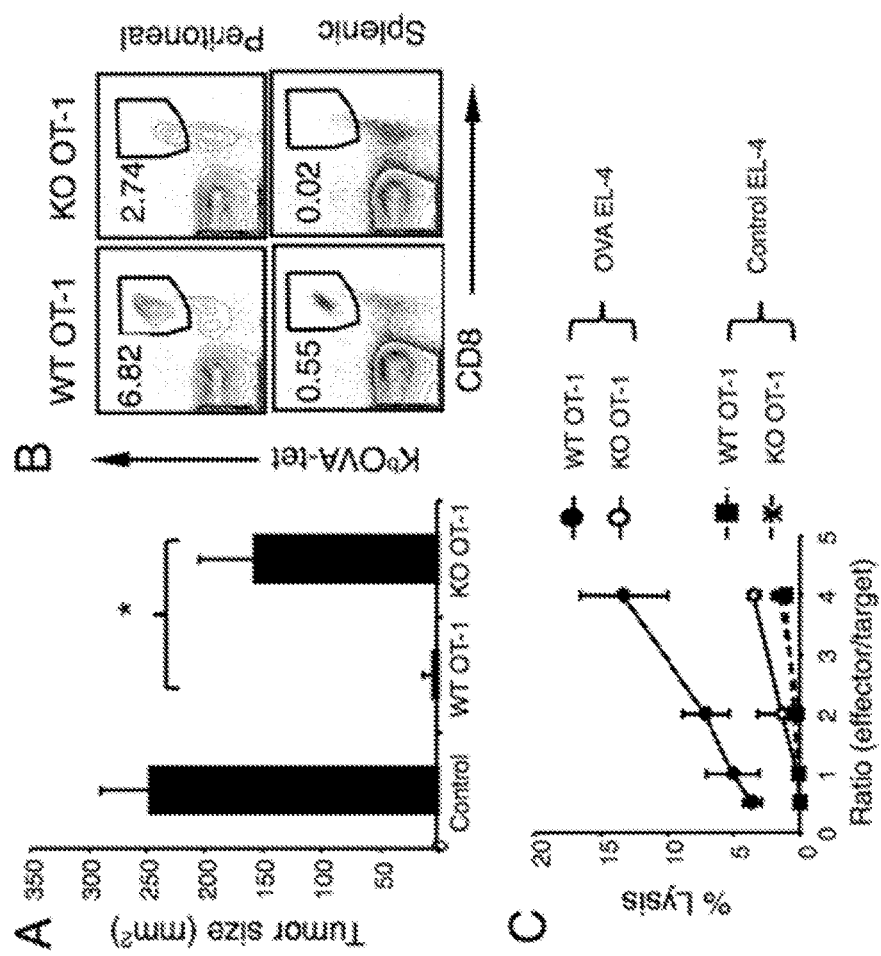
FIGS. 3A-3C show that B7-H1 deficient CD8 T cells exhibited impaired protective immunity against tumor challenge.

Example 2—B7-H1 Deficient Effector CD8 T Cells Fail to Mount a Protective Immunity The ability of B7-H1-deficient effector CD8 T cells to mount protective immunity against tumor challenge was examined. WT and B7-H1 KO effector OT-1 CD8 T cells (with TCR specific for OVA antigen) were transferred (i.v.) into recipient mice one day before injection of B16-OVA tumor cells. While B16-OVA tumors progressively grew in the control group of mice without effector T cells transfer, they did not grow out in the mice that received WT effector CD8 T cells (FIG. 3A). However, the growth of B16-OVA tumors could not be completely suppressed in mice transferred with B7-H1 KO effector CD8 T cells (FIG. 3A, $p<0.05$), suggesting that B7-H1 deficient effector CD8 T cells may have compromised protective function. It also was observed that the frequency and numbers of $K^b$OVA-tet$^+$ CD8 T cells decreased by 2-5-fold at the tumor sites and spleens of recipients of B7-H1 KO CD8 T cells compared to recipients of WT CD8 T cells (FIG. 3B, $p<0.05$). In addition, the cytolytic activity in the spleens of recipients of B7-H1 KO CD8 T cells decreased by 4-7 fold compared to recipients of WT CD8 T cells (FIG. 3C). Taken together, these results suggested that B7-H1 deficient effector CD8 T cells could not mount protective immunity due to compromised cytolytic activity resulting from their reduced accumulation.

Example 3—More Apoptosis by B7-H1 Deficient T Cells Following Initial Proliferation To directly identify the function of B7-H1 expressed by CD8 T cells, B7-H1 deficient, OT-1 TCR transgenic mice were produced. These mice had CD8 T cells carrying OVA-specific TCR, but did not express B7-H1 (Pulko 2011, supra). Proliferation to antigen stimulation was examined in vitro and in vivo. Naïve B7-H1 KO and WT CD8 OT-1 T cells were found to undergo similar antigen-stimulated proliferation in vitro.

Figure 4:
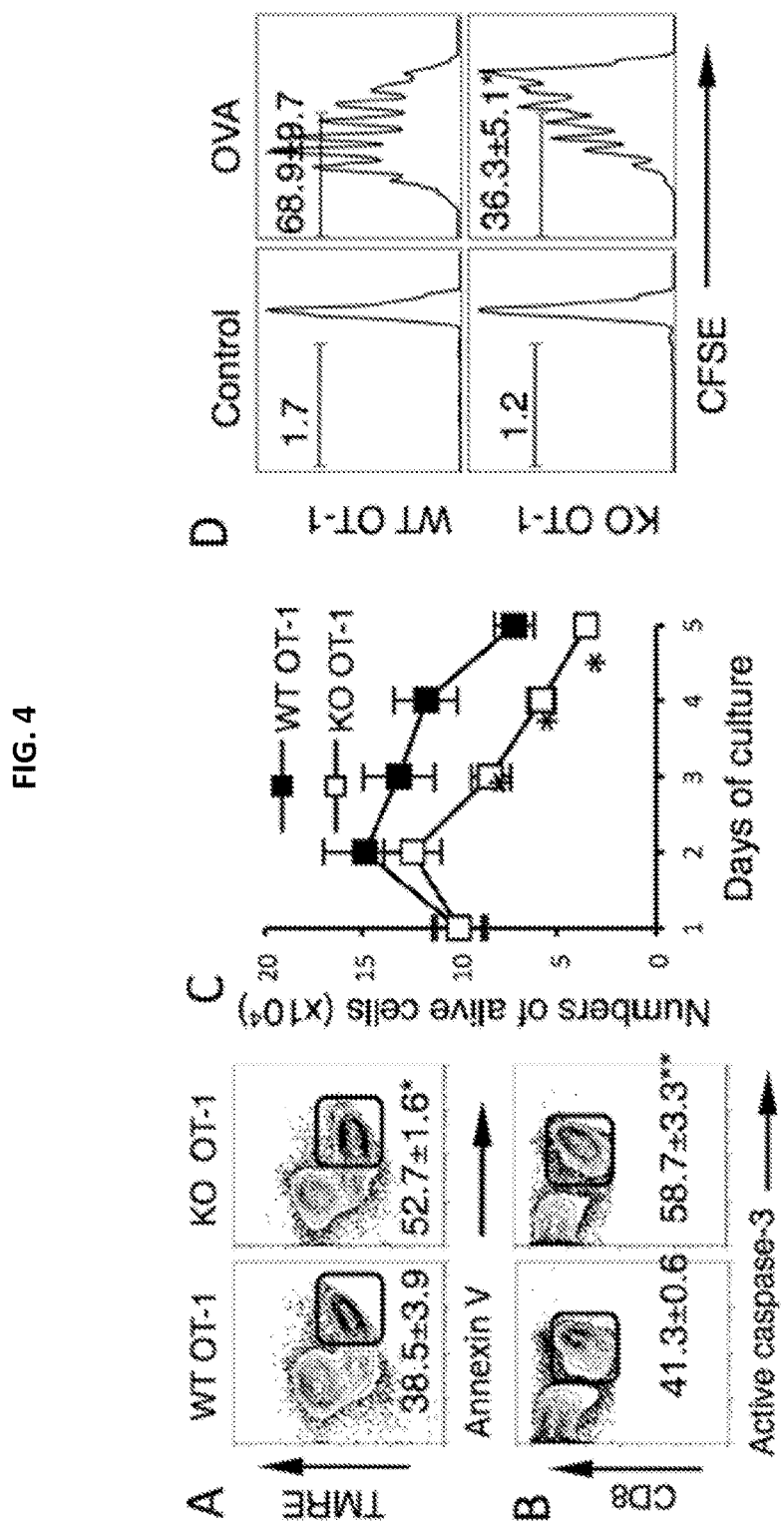
FIGS. 4A-4D demonstrate increased apoptosis of B7-H1 deficient CD8 T cells following antigen stimulation.

Next, studies were conducted to ascertain whether they differed in spontaneous apoptosis. Freshly isolated WT and B7-H1 KO CD8 T cells underwent comparably low levels of spontaneous apoptosis, as demonstrated by similar levels of Annexin V binding, TMRE staining (a barometer of mitochondrial transmembrane potential, which decreases during apoptosis; Veuger et al., *Cancer Res* 63:6008-6015, 2003), and active caspase-3 levels (Pulko 2011, supra). However, when stimulated with antigen (OVA), B7-H1 KO CD8 T cells underwent more apoptosis than WT CD8 T cells, as demonstrated by annexin V$^+$ and TMRE$^{low}$ staining (FIG. 4A) and increased levels of active caspase-3 (FIG. 4B). Accordingly, the numbers of viable B7-H1 KO CD8 T cells had about a 2-fold decrease between days 3-5 after activation (FIG. 4C).

To examine whether increased death of B7-H1 KO CD8 T cells was due to impaired proliferation, CD8 T cells were labeled with carboxyfluorescein succinimidyl ester (CFSE; an intracellular dye for tracking cell division). On day 3 post antigen stimulation, B7-H1 KO and WT OT-1 CD8 T cells underwent similar proliferation (up to 6 divisions), but the percentage of B7-H1 KO CD8 T cells that underwent 3 or more divisions decreased by about 2-fold compared to WT CD8 T cells (FIG. 4D). These results suggested that B7-H1 deficient CD8 T cells undergo normal initial proliferation, but there is not a net increase in the population due to increased apoptosis.

Example 4—Fewer B7-H1 Deficient T Cells Survived the Contraction Phase in Vivo

Figure 5:
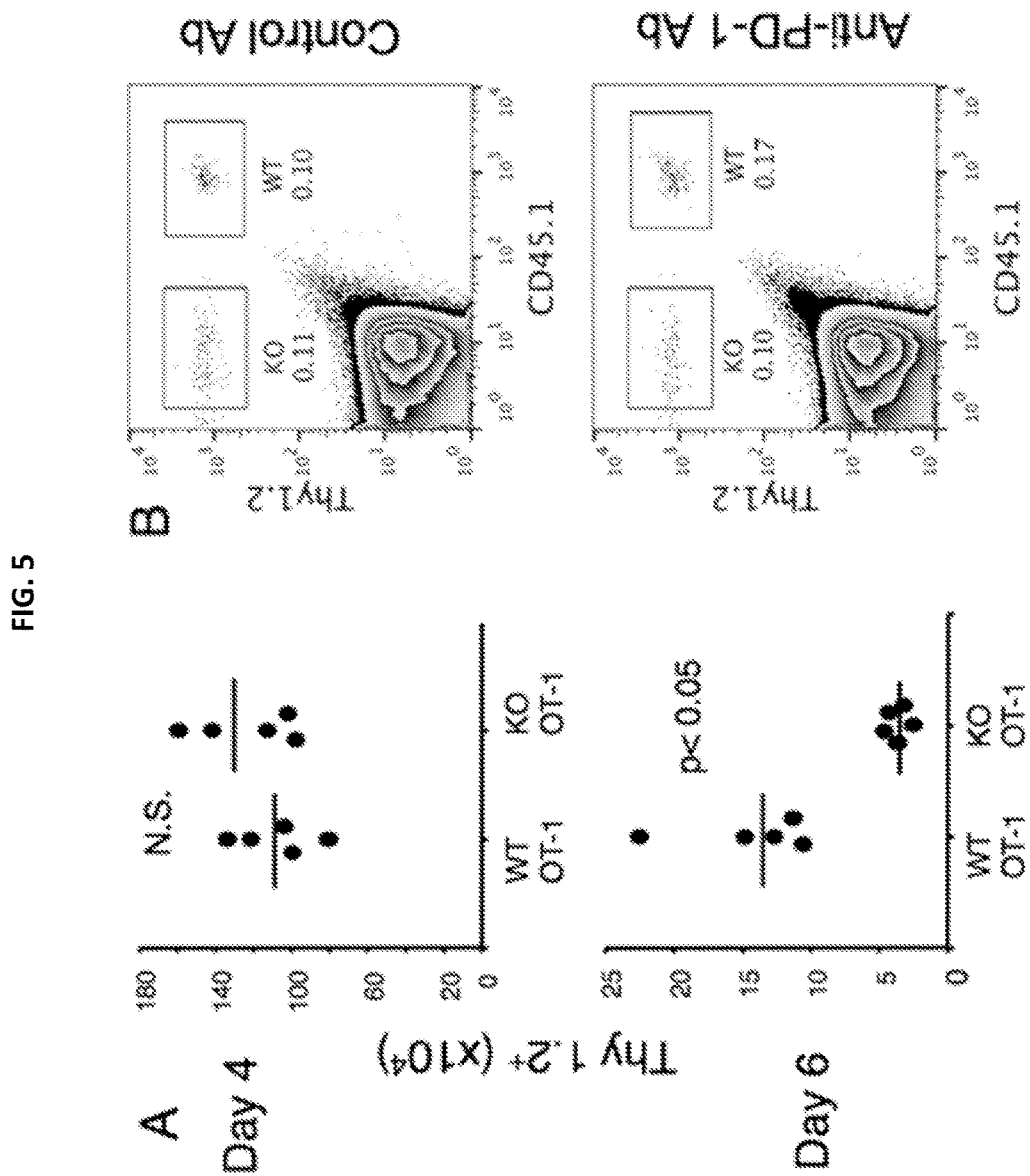
FIGS. 5A and 5B indicate a T cell intrinsic function of B7-H1 in T cell contraction.

To further investigate the role of B7-H1 expressed by antigen-specific CD8 T cells in vivo, WT or B7-H1 KO OT-1 CD8 (Thy1.2$^+$) cells were transferred into congenic (Thy1.1$^+$) B6 mice, followed by OVA/poly (I:C) immunization. Similar primary expansion of WT and B7-H1 KO CD8 T cells was observed in the spleens of immunized mice on day 4, but on day 6, B7-H1 KO OT-1 CD8 T cells exhibited more contraction than WT OT-1 CD8 T cells in both frequency and total numbers (FIG. 5A). To confirm this was a T cell intrinsic effect of B7-H1, the same numbers of preactivated WT and B7-H1 KO T cells (1:1) were co-transferred into the same host and anti-PD-1 blocking antibody or control antibody was injected with T cell transfer. If the prosurvival function of B7-H1 requires its ligation with PD-1, an anti-PD-1 antibody that blocks PD-1/B7-H1 ligation would cause a reduction in WT T cells but not in B7-H1 KO T cells (internal control). As shown in FIG. 5B, anti-PD-1 did not dramatically change the percent of WT T cells compared with control antibody, nor did it change the ratio with B7-H1 KO T cells, suggesting that B7-H1 does not need ligation with PD-1 to provide pro-survival function for T cells during contraction. These data thus indicated that T cell intrinsic B7-H1 is required for T cell survival during contraction.

Taken together, the above studies suggested a previously unknown function for B7-H1 expressed by T cells, and support the central hypothesis that B7-H1 expressed by activated CD8 T cells has an intrinsic pro-survival function that is required for establishment of T cell immunity, and ligation of B7-H1 by agonistic antibody may disrupt its pro-survival function in T cells. The studies discussed below are conducted to identify the mechanisms for B7-H1's function as an intrinsic pro-survival factor for activated T cells, to investigate the role of B7-H1 in T cell differentiation, and to find ways to evaluate the impact of agonistic B7-H1 antibodies in T cell function. By understanding the downstream signaling pathways of B7-H1, new subcellular targets for regulating T cell survival can be developed, and optimal B7-H1 antibodies can be selected to improve protective T cell immunity against cancers and pathogen infections.

Example 5—Defining the T Cell-Intrinsic Role of B7-H1 in T Cell Survival

The idea that B7-H1 has a T cell-intrinsic pro-survival function is a new concept in the field of B7-H1 biology, distinct from traditional studies into B7-H1-PD1 receptor interactions that promote apoptosis of PD-1$^+$ T cells (Gibbons et al., supra; and Keir et al., Annu Rev Immunol 26:677-704, 2008). Thus, B7-H1 might use a previously unknown signaling pathway to mediate its T cell pro-survival function. The experiments in this example are carried out to investigate how B7-H1 regulates pro-survival molecule Bcl-xL via the p38 MAPK pathway, and to investigate the role of DNA-PKcs (which was more recently identified as a B7-H1-associated protein) in T cell survival. T cell apoptosis can be triggered by intrinsic (mitochondria-based) and extrinsic (receptor-based) stimuli (Bouillet and O'Reilly, Nat Rev Immunol 9:514-519, 2009). As B7-H1 deficiency does not affect the expression of Fas or Fas ligand in T cells (Pulko 2011, supra), these studies focus on defining how B7-H1 affects intrinsic or mitochondria-based apoptosis.

Figure 6:
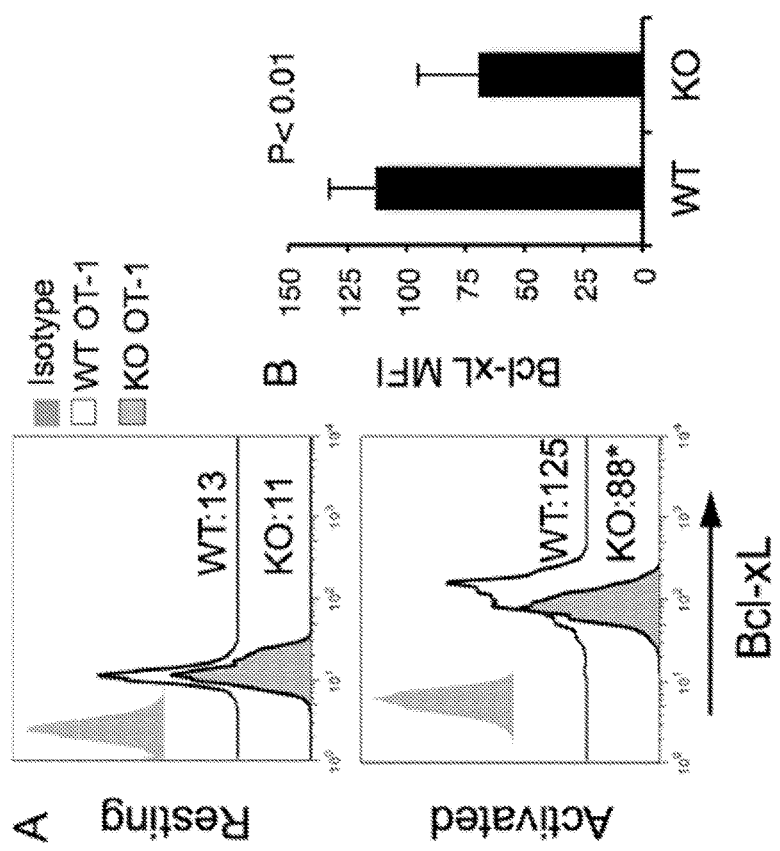
FIGS. 6A and 6B demonstrate lower Bcl-xL expression by B7-H1 KO T cells.

The Bcl-2 family is a group of proteins that coordinately control apoptotic cell death by regulating mitochondrial cytochrome c. This family includes both pro-apoptotic and anti-apoptotic members. Preliminary studies examined the levels of Bcl-2 family members (Bcl-2, Bcl-xL, and Bim) in both resting and activated T cells. Intracellular staining revealed similar levels of Bcl-2, Bcl-xL, and Bim in resting WT and B7-H1 KO CD8 T cells (FIG. 6A). In activated T cells, however, Bcl-xL levels were significantly lower in B7-H1 KO CD8 T cells than in WT CD8 T cells (FIGS. 6A and 6B, p<0.01). The finding that the loss of B7-H1 is correlated with lower levels of Bcl-xL was both novel and unexpected, because it had been believed that B7-H1 functions as a suppressive regulator for T cells (Keir et al., supra). Since B7-H1 ligation by PD-1 did not affect Bcl-xL expression (Pulko 2011, supra), it is possible that B7-H1 regulates Bcl-xL in an intrinsic manner. The experiments described in this section will (1) examine the expression, function, and (2) phosphorylation of Bcl-xL in T cells in the absence of B7-H1 signaling.

Unlike Bcl-2 protein, which is constitutively expressed by T cells, Bcl-xL protein levels vary with levels of T cell activation (Boise et al., Immunity 3:87-98, 1995). Its expression is induced by TCR stimulation and up-regulated by CD28 signals. Bcl-xL expression is not stable, however, and it begins to decline at 48 h after activation. Bcl-xL loses its pro-survival function through phosphorylation by p38 MAPK (Farley et al., supra; and Kharbanda et al., J Biol Chem 275:322-327, 2000). In fact, activation of p38 MAPK prevents mitochondria accumulation of Bcl-xL and induces apoptosis of CD8 T cells in vivo (Farley et al., supra; and Merritt et al., Mol Cell Biol 20:936-946, 2000). Thus, it is possible that the decrease of Bcl-xL in B7-H1 KO T cells could be due to increased activation of p38 MAPK.

Figure 7:
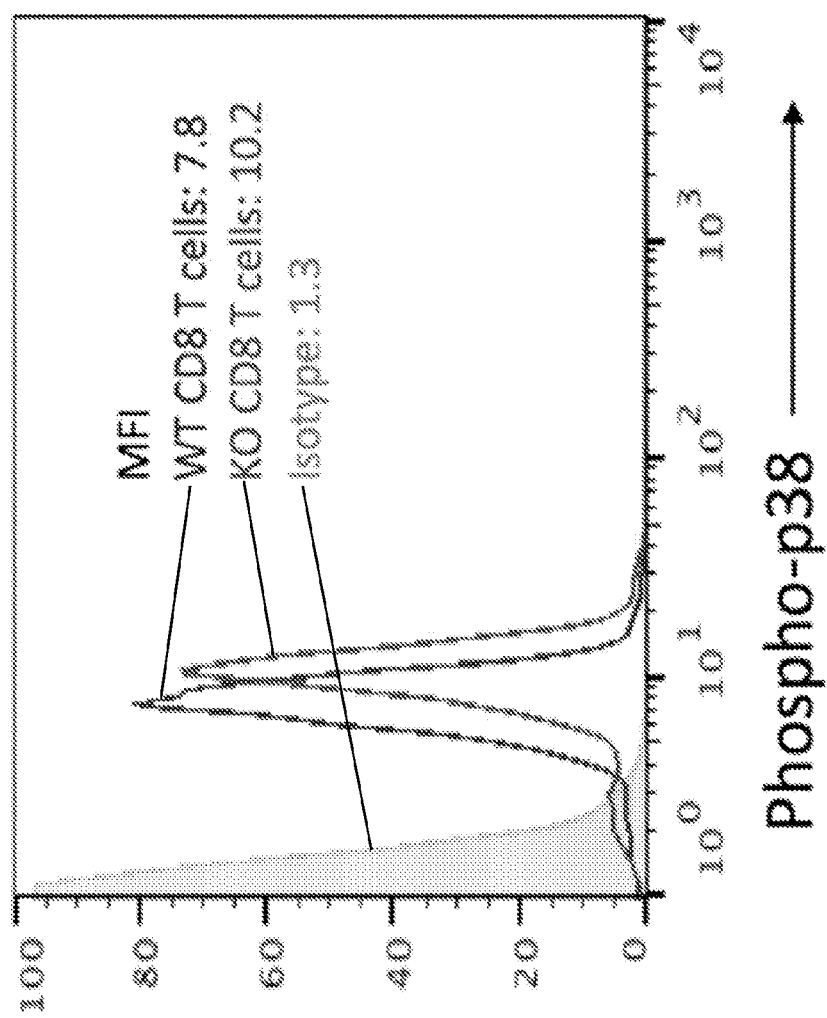
FIG. 7 is a graph plotting p38 MAPK activation, which was increased in the absence of B7-H1. T cells isolated from WT or B7-H1 KO mice were activated with anti-CD3/CD28 beads for 48 hours. Data show the histogram of phosphor-p38 MAPK expression.
Figure 8B:
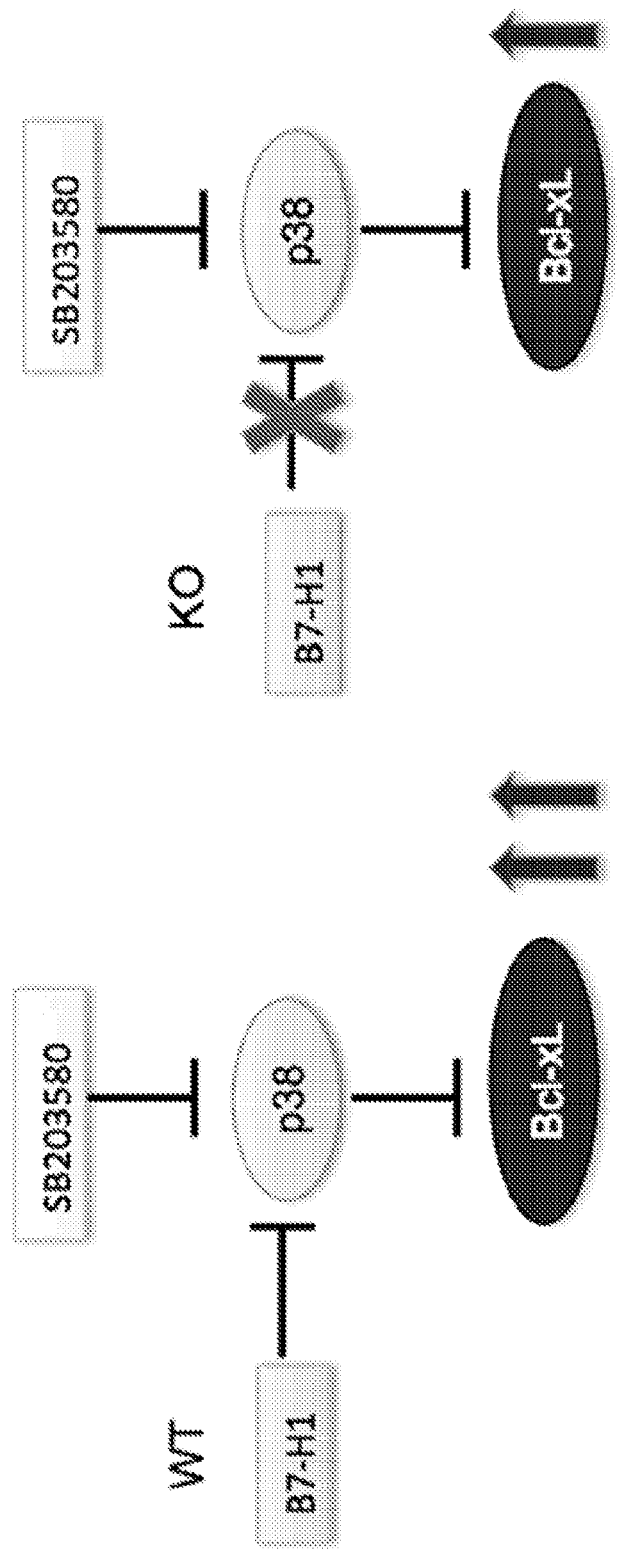

To test this possibility, activation of p38 MAPK was measured in B7-H1 KO T cells. The data of FIG. 7 show that the activation of p38 MAPK increased in B7-H1 deficient T cells compared to WT T cells, suggesting a potential regulatory role of B7-H1 in activation of p38. The degree p38 MAPK to which contributes to Bcl-xL levels was tested in WT and B7-H1 KO T cells. Since activation of p38 MAPK led to degradation of Bcl-xL (Farley et al., supra; and Kharbanda et al., supra), p38 MAPK inhibitor SB203580 (a specific pharmacological inhibitor of p38 MAPK) was used to test whether inhibition of p38 MAPK would increase Bcl-xL levels in activated T cells. The results of FIG. 8A show that inhibition of p38 MAPK increased the levels of Bcl-xL in WT T cells. Interestingly, the percent of increase of Bcl-xL was higher in WT T cells compared with B7-H1 KO T cells (p<0.01). These data suggested that B7-H1 could be a negative regulator of p38 MAPK activation. As diagrammed in FIG. 8B, in activated WT T cells, p38 MAPK was under the negative regulation of B7-H1 while Bcl-xL was under the negative control of p38 MAPK. When SB203580 was added, p38 MAPK was negatively regulated by at least two factors: B7-H1 and SB203580. Thus, Bcl-xL was released from p38 MAPK suppression and increased dramatically in activated WT T cells. However, in the absence of B7-H1, as in B7-H1 KO T cells, inhibition of p38 MAPK by SB203580 did not increase as much as in WT T cells.

Example 6—Determining Whether B7-H1 Stabilizes Bcl-xL Levels Via p38 MAPK

Based on the above data, it was hypothesized that B7-H1 stabilizes Bcl-xL levels by regulating activation of p38 MAPK pathway. The following experiments are performed to test this hypothesis.

First, degradation of Bcl-xL in the absence of B7-H1 is examined. Since phosphorylation of Bcl-xL leads to its degradation, experiments are conducted to test whether phosphorylation of Bcl-xL increases in the absence of B7-H1. The phosphorylation of Bcl-xL in WT and B7-H1 KO activated CD8 T cells is compared. Intracellular staining and Western blotting are performed to assess phospho-Bcl-xL expression (Millipore AB3116 specific for the Bcl-xL phosphorylated on serine 62) following CD8 T cell activation by anti-CD3/CD28 antibody for 5, 10, 30, and 60 minutes.

Second, p38 activity in the absence of B7-H1 is examined. In particular, the function of p38 MAPK from B7-H1 WT and KO T cells in phosphorylation of Bcl-xL is evaluated. To directly measure whether p38 MAPK activation increases in B7-H1 KO T cells and results in elevated phosphorylation of Bcl-xL, in vitro kinase assays are performed using recombinant Bcl-xL (ProSpec, East Brunswick, N.J.) as a substrate. Total p38 MAPK is immunoprecipitated from whole-cell lysates of B7-H1 WT or KO CD8 T cells (naïve or activated), and then incubated with recombinant Bcl-xL in vitro. To confirm that phosphorylation of Bcl-xL in vitro is directly mediated by activated p38 MAPK, SB203580 is used in this system.

In addition, studies are conducted to determine whether enhanced expression of Bcl-xL rescues T cell apoptosis and contraction of B7-H1 KO T cells. B7-H1 KO mice are bred into Bcl-xL transgenic mice (provided by Dr. Shapiro of Mayo Clinic Rochester). T cell apoptosis and contraction are compared in vitro and in vivo between Bcl-xL Tg and non-Bcl-xLTg B7-H1 KO T cells using models as in the preliminary studies.

Further studies are conducted to provide insights into mechanisms by which B7-H1 regulates T cell survival, and particularly to determine whether inhibition of p38 MAPK affects T cell apoptosis and contraction of B7-H1 KO T cells. In particular, T cell apoptosis and contraction are compared in vitro and in vivo between B7-H1 KO T cells pre-incubated with SB203580 using models as in the preliminary experiments. Given the pro-survival function of B7-H1 expressed by activated T cells, B7-H1 may stabilize protein levels of Bcl-xL by preventing phosphorylation of Bcl-xL via inhibition of p38 MAPK activation. Accordingly, increased phosphorylation of BclxL and increased activity of p38 MAPK may be observed in B7-H1 KO T cells compared with WT T cells, and introduction of Bcl-xL transgene or inhibition of p38 MAPK may rescue B7-H1 KO T cells from apoptosis and contraction.

An alternative pathway of Bcl-xL degradation could involve ubiquitination of Bcl-xL (Niture and Jaiswal, *J Biol Chem* 286:44542-44556, 2011). If B7-H1 signaling data do not support a role for regulation of phosphorylation of Bcl-xL, the extent of ubiquitination of Bcl-xL is examined in B7-H1 KO T cells and WT T cells. Taken together, the results of these studies provide knowledge about how T cell survival and contraction are regulated by the B7-H1/p38 MAPK/Bcl-xL pathway, and facilitate the design of new immune adjuvants to promote T cell survival following antigen stimulation.

Example 7—Defining the Role of DNA-PKcs in B7-H1-Mediated T Cell Survival

B7-H1 is a transmembrane protein consisting of extracellular, transmembrane, and intracellular domains. The extracellular domain (ECD) of B7-H1 interacts with receptors PD-1 and CD80 expressed by activated T cells (Wang et al., *J Exp Med* 197:1083-1091, 2003). The intracellular domain (ICD) has the potential to deliver intrinsic anti-apoptotic signals (Azuma et al., *Blood* 111:3635-3643, 2008). It is not clear, however, how ICD mediates B7-H1's pro-survival function. To define the downstream signaling pathway of B7-H1, intracellular binding protein(s) of B7-H1 are identified.

Figure 9:
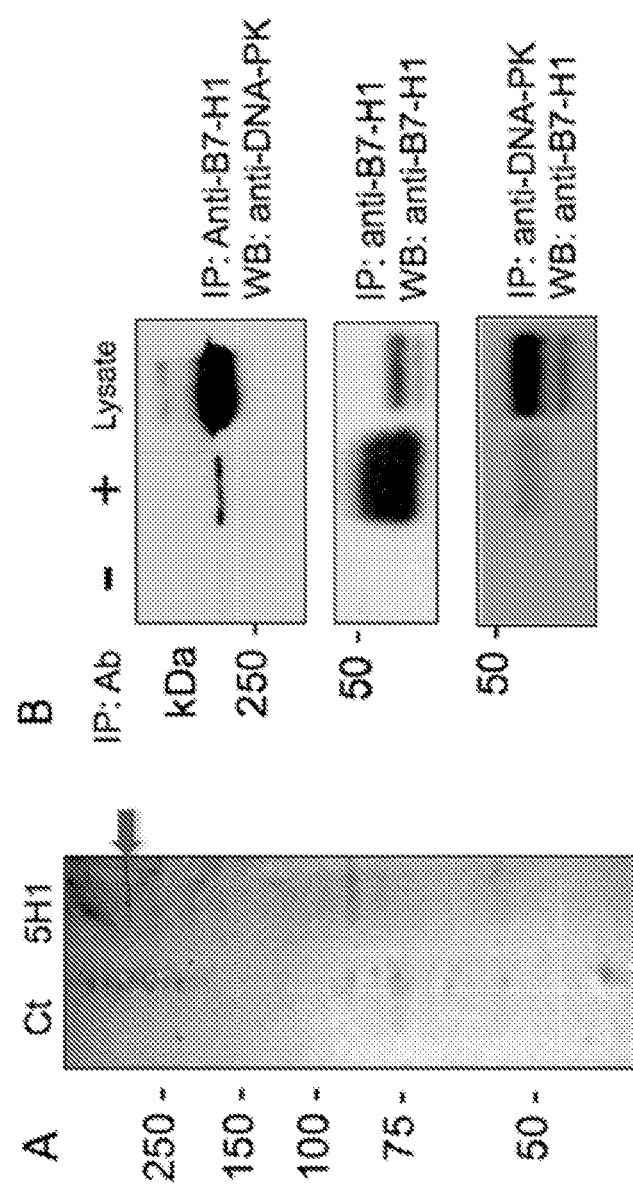
FIGS. 9A and 9B are pictures of Western blots showing B7-H1 associated protein DNA-PKcs in T cells. For FIG. 9A, immunoprecipitation (IP) with cell lysate of Kaspas299 was performed with anti-B7-H1 mAb (5H1) or control Ab (Ct). For FIG. 9B, IP with anti-B7-H1 or anti-DNA-PK (H106) antibody was followed by Western blotting (WB) with either anti-B7-H1 or anti-DNAPK. Whole cell lysate was used as input.
Figure 10:
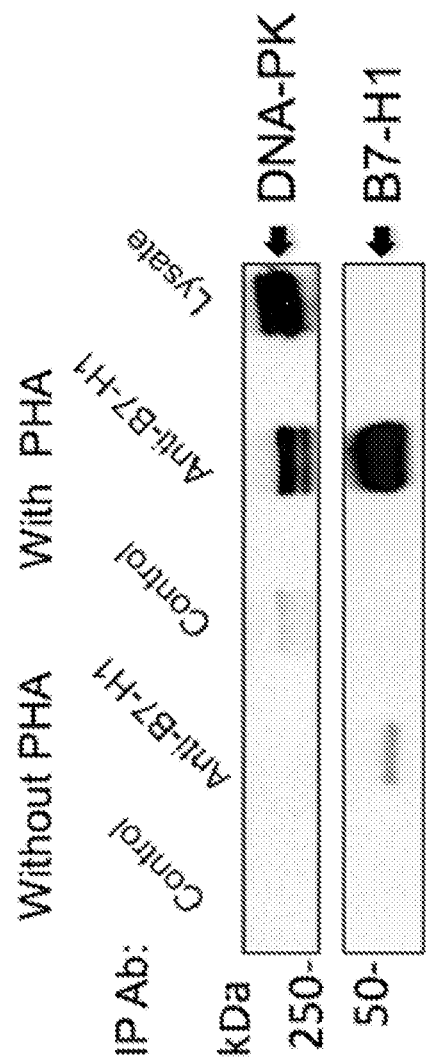
FIG. 10 is a picture of a Western blot showing that B7-H1 is associated with DNA-PK in activated human primary T cells. T cells were activated by PHA for 48 hours.

In pilot studies, a single 450 kDa band was identified in the lysate from a human T cell line (Kaspas299, B7-H1 positive) (Frigola et al., *Clin Cancer Res: an official journal of the Am Assoc Cancer Res* 17:1915-1923, 2011) using an anti-B7-H1 antibody (5H1) in immunoprecipitation (FIG. 9A). Mass spectrometry analyses indicated that the most abundant protein in the 450 kDa band is DNA-PKcs (DNA dependent protein kinase, catalytic subunit). Western blotting was then performed to confirm that DNA-PK is associated with B7-H1. As shown in FIG. 9B, anti-B7-H1 pulled down a protein from the lysate of Kaspas299 cells that was identified as DNA-PK by Western blot (top panel of FIG. 9B). The presence of B7-H1 in the precipitation was confirmed by Western blotting with an anti-B7-H1 antibody (middle panel of FIG. 9B). In addition, B7-H1 was identified in association with DNA-PK when using anti-DNA-PK in immunoprecipitation with Kaspas299 cell lysate (lower panel of FIG. 9B). In addition, the association of B7-H1 with DNA-PK was identified in activated human T cells, but not in resting T cells (FIG. 10). Since only activated human T cells express B7-H1 protein 1, the association of B7-H1 and DNA-PK in activated T cells suggested a potential functional relationship between B7-H1 and DNA-PK.

Experiments are conducted to identify the binding sites and intracellular location of B7-H1 association with DNA-PKcs in T cells. The intracellular domain (ICD) of B7-H1 does not contain a tyrosine that could be phosphorylated by a tyrosine kinase, but it does contain serine and threonine residues that could be targets of DNA-PKcs, as DNA-PKcs is a serine/threonine protein kinase. To determine whether serine or threonine residues are required for the association of B7-H1 with DNA-PKcs, mutations are made at these residues in the ICD of B7-H1, and experiments are conducted to test whether these mutants affect the association of B7-H1 and DNA-PKcs. Briefly, B7-H1 mutants in which individual serine or threonine residues are replaced with alanine (FIG. 11) are produced. B7-H1 negative T cells (Jurkat) are transfected with a mutant B7-H1 and then used in immunoprecipitation assays to test the association of mutant B7-H1 with DNA-PKcs, and to identify a binding site for DNA-PKcs based on the individual serine or threonine mutations. Multiple mutants are produced as needed if the individual mutants are not sufficient to abolish the association of B7-H1 and DNA-PKcs.

The identification of DNA-PK as a binding protein of B7-H1 was unexpected, as DNA-PK is a nuclear protein involved in DNA repair (Collis et al., *Oncogene* 24:949-961, 2005), while B7-H1 is an immunoregulatory molecules mainly expressed on the cell surface. Nevertheless, increased expression of DNA-PK has been reported among apoptotic T cells from patients with rheumatoid arthritis (Shao et al., *J Exp Med* 206:1435-1449, 2009; and Shao et al., *EMBO Mol Med* 2:415-427, 2010), suggesting that DNA-PK mediated DNA repair may be involved in T cell survival. It is likely that the T cell-intrinsic pro-survival function of B7-H1 is mediated by binding with DNA-PK in the nucleus, where DNA-PK promotes the DNA repair that is needed for T cell survival. The up-regulation of B7-H1 in T cells during the contraction phase following expansion suggests a possible translocation of B7-H1 from the T cell surface into the nucleus, where B7-H1 binds to DNA-PK to promote DNA repair for DNA damage accumulated after intensive T cell expansion (Doering et al., *Immunity* 37:1130-1144, 2012; and Baitsch et al., *J Clin Invest* 121: 2350-2360, 2011).

Figure 12:
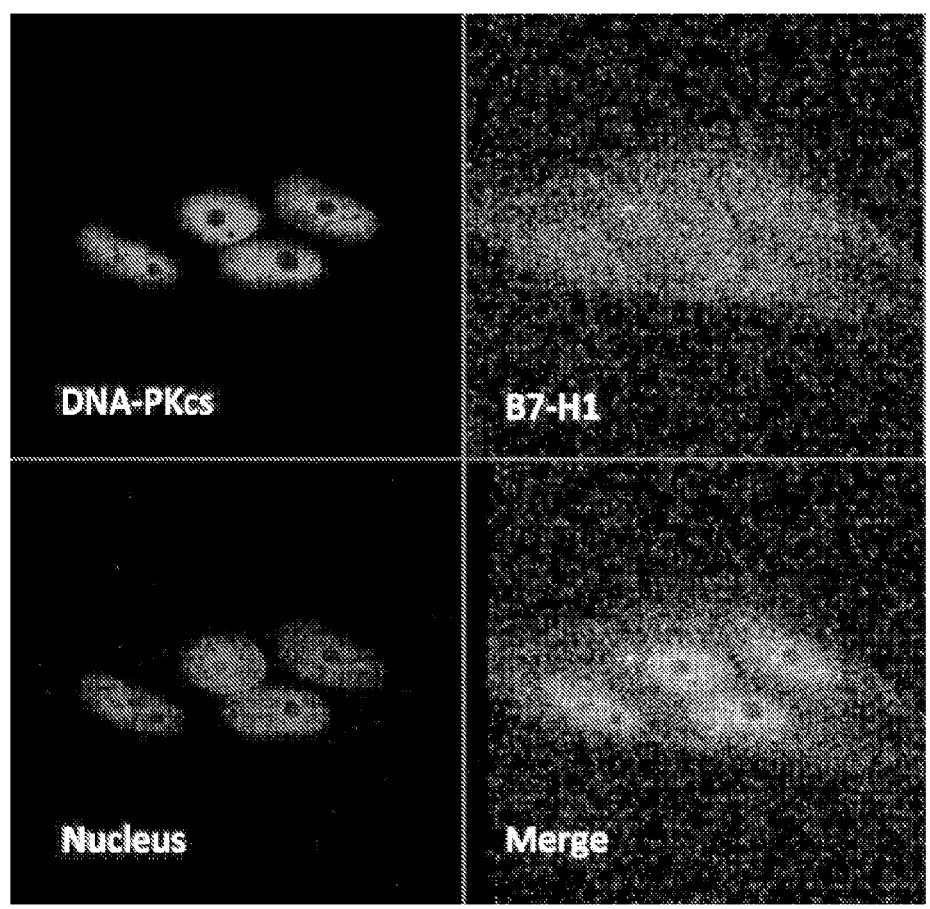
FIG. 12 is an image showing co-localization of B7-H1 and DNA-PKcs in cells from a human breast tumor cell line (MDA-MB-231) treated with topo I inhibitor for 2 hours to induce translocation of B7-H1. Cells were stained for DNA-PKcs (Red), B7-H1 (Green) and nuclei (Blue).

It has been reported that B7-H1 undergoes redistribution from the cell surface into the nucleus in tumor cells upon treatment with chemotherapy drugs (Ghebeh et al., *Breast Cancer Res* 12:R48, 2010). Using this model, experiments were conducted to determine whether translocation of B7-H1 results in close association with DNA-PKcs in the nucleus. The data of FIG. 12 show that DNA-PKcs mainly localized in the nucleus, while B7-H1 had both cytoplasmic and nuclear distribution. In the nucleus, B7-H1 was identified in association with DNA-PKcs. It is possible that activated T cells recapitulate the pro-survival function of B7-H1 when B7-H1 translocates to nuclei, a potential target of B7-H1 in nuclei could be DNA-PK, as implied by the association of B7-H1 and DNA-PK in activated T cells (FIG. 10). To test this possibility, the translocation of B7-H1 in naïve and activated T cells (1-3 days) is examined after TCR stimulation in vitro. The co-localization and intracellular distribution of B7-H1 with DNAPK in resting and activated T cells is analyzed using confocal microscopy. T cell activation may cause B7-H1 distribution into nuclei, where B7-H1 would be closely associated with DNA-PKcs. The strength of TCR stimulation (dose of anti-CD3) and costimulation (CD28) could affect the association and co-localization of B7-H1 and DNA-PKcs. To address this, the dose and anti-CD3 are titrated in the presence or absence of CD28 in these experiments.

Further experiments are conducted to determine the role of DNA-PKcs in activation of p38 MAPK. DNA-PKcs is a serine/threonine protein kinase (450 KDa) and is a member of the phosphatidylinositol kinase (PIK)-related family. Although DNAPK is believed to play a major role in repairing double strand DNA breaks and V(D)J recombination, DNAPKcs also has signaling functions. It has been reported that DNA-PKcs is required for ERK activation in mouse macrophages (Panta et al., *Mol Cell Biol* 24:1823-1835, 2004; and Yotsumoto et al., *J Immunol* 180:809-816, 2008), how DNA-PKcs affects the activation of p38 is not clear. Since p38 activation was increased in B7-H1 KO T cells, the degree to which DNA-PKcs contributes to these changes is tested.

NU7026 (2-(morpholin-4-yl)-benzo[h]chomen-4-one) is a DNA-PKcs inhibitor. This compound is selective for DNA-PKcs, and 10 μM NU7026 can completely inhibit activity of purified DNA-PK (Veuger et al., supra). NU7026 is added into cultures with pre-activated WT and B7-H1 KO T cells and after 24-72 hours of incubation, the activation of p38 is measured in the cells. As a consequence of p38 MAPK activation regulated by NU7026, the level of Bcl-xL also is measured in the T cells after treatment with NU7026. If p38 activation is regulated by DNA-PKcs, changes in p38 activation in the presence of NU7026 would be observed in WT T cells. If B7-H1 requires DNA-PKcs to regulate activation of p38 MAPK, NU7026 would induce significant changes in p38 MAPK activation in WT T cells, but not in B7-H1 KO T cells. NU7026 increased p38 MAPK activation in WT, but not in B7-H1 KO T cells, suggesting that DNA-PK in association with B7-H1 negatively regulates p38 MAPK activation. Bcl-xL levels would change accordingly with the changes in p38 MAPK activation. In addition to inhibition of DNA-PKcs activity by NU7026, the impact of total DNA-PKcs protein levels on p38 MAPK activation is evaluated. siRNA-mediated knockdown of DNA-PKcs is known to result in reduced ERK activation in mouse macrophages (Yotsumoto et al., supra). Using a similar approach, experiments are conducted to test whether down-regulation of DNA-PKcs in T cells affects p38 MAPK activation in WT and B7-H1 KO T cells. Preliminary data predicts a potential link between DNA-PK and activation of p38 MAPK. DNA double strand breaks induced G2/M cell cycle checkpoint, dependent on activation of p38 MAPK (Pedraza-Alva et al., *EMBO J* 25:763-773, 2006). On the other hand, the involvement of DNA-PK in activation of the MAPK signal cascade has been proposed (Panta et al., supra). Thus, association with DNA-PK would recruit B7-H1 in the regulation of p38 MAPK. Studies to investigate how DNA-PK is involved in the B7-H1 signaling pathway (e.g., in regulation of p38 MAPK activation) in T cells are conducted. A potential link is Akt activation, as studies have identified DNA-PK as a kinase that activates Akt (Feng et al., *J Biol Chem* 279:41189-41196, 2004; and Dragoi et al. *EMBO J* 24:779-789, 2005). DNA-PKcs colocalizes with Akt at the plasma membrane and phosphorylates Akt on Ser473, resulting in about a 10-fold enhancement of activity. A decrease in activation of Akt was observed in B7-H1 KO T cells. Taken together, results from these studies collectively provide new insight into regulation of T cell survival by a previously unknown B7-H1/p38 MAPK/Bcl-xL pathway.

Example 8—Defining the Role of T Cell Intrinsic B7-H1 in T Cell Differentiation

Figure 13:
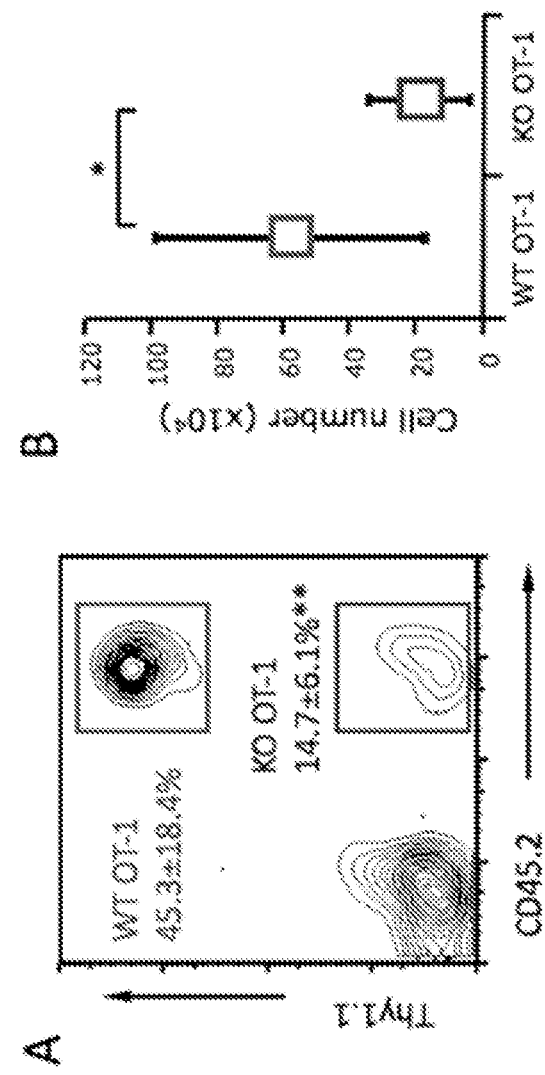
FIG. 13A shows the percentages of WT (Thy1.1$^+$ CD45.2$^+$) and B7-H1 KO (Thy1.1$^-$CD45.2$^+$) CD8 T cells detected in the spleen on day 15 post transfer.
FIG. 13B is a graph plotting the numbers of transferred T cells (n=3). *p<0.05, **p<0.01.

To establish protective T cell immunity, primed T cells need to acquire long term survival characteristics and to mount rapid and effective secondary responses to pathogen, traits shared with memory T cells (Pulko 2011, supra; Collis, supra; and Ghebeh et al., supra). Protecting T cells from contraction is a new function of T cell intrinsic B7-H1, suggesting that up-regulation of B7-H1 by effector T cells would give them selective advantage in differentiating into memory T cells. To test this possibility, pre-activated WT and B7-H1 KO CD8 T cells were co-transferred at the same numbers into naïve CD45.1+B6.SJL mice to monitor their survival in an antigen-free host (a model for memory cell differentiation) (Pulko 2011, supra). On day 15 after transfer, the transferred WT and B7-H1 KO effector T cells were easily identified by their congenic markers (FIG. 13A). As expected, fewer transferred B7-H1 KO T cells than WT T cells were found in the spleen. The dramatic reduction of B7-H1 KO T cells implied that most effector T cells require B7-H1 to survive and become memory T cells.

Figure 14:
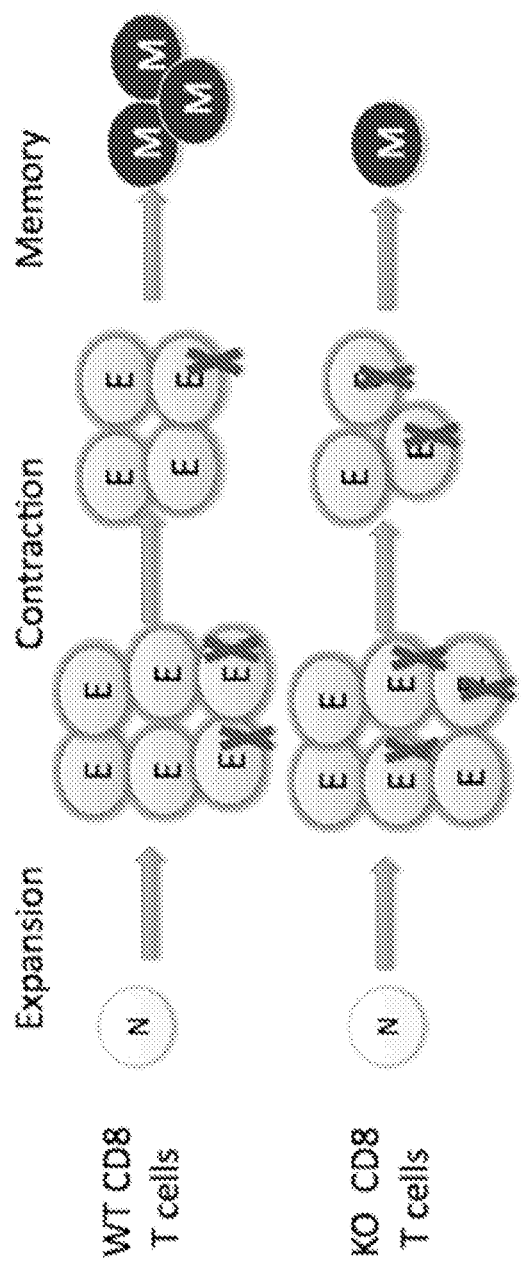
FIG. 14 is a diagram showing the proposed role of B7-H1 expressed by T cells in memory T cell generation. In the absence of B7-H1, some effector T cells may undergo more apoptosis during the contraction phase, and fewer of them become memory cells.

In the linear differentiation model, memory T cells are believed to be generated from effector T cells that survive the contraction phase (Opferman et al., *Science* 283:1745-1748, 1999; and Wherry et al., *Nat Immunol* 4:225-234, 2003). Since fewer B7-H1 KO T cells survived at the end of the contraction phase (FIG. 4) and after 15 days following transfer in vivo (FIG. 13), it was hypothesized that T cell-intrinsic B7-H1 helps effector T cells to survive the contraction phase and become memory cells. This hypothesis is diagrammed in FIG. 14. Both B7-H1 deficient and transgenic T cell models are used to test this hypothesis and define a new mechanism underlying memory T cell differentiation by dissecting the role of T cell intrinsic B7-H1.

Theiler's murine encephalomyelitis virus (TMEV) is an endogenous pathogen in mice. Intracranial infection of TMEV causes acute encephalitis. Resistant strains of mice (such as C57BL/6 mice H-$2^b$) effectively clear the TMEV infection and generate a T cell response against the viral protein (Borson et al., *J Virol* 71:5244-5250, 1997). To easily track viral antigen specific T cell responses, the TMEV strain that includes the H-$2K^b$ restricted OVA epitope SIINFEKL (SEQ ID NO:2; Pavelko et al., *Mol Therapy* 21:1087-1095, 2013) is used. To evaluate the role of T cell intrinsic B7-H1 in T cell differentiation and mounting an anti-viral immunity, the TMEV-OVA infection model is used.

The same numbers ($2 \times 10^3$) of naïve CD8 T cells isolated from WT (Thy1.1) or B7-H1 KO (CD45.2) C57BL/6 mice are co-transferred separately into CD45.1 B6.SJL mice. On the same day of T cell transfer, mice are inoculated intracranially with $2 \times 10^6$ PFU of the Daniel strain of TMEV (Mendez-Fernandez et al., *Eur J Immunol* 33:2501-2510, 2003). The function and phenotype of the transferred T cells are analyzed on days 7 (effector phase) and 30 (memory phase) after infection in the brain and draining lymph nodes. H-2K$^b$/OVA tetramer staining and congenic markers are used to define the transferred WT and B7-H1 KO T cell responses to TMEV infection. The effector or memory phenotype of the transferred T cells is determined by the expression of CD43 (1B11) for effector T cells (Harrington et al., *J Exp Med* 191:1241-1246, 2000), and CD44 and CD62L for memory T cells. The function of effector/memory T cells is analyzed by ex vivo assays to evaluated degranulation (CD107a expression) and intracellular production of cytokines (IFN-γ, IL-2, and TNF-α) (Webster et al., supra). On day 7 and day 30, a CTL assay is performed to analyze the function of effector (day 7) or memory (day 30) T cells in vivo as previously reported (Pulko 2009, supra). The anti-viral immunity is evaluated by detecting the persistence of TMEV in the brain using TCR and viral plaque assay (Zhang et al., *J Neuroimmunol* 116:178-187, 2001).

A sample size of 10 mice per group provides at least 90% power to detect the significant difference at alpha=0.05 based on previous studies (Pavelko et al., supra). By comparing the frequency/number and function of the persistence of transferred B7-H1 WT and KO T cells, the extent to which B7-H1 deficiency affects the generation of functional memory CD8 T cells is determined. Analysis and comparison of their memory phenotype (T effector CD43/1B11$^{high}$, T effector memory CD44$^{high}$CD62L$^{low}$ or T central memory CD44$^{high}$CD62L$^{high}$) allows determination of what subset(s) of CD8 T cells require B7-H1 for their differentiation.

Figure 15:
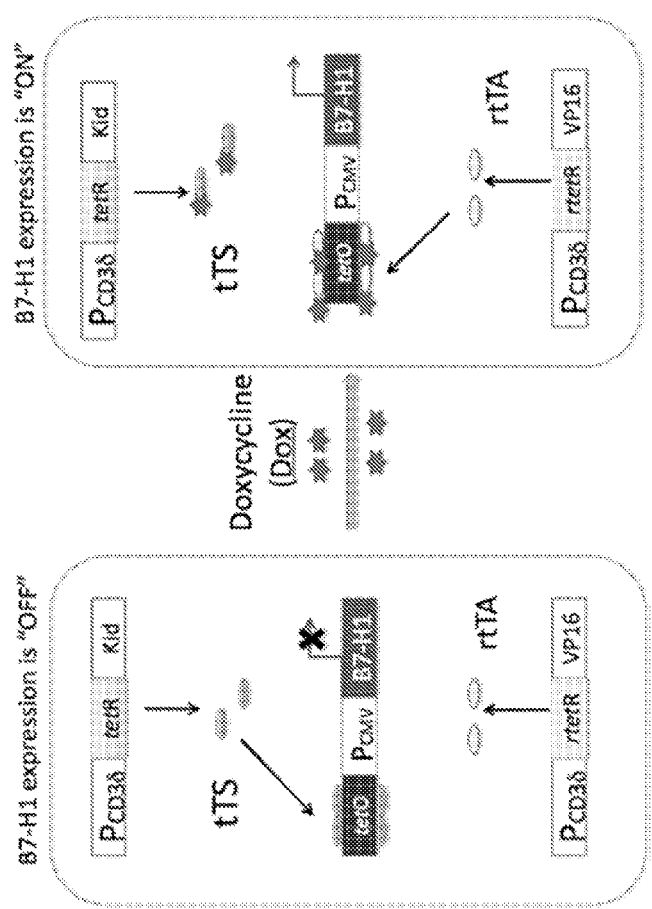
FIG. 15 is a diagram depicting the inducible B7-H1 expression in T cells. Injection of Dox induces B7-H1 expression in T cells by activating transcription of B7-H1 via rtTA driven by a CD3δ promoter, and releasing the repressor (tTS) from tetO.

In addition to using B7-H1 KO mice as models, an inducible B7-H1 transgenic mouse model in which B7-H1 expression can be specifically and temporally induced on T cells (FIG. 15) is used. In this model, a CD3δ (T cell-specific) promoter is used to drive the expression of a tetracycline-controlled transcriptional silencer (tTS) and a reverse tetracycline-controlled transcriptional activator (rtTA) in T cells. In the absence of doxycycline (Dox), a derivative of tetracycline, tTS actively suppresses transcription of B7-H1 gene (driven by tetO), preventing leaky expression of B7-H1. In the presence of Dox, tTS dissociates from tetO, whereas rtTA binds tetO with high affinity and induces expression of B7-H1. This approach has been used to induce CD4 T cell-specific gene expression in transgenic mice (Huai et al., *Genesis* 45:427-431, 2007), demonstrating this system's efficiency and specificity.

Using this model, T cell expression of B7-H1 is induced on days 0-6 (early stage) or days 8-14 (late stage) respectively by injection of doxycycline, during TMEV-OVA infection. Wild type mice are used as controls for base line T cell responses. The accumulation and function of effector cells and memory T cells in the brain and draining lymph nodes are measured on days 7, 15, and 30 following infection. To assess their protective immunity, immunized mice are challenged with B16-OVA tumor cells on day 21 after immunization, and tumor size is compared between mice with different kinetics/timing of B7-H1 expression by T cells (early vs. late). These experiments permit determination of the optimal timing for turning on B7-H1 expression by T cells during T cell responses to infection in order to enhance protective immunity. Phenotype and functional assays determine how enhanced B7-H1 expression helps memory T cell differentiation.

As both WT and B7-H1 KO CD8 T cells are from C57BL/6 mice that can effectively respond to OVA epitope in H-2K$^b$ hosts, both types of cells may have comparable primary responses to TMEV-OVA infection on day 7. If B7-H1 is required by effector CD8 T cells to survive during the contraction phase, B7-H1 KO CD8 T cells may have more contraction than WT T cells, and consequently, fewer effector/memory B7-H1 KO T cells are accumulated in the infected brain or lymph nodes on day 30. As a result, high amounts of TMEV remain in the brain tissues of mice transferred with B7-H1 KO T cells compared to mice receiving WT T cells. These results determine whether T cell intrinsic B7-H1 is required to generate a protective T cell immunity.

The induced T cell B7-H1 expression model is used to determine when T cell B7-H1 is required for survival of activated T cells and subsequent differentiation. The induced B7-H1 model is similar to T cell-specific expression constructs that have been previously established. It is acknowledged that induced B7-H1 might not undergo a degradation process as occurs with natural B7-H1 in T cells, and would overlap or compete with endogenous B7-H1 in T cells. To exclude the overlapping or competitive effects, this model is generated in a B7-H1 KO background. Such a model may be a valuable tool applicable to other immune systems, including evaluating the impact of T cell B7-H1 on the efficacy of tumor vaccines in combination with and B7-H1 blockade as an approach for treating solid tumors.

Although T cell survival is critical for mounting a protective immunity, T cell trafficking to tumor or infection site also is important. To know whether B7-H1 regulates T cell migration, congenic markers are used to track transferred effector T cells in tumor-bearing or infected mice to examine the migration of WT and B7-H1 KO T cells in vivo. The cytolytic activity of CD8 T cells also may impact the protective immunity mediated by CTLs. If B7-H1 KO T cells do not mount a protective immunity in vivo, experiments are done to test whether it is because of any defects in killing of target cells by B7-H1 KO CD8 T cells. To evaluate this possibility, cytolytic activity is determined using calcein-labeled tumor or infected target cells in vitro.

Example 9—Defining the Agonistic Function of Anti-B7-H1 Antibody on T Cell Function To block the B7-H1/PD-1 signaling pathway, antibodies against B7-H1 have been aggressively pursued as an immunotherapeutic option for treating human solid cancers (Brahmer et al., supra). However, the potential agonist functions of such blocking antibodies have not been addressed in the context of T cell biology. Given the pro-survival function of B7-H1 expressed by T cells (Pulko 2011, supra), it is possible that B7-H1 antibody administered in the course of blockade therapy may have agonistic effects on T cell-associated B7-H1, and may disrupt the intrinsic pro-survival function of B7-H1 for T cells. Ligation of B7-H1 by antibody resulted in enhanced apoptosis of fully activated human T cells, with a dramatic increase in transcription of TNF-related apoptosis-inducing ligand (TRAIL) (Dong et al., supra). Interestingly, an autoantibody to B7-H1 was identified in the sera of patients with active rheumatoid arthritis that have ongoing T cell apoptosis (Dong et al., supra; Shao et al. 2009, supra; and Shao et al. 2010, supra). It has been observed that injection of B7-H1 antibody reduced the numbers of effector CD8 T cells but not CD4 T cells at late stages of T cell activation (FIG. 1) (Rowe et al., supra; Xu et al., supra; and Seo et al., *Immunology* 123:90-99, 2008). Although the reduced outcome of CD8 T cell responses could be explained by a potential co-stimulatory role of B7-H1 (e.g., in promoting T cell expansion) that could be blocked by anti-B7-H1 antibodies, another possibility is that some anti-B7-H1 antibodies might have agonistic function (e.g., disrupting B7-H1's intrinsic pro-survival function, and triggering T cell death). This raises several questions, including how to identify and screen agonistic B7-H1 antibodies for T cells, what is the signaling pathway triggered by agonistic B7-H1 antibodies in T cells, and what is the impact of agonistic B7-H1 antibodies on tumor immunity. This knowledge may be critical for selecting therapeutic anti-B7-H1 antibodies. Identification of agonistic B7-H1 antibodies will help to reduce unwanted negative effects on T cell survival. Further, the selection of B7-H1 antibody with blocking effects but not agonistic effects can maximize the therapeutic effects of anti-B7-H1 antibody in treatment of human cancers.

To being answering these questions, studies are conducted to select agonistic antibodies to B7-H1 based on their intracellular signaling profile. As noted above, B7-H1 ligation increased transcription of TRAIL in activated human T cells (Dong et al., supra). The TRAIL gene is tightly regulated, potentially due to its considerable apoptosis inducing potential. Activation of p38 MAPK selectively induces apoptosis of CD8 T cells, but not CD4 T cells (Merritt et al., supra; and Rincon and Pedraza-Alva, *Immunol Rev* 192:131-142, 2003). In addition, activation of p38 MAPK has been correlated with induction of TRAIL expression (Zula et al. *Proc Natl Acad Sci USA* 108:19689-19694, 2011). Since B7-H1 ligation by antibody induced the up-regulation of TRAIL, B7-H1 ligation may lead to activation of p38 MAPK, which in turn induces TRAIL expression. To test this possibility, the activation (phosphorylation) of p38 MAPK was measured in activated T cells following ligation of B7-H1 by a panel of anti-B7-H1 monoclonal antibodies (5H1, H1A, MDX, and 2.2B). The results shown in FIG. 16 demonstrate that H1A and 2.2B significantly increased the phosphorylation of p38 MAPK in activated human T cells. It is noted that antibodies H1A and 2.2B share the same IgG type (mouse IgG1) but have different binding sites from 5H1, suggesting that the epitope on B7-H1 rather than the isotype of antibody determines the activation of p38 MAPK. As described below, measuring the activation of p38 MAPK in T cells is used to screen for B7-H1 antibodies with agonistic function. Based on preliminary data, it is hypothesized that agonistic antibodies against B7-H1 affect CD8 T cell survival via activation of the p38 MAPK pathway.

Figure 17:
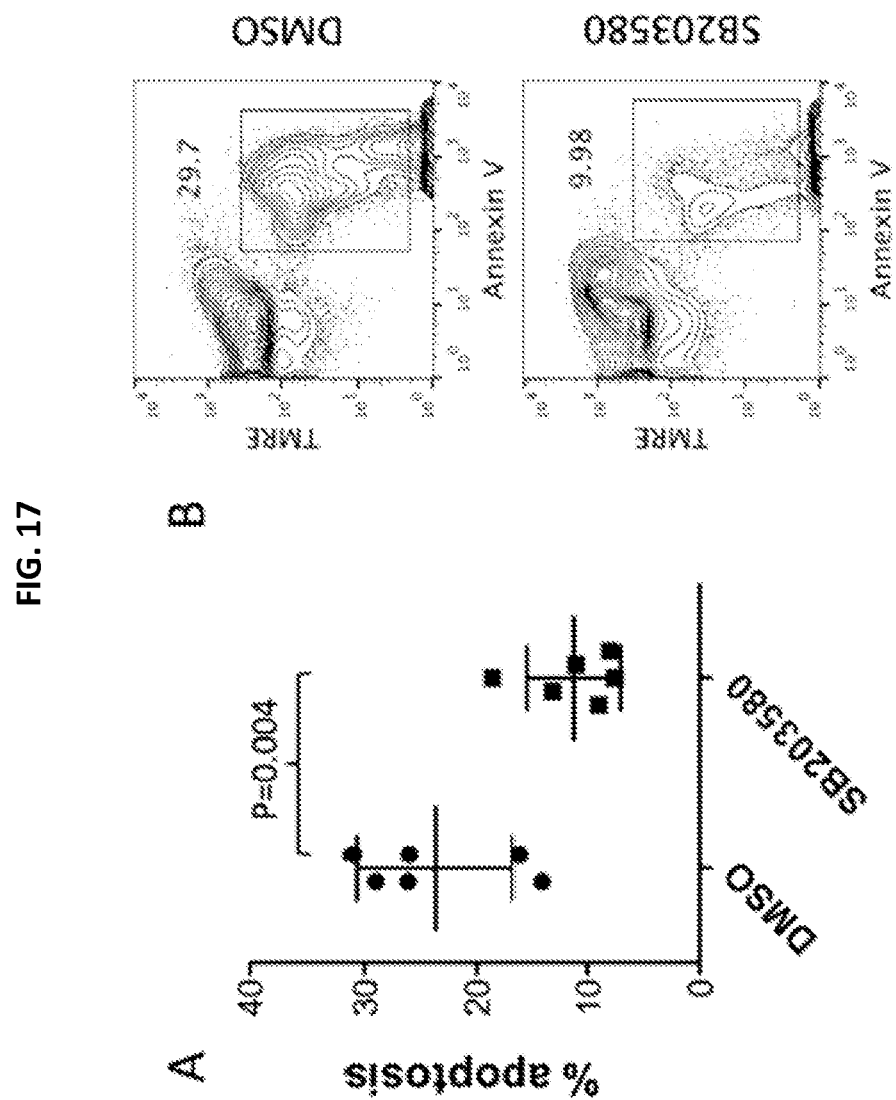
FIGS. 17A and 17B show that T cell apoptosis was reduced when pre-activated CD8 T cells were incubated with SB203580 to inhibit p38 MAPK.

To test this hypothesis, studies are conducted to determine whether an anti-B7-H1 antibody with the potential for activating p38 also can enhance T cell apoptosis. CD8 T cells maintain a 2-3 fold higher level of p38 MAPK activity than CD4 T cells, and activation of p38 MAPK in vivo caused a specific loss of CD8 T cells in peripheral lymphoid organs (Merritt et al., supra). The loss of CD8 T cells was attributed to increased apoptosis of CD8 T cells mediated by caspases following p38 MAPK activation. Experiments to test whether inhibition of p38 MAPK reduces apoptosis of human CD8 T cells showed that addition of a specific p38 MAPK inhibitor (SB203580) dramatically reduced apoptosis of activated CD8 T cells in vitro (FIG. 17). Thus, the activation of p38 MAPK appears to induce CD8 T cell apoptosis.

Using the same model as in FIG. 17, the degree of apoptosis of T cells induced by antibodies is compared, based on their ability to activate p38 MARK. Purified naïve (CD45RA+CCR7+) CD8 T cells from human PBMC are incubated with anti-CD3/CD28 beads in the presence of plate-bound anti-B7-H1 mAb that activates p38 (H1A or 2.2 B) or does not activate p38 (5H1 or MDX); a control group uses isotype control mIgG1. After 48 hours of incubation, the apoptosis of T cells is measured by staining with TMRE (for mitochondria potential) and Annexin V. The number of live T cells is counted to confirm a net loss of cells due to apoptosis. If activation of p38 MAPK enhances CD8 T cell apoptosis, more apoptosis or loss of viable CD8 T cells in culture with H1A or 2.2B anti-B7-H1 mAb compared with 5H1 mAb or control group would be expected. To test whether activation of p38 MAPK is required in T cell apoptosis induced by agonistic B7-H1 antibody, p38 specific inhibitor SB203580 is used in culture with agonist antibody. If activation of p38 MAPK is required for T cell apoptosis, enhanced CD8 T cell apoptosis caused by an agonistic antibody against B7-H1 would be blocked by inhibition of p38 MAPK.

Studies also are conducted to assess how ligation of B7-H1 by antibody leads to activation of p38 MAPK. A recent report implies that downstream genes involved in the MAPK/ERK pathway are the targets of B7-H1 mediated modulation in tumor cells (Cao et al., *Cancer Res* 71:1235-1243, 2011) Skin tumors induced in B7-H1 Tg mice show up-regulated Snail and Slug and down regulated Ecadherin, all of which are dependent on the activation of MAPK/ERK signaling (Pece and Gutkind, *J Biol Chem* 275:41227-41233, 2000; Bonni et al., *Science* 286:1358-1362, 1999; and Conacci-Sorrell et al., *J Cell Biol* 163:847-857, 2003). To test whether ligation of B7-H1 might affect the MAPK/ERK activity, the relative phosphorylation levels of 26 proteins (FIG. 18) involved in the MAPK/ERK pathway in T cells are measured and compared after incubation with B7-H1 antibody with or without ability to activate p38 MAPK. Preactivated T cells are incubated with either plate-bound or soluble anti-B7-H1 antibody for different period of times (5, 10, 30, 60, or 120 minutes) followed with a quick cell lysate preparation. Cell lysates are used in Array Assay of Phosphorylation of p38 MAPK pathway, according to manufacturer's directions (R&D Systems, Minneapolis, Minn.). The levels of phosphorylation of individual proteins in this pathway are compared between T cells with and without antibody B7-H1 ligation. Agonistic B7-H1 antibody may alter the activation of some upstream proteins in the MAPK/ERK pathway that could accordingly lead to regulation of p38 MAPK. The regulatory function of these candidate proteins is confirmed by their specific inhibitors or knockdown their protein levels.

The signaling pathway of B7-H1 following antibody ligation is identified. A panel of anti-human B7-H1 mAbs is used to screen and compare agonistic functions. This information is critical for selecting B7-H1 antibodies having desired blocking properties to be used to treat human solid cancers (Brahmer et al., supra), while agonistic properties are filtered from the B7-H1 antibody inventory to avoid causing undesired effects on T cell survival. Assays and potential molecular signaling pathways developed and identified in these studies may be translated into a screening platform for selecting candidate therapeutic anti-B7-H1 monoclonal antibodies for clinical use. Although these studies focus on the potential impact of anti-B7-H1 antibody on T cell survival and apoptosis, as predicted by previous studies (Dong et al., supra), ligation of B7-H1 also may impact functions of activated T cells (such as cytokine production).

Figure 19:
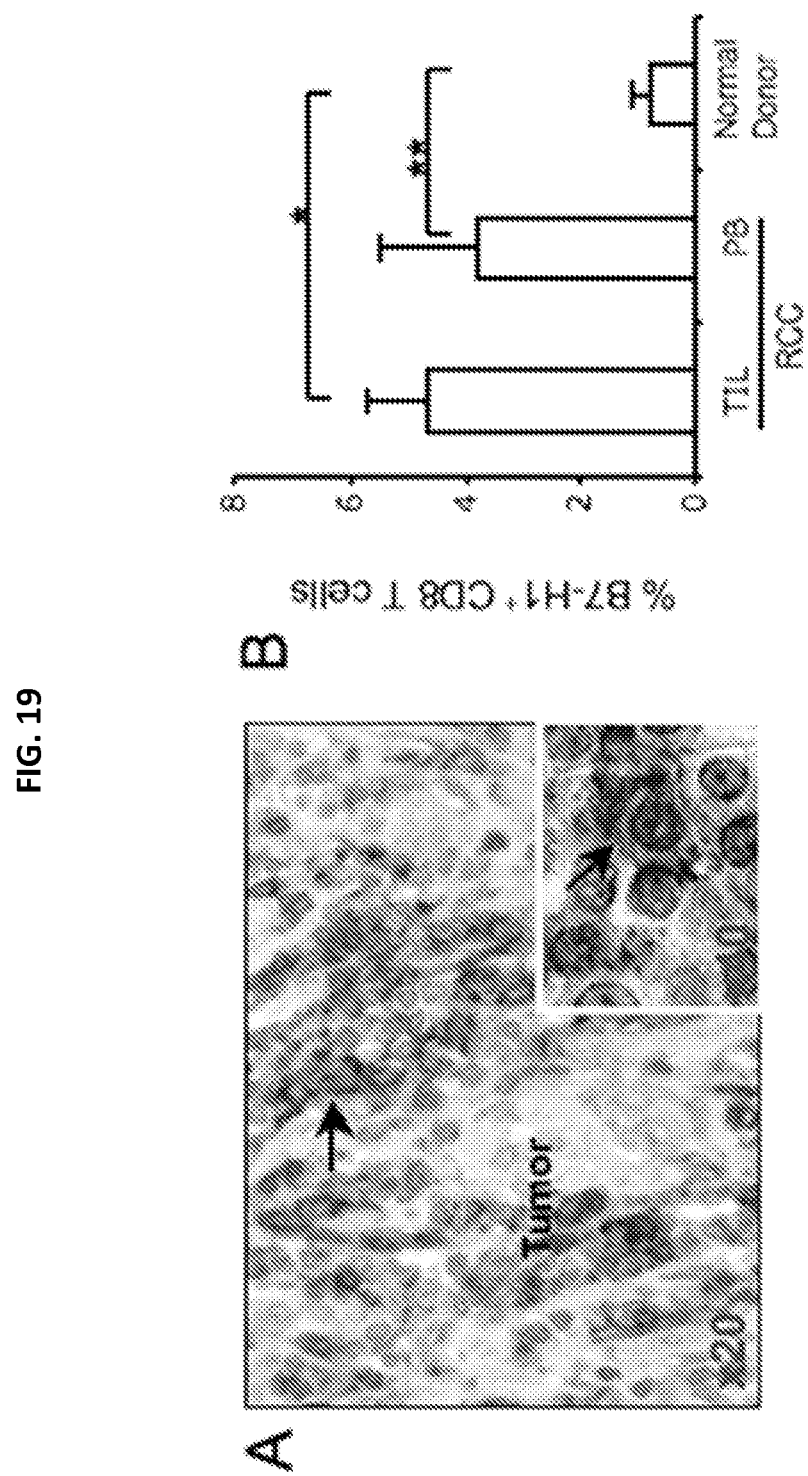
FIGS. 19A and 19B show that B7-H1$^+$ CD8 T cells are increased in RCC patients.

Further experiments are carried out to define the impact of agonistic B7-H1 antibody on tumor immunity. B7-H1 expressed by tumor cells may not be the only target of administered therapeutic anti-B7-H1 antibody. B7-H1 positive CD8 T cells are frequently observed in human renal cell carcinoma tissues and peripheral blood (FIG. 19). However, the impact of anti-B7-H1 on the function of tumor-reactive T cells has not been evaluated. Ligation of B7-H1 expression by T cells could affect the outcome of B7-H1 blockade therapy using anti-B7-H1, as anti-B7-H1 antibody may have agonistic effects on T cells in regarding to their survival. Thus, this information is critical.

Figure 20:
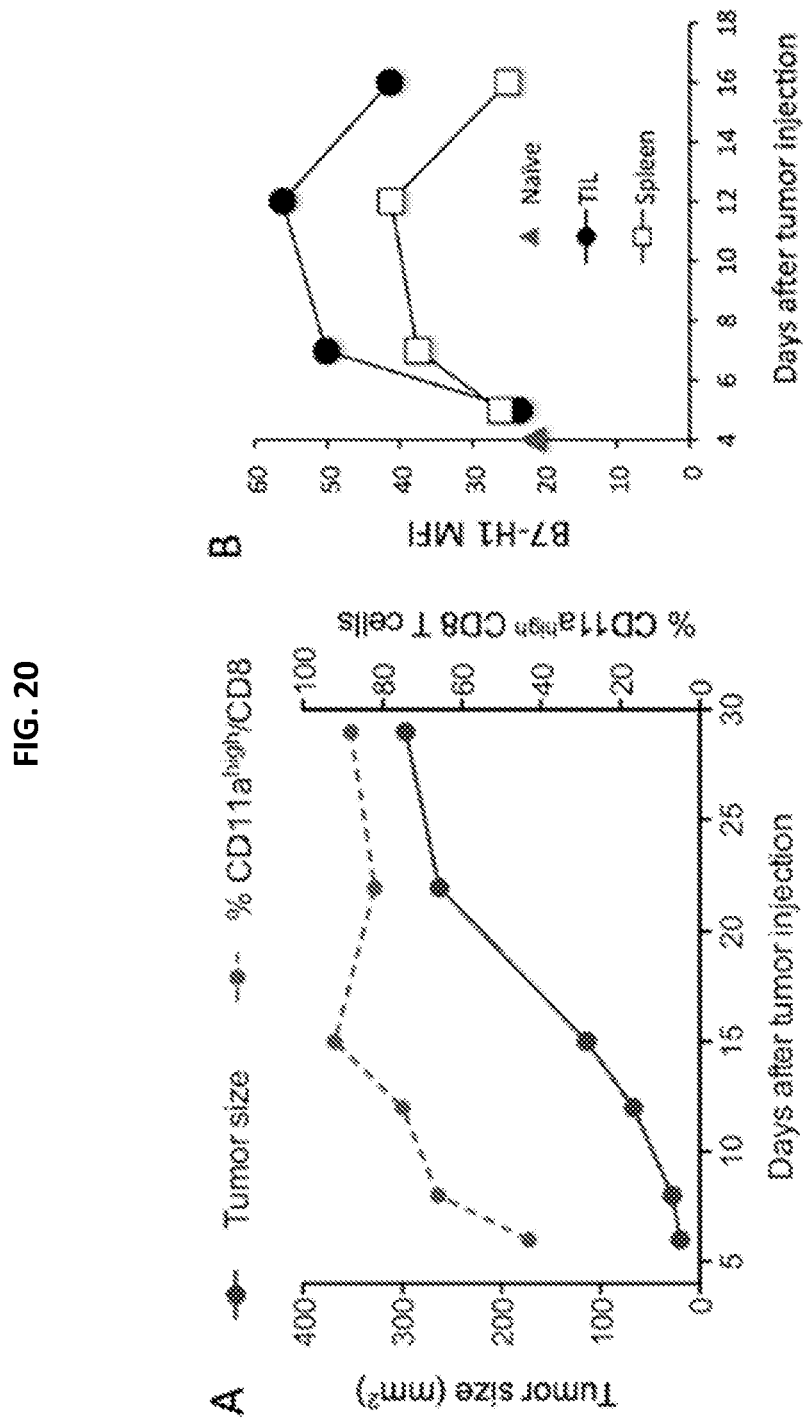
FIGS. 20A and 20B are a pair of graphs showing the kinetics of tumor-reactive CD8 T cells and their expression of B7-H1, after B16-OVA tumor cells were subcutaneously injected into C57BL/6 mice.

To identify the timing for targeting B7-H1 expressed by T cells within tumors, the kinetics of tumor-reactive CD8 T cells within growing tumors were determined, and the levels of B7-H1 expression by tumor-reactive CD8 T cells were measured. CD11a$^{high}$ was used as a surrogate marker to identify tumor-reactive CD8 T cells (Gibbons et al., supra). As shown in FIG. 20, CD11a$^{high}$ CD8 T cells gradually increased in growing tumors and peaked at day 15, a turning point for rapid growth of tumors. Accordingly, B7-H1 expression increased in CD11a$^{high}$ CD8 T cells up to day 12, and declined thereafter. These results demonstrated that up regulation of B7-H1 in tumor-reactive CD8 T cells accompanies T cell expansion within tumors, and down regulation of B7-H1 advances T cell contraction within tumors, suggesting B7-H1 may be required for T cell accumulation at tumor sites.

Figure 21:
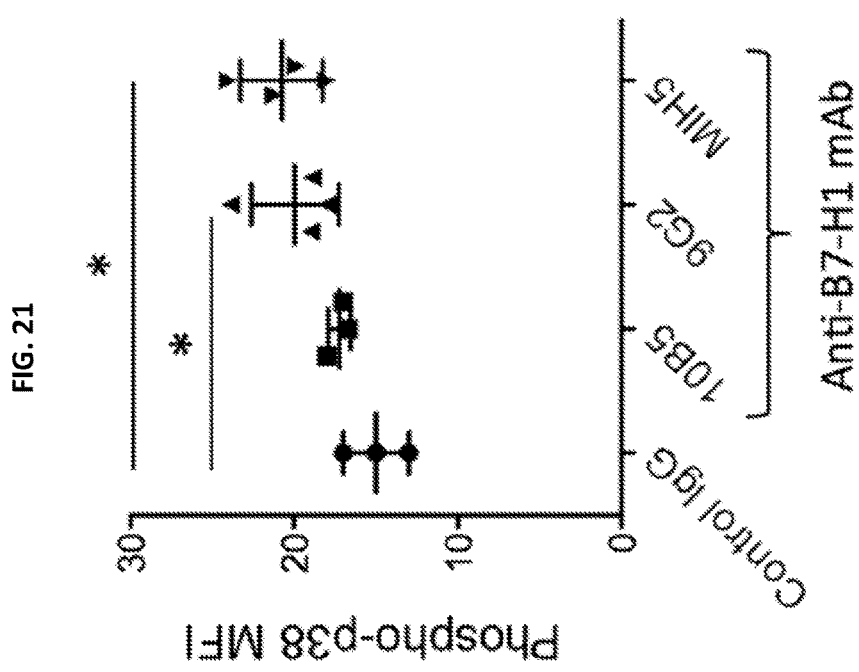
FIG. 21 is a graph plotting the average levels of phosphorp38 MAPK in mouse T cells incubated with plate bound anti-B7-H1 mAb or control Ab in the presence of anti-CD3/CD28 beads, and showing that ligation of B7-H1 increased activation of p38 MAPK. MFI: mean fluorescence intensity. *p<0.05.

To examine the impact of B7-H1 antibody on the accumulation and function of tumor-infiltrating T cells, a panel of anti-B7-H1 mAbs is compared based on their different agonistic functions. The anti-mouse B7-H1 monoclonal antibodies 10B561 ("10B5"), 10F.9G262 ("9G2"), and MIH563 ("MIH5") are all dual blockers of B7-H1/PD-1 and B7-H1/B7-1 binding. As shown in FIG. 21, 9G2 and MIH5, but not 10B5, increased the activation of p38 MAPK as compared to control IgG (rat IgG), suggesting that 9G2 and MIH5 may have agonistic effects on B7-H1 expressed by T cells. Interestingly, 9G2 may reduce CD8 T cell responses in vivo (Rowe et al., supra; and Xu et al., supra). It is likely that 10F.9G2 has agonistic function, such that when it engages B7-H1 expressed by activated CD8 T cells in vivo, it may induce T cell apoptosis by activation of p38 MAPK.

Using the tumor model of FIG. 20, the impacts of anti-B7-H1 mAb with (9G2) or without (10B5) agonistic function are compared. Anti-B7-H1 mAbs are injected during days 6-12, when B7-H1 has higher expression on T cells (FIG. 20). Antibody or isotype control IgG (200 µg) is injected i.p. every three days (on days 6, 9, and 12). The impact of each antibody is determined by its effects on T cell function and tumor growth. On days 14, 20, 27 after tumor inoculation, CD8 T cells are isolated from tumor tissues, and their frequency and function are analyzed. In addition, tumor growth is measured after antibody injection. Each group includes 5 mice, and all experiments are performed independently at least 3 times. Two-sided, unpaired Student's t-tests are used to evaluate differences in T cell frequency and tumor growth between groups of mice. P-values <0.05 is considered statistically significant.

These studies are used to investigate the hypothesis that agonistic B7-H1 antibodies may compromise antitumor immunity mediated by CD8 T cells due to activation of p38 MAPK. Since accumulation of sufficient tumor-reactive CD8 T cells at tumor sites is critical for controlling tumors, a low frequency of functional tumor-reactive CD8 T cells would represent a deficiency in antitumor activity. Mice treated with anti-B7-H1 blocking antibody without agonistic function would have a survival advantage compared with mice treated with agonistic B7-H1 antibody. It is acknowledged that p38 MAPK activation may not be the only readout for determining the agonistic function of anti-B7-H1 mAb in vitro, as some antibodies that do not have agonistic effects in vitro might have agonistic effects in vivo. A careful comparison of the frequency and numbers of tumor-reactive CD8 T cells is used to identify the final impact of B7-H1 antibodies on T cells. On the other hand, the potential effects of agonistic B7-H1 antibodies on tumor cells should be considered in interpreting tumor growth data. The anti-apoptosis function of B7-H1 was identified in tumor cells, but the impact of B7-H1 ligation on tumor growth and survival is not clear. The studies discussed herein are used to reveal new mechanisms for B7-H1 in T cell survival. These studies provide knowledge necessary for selecting optimal B7-H1 antibodies to improve the efficacy of checkpoint blockade therapy for human cancers.

Example 10—Ligation of B7-H1 Reduced Phosphorylation of AKT in CD8 T Cells

Figure 22A:
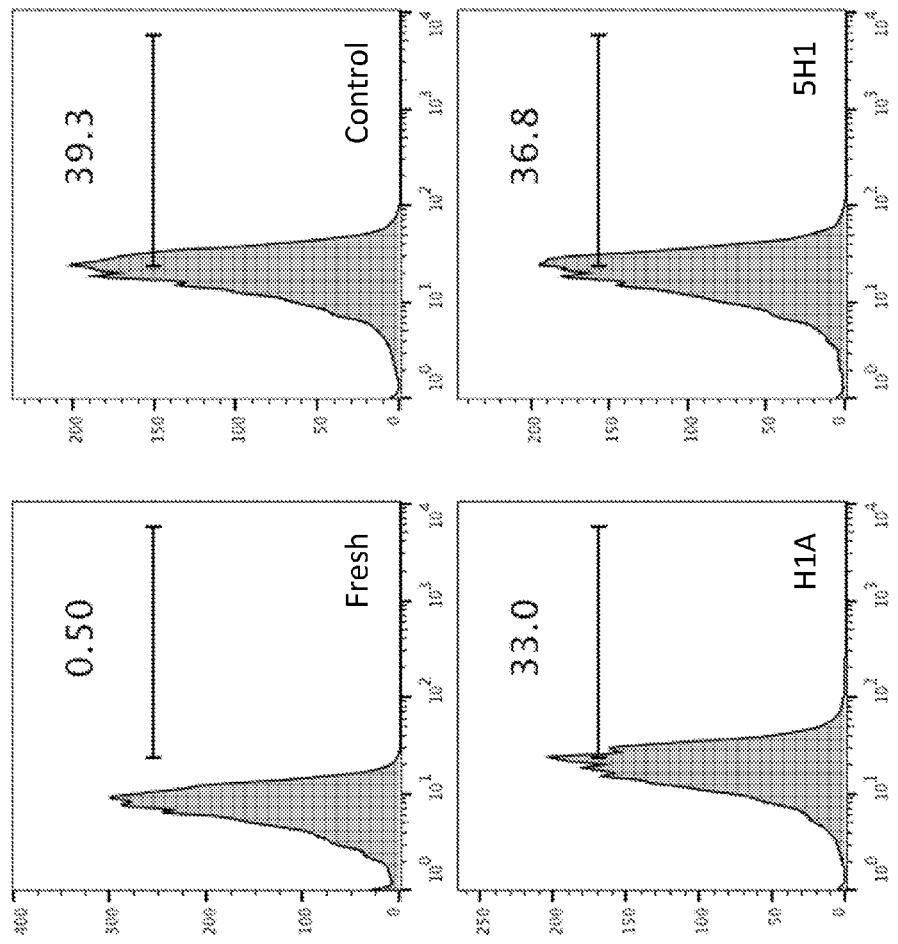
FIG. 22A is a series of histograms showing the levels of phosphorylated AKT in freshly purified human peripheral blood CD8 T cells after incubation with anti-CD3, anti-B7-H1 (H1A and 5H1), or an isotype control antibody to B7-H1. AKT phosphorylation was assessed by intracellular staining with an anti-phosphor-AKT (S473) antibody.
Figure 22B:
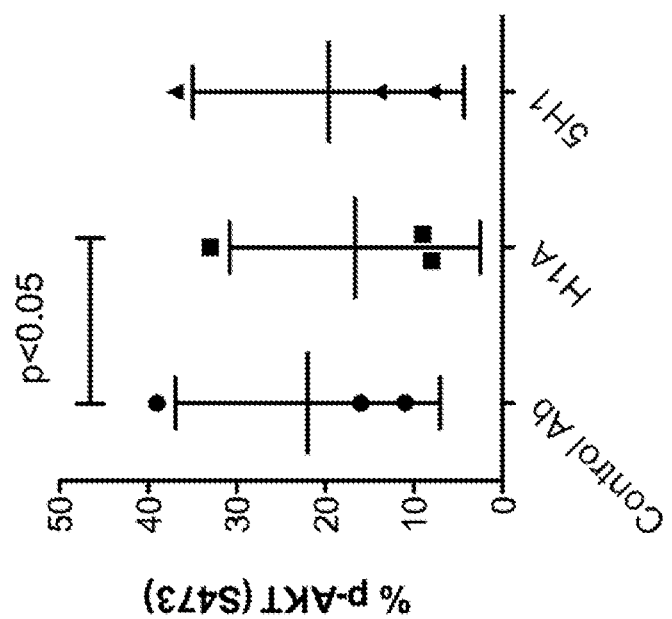
FIG. 22B is a graph plotting the level of phosphorylated AKT in the cells, showing pooled data from three donors.

Freshly purified human peripheral blood CD8 T cells were incubated with anti-CD3 and H1A or 5H1 antibodies to B7-H1 for 24 hours. The control was an isotype of anti-B7-H1 antibody. AKT phosphorylation was analyzed by intracellular staining with anti-phosphor-AKT (S473) antibody. FIG. 22A contains representative histograms of phosphor-AKT expression, while FIG. 22B is a graph plotting the pooled data from three donors. Ligation of B7-H1 by the H1A antibody significantly reduced AKT phosphorylation ($p<0.05$).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying an anti B7-H1 antibody as having agonistic activity, the method comprising contacting a population of activated T cells with the antibody, performing a quantitative assay to measure the level of p38 mitogen-activated protein kinase (MAPK) activation in the T cells, and identifying the antibody as having agonistic activity when the level of p38 MAPK activation is increased in the activated T cells as compared to a control level of p38 MAPK activation.

2. The method of claim 1, wherein the level of p38 MAPK activation is measured using flow cytometry.

3. The method of claim 1, wherein the level of p38 MAPK activation is measured as an increase in phosphorylation.

4. The method of claim 1, comprising contacting the T cell population with the anti B7-H1 antibody for 12-36 hours.

5. The method of claim 1, comprising contacting the T cell population with the anti B7-H1 antibody for 24 hours.

6. The method of claim 1, wherein the control level of p38 MAPK activation is the level of p38 MAPK activation in a population of activated T cells contacted with control IgG.

* * * * *

SEQUENCE LISTING

```
<160> NUMBER OF SEQ ID NOS: 2

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
```

```
                    20                  25                  30
Gly Ser Asn Met Thr Ile Glu Cys Lys Phe Pro Val Glu Lys Gln Leu
                35                  40                  45
Asp Leu Ala Ala Leu Ile Val Tyr Trp Glu Met Glu Asp Lys Asn Ile
     50                  55                  60
Ile Gln Phe Val His Gly Glu Glu Asp Leu Lys Val Gln His Ser Ser
 65                  70                  75                  80
Tyr Arg Gln Arg Ala Arg Leu Leu Lys Asp Gln Leu Ser Leu Gly Asn
                 85                  90                  95
Ala Ala Leu Gln Ile Thr Asp Val Lys Leu Gln Asp Ala Gly Val Tyr
                100                 105                 110
Arg Cys Met Ile Ser Tyr Gly Gly Ala Asp Tyr Lys Arg Ile Thr Val
                115                 120                 125
Lys Val Asn Ala Pro Tyr Asn Lys Ile Asn Gln Arg Ile Leu Val Val
                130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
                180                 185                 190
Val Thr Ser Thr Leu Arg Ile Asn Thr Thr Thr Asn Glu Ile Phe Tyr
                195                 200                 205
Cys Thr Phe Arg Arg Leu Asp Pro Glu Glu Asn His Thr Ala Glu Leu
                210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
                260                 265                 270
Gly Ile Gln Asp Thr Asn Ser Lys Lys Gln Ser Asp Thr His Leu Glu
                275                 280                 285
Glu Thr
    290

<210> SEQ ID NO 2
<211> LENGTH: 873
<212> TYPE: DNA
<213> ORGANISM: Homo sapiens

<400> SEQUENCE: 2
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca agcgaattac tgtgaaagtc aatgccccat acaacaaaat caaccaaaga     420
attttggttg tggatccagt cacctctgaa catgaactga catgtcaggc tgagggctac     480
cccaaggccg aagtcatctg acaagcagt gaccatcaag tcctgagtgg taagaccacc     540
```

| | | | | | | |
|---|---|---|---|---|---|---|
| accaccaatt | ccaagagaga | ggagaagctt | ttcaatgtga | ccagcacact | gagaatcaac | 600 |
| acaacaacta | atgagatttt | ctactgcact | tttaggagat | tagatcctga | ggaaaaccat | 660 |
| acagctgaat | tggtcatccc | agaactacct | ctggcacatc | ctccaaatga | aaggactcac | 720 |
| ttggtaattc | tgggagccat | cttattatgc | cttggtgtag | cactgacatt | catcttccgt | 780 |
| ttaagaaaag | ggagaatgat | ggatgtgaaa | aaatgtggca | tccaagatac | aaactcaaag | 840 |
| aagcaaagtg | atacacattt | ggaggagacg | taa | | | 873 |